US006001563A

United States Patent [19]
Deeley et al.

[11] Patent Number: 6,001,563
[45] Date of Patent: *Dec. 14, 1999

[54] METHODS FOR IDENTIFYING CHEMOSENSITIZERS

[75] Inventors: Roger G. Deeley; Susan P.C. Cole, both of Kingston, Canada

[73] Assignee: Queen's University at Kingston, Kingston, Canada

[ * ] Notice: This patent is subject to a terminal disclaimer.

[21] Appl. No.: 08/463,179

[22] Filed: Jun. 5, 1995

Related U.S. Application Data

[63] Continuation-in-part of application No. 08/407,207, Mar. 20, 1995, which is a continuation-in-part of application No. 08/141,893, Oct. 26, 1993, Pat. No. 5,489,519, which is a continuation-in-part of application No. 08/029,340, Mar. 8, 1993, abandoned, which is a continuation-in-part of application No. 07/966,923, Oct. 27, 1992, abandoned.

[51] Int. Cl.$^6$ .............................. C12Q 1/68; C12Q 1/00; C12Q 1/02; C12N 5/00
[52] U.S. Cl. ................................. 435/6; 435/325; 435/6; 435/4; 435/29; 800/2; 800/DIG. 1-4; 800/13; 424/9.1
[58] Field of Search ................................. 435/4, 29, 325; 800/13

[56] References Cited

U.S. PATENT DOCUMENTS

| | | | |
|---|---|---|---|
| 4,912,039 | 3/1990 | Riordan | 435/69.1 |
| 5,166,059 | 11/1992 | Pastan et al. | 435/69.7 |
| 5,198,344 | 3/1993 | Croop et al. | 435/69.1 |
| 5,206,352 | 4/1993 | Roninson et al. | 536/24.31 |

OTHER PUBLICATIONS

Salter et al, Transgenic Chickens: Insertion of Retroviral Genes into the Chicken Germ Line, Virology vol. 157, pp. 236–240, 1987.

Pursel et al, Genetic Engineering of Livestock, Science vol. 244 pp. 1281–1288, Jun. 16, 1989.

Houdebine, Louis–Marie, Production of Pharmaceutical Proteins from Transgenic Animals, J. of Biotechnol. vol. 34 pp. 269–287, 1994.

Krimpenfort et al. Generation of transgenic dairy cattle using 'in vitro' embryo production. Biotechnology, vol. 9, pp. 844–847, Sep. 1991.

Abbaszadegan, M.R. et al. (1994) "Analysis of Multidrug Resistance–associated Protein (MRP) Messenger RNA in Normal and Malignant Hematopoietic Cells" *Cancer Research* 54: 4676–4679.

Almquist, K.C. et al. (1995) "Characterization of the $M_r$ 190,000 Multidrug Resistance Protein (MRP) in Drug–Selected and Transfected Human Tumor Cells" *Cancer Research* 55: 102–110.

Barrand, M.A. et al. (1992) "Chemosensitisation and Drug Accumulation Effects of Cyclosporin A, PSC–833 and Verapamil in Human MDR Large Cell Lung Cancer Cells Expressing a 190K Membrane Protein Distinct from P–glycoprotein" *Eur J. Cancer* 29A(3):408–415.

Bordow, S.B. et al. (1994) "Expression of the Multidrug Resistance–associated Protgein (MRP) Gene Correlates with Amplification and Overexpression of the N–myc Oncogene in Childhood Neuroblastoma" *Cancer Research* 54: 5036–5040.

Brock, I. et al. (1995) "Sequential Coexpression of the Multidrug Resistance Genes MRP and mdr1 and Their Products in VP–16 (Etoposide)–selected H69 Small Cell Lung Cancer Cells" *Cancer Research* 55: 459–462.

Burger, H. et al. (1994) "Expression of the Multidrug Resistance–Associated Protein (MRP) in Acute and Chronic Leukemias" *Leukemia* 8(6): 990–997.

Chen, C–J. et al. (1986) "Internal Duplication and Homology with Bacterial Transport Proteins in the mdr1 (P–Glycoprotein) Gene from Multidrug–Resistant Human Cells" *Cell* 47: 381–389.

Cole, S.P.C. et al. (1993) "A Novel ATP–Binding Cassette Transporter Gene Overexpressed in Multidrug–Resistant Human Lung Tumor Cells" *Proc. Am. Assoc. Cancer. Res.* 34: 579 (Abstract).

Cole, S.P.C. et al. (1989) "Effect of Calcium Antagonists on the Chemosensitivity of Two Multidrug–Resistant Human Tumor Cell Lines Which do not Overexpress P–glycoprotein" *Br. J. Cancer* 59:42–46.

Cole, S.P.C. et al. (1992) "Elevated Expression of Annexin II (Lipocortin II, p36) in a Multidrug Resistant Small Cell Lung Cancer Cell Line", *J. Cancer* 65: 498–502.

Cole, S. P.C. et al. (1993) "MRP: A Novel ATP–Binding Cassette Transporter Gene Isolated From a Multidrug Resistant Small Cell Lung Cancer Cell Line" *Third International IASLC Workshop on Lung Tumor and Differentiation Antigens* (Abstract).

Cole, S.P.C. and R.G. Deeley (1993) "Multidrug Resistance–Associated Protein: Sequence Correction" *Science* 260: 879.

Cole, S.P.C. et al (1992) "Overexpression of a Transporter Gene in a Multidrug–Resistant Human Lung Cancer Cell Line" *Science* 258:1650–1654.

Cole, S.P.C. (1990) "Patterns of Cross–Resistance in a Multidrug–Resistant Small–Cell Lung Carcinoma Cell Line" *Cancer Chemother.Pharmacol* 26: 250–256.

(List continued on next page.)

*Primary Examiner*—Brian R. Stanton
*Assistant Examiner*—Deborah J. R. Clark
*Attorney, Agent, or Firm*—Carol Miernicki Steeg; Catherine J. Kara; Giulio A. DeConti, Jr.

[57] ABSTRACT

A novel protein associated with multidrug resistance in living cells and capable of conferring multidrug resistance on a cell is disclosed. Nucleic acids encoding the novel multidrug resistance protein are also disclosed. Transformant cell lines which express the nucleic acid encoding the novel protein are also disclosed. Antibodies which bind the novel multidrug resistance protein are also disclosed. Diagnostic and treatment methods using the novel proteins, nucleic acids, antibodies and cell lines of the invention are also encompassed by the invention.

16 Claims, 21 Drawing Sheets

OTHER PUBLICATIONS

Cole, S.P.C. et al. (1994) "Pharmacological Characterization of Multidrug Resistant MRP–transfected Human Tumor Cells" *Cancer Research* 54: 5902–5910.

Cole, S.P.C. (1991) "The 1991 Merck Frosst Award. Multidrug Resistance in Small Cell Lung Cancer" *Can. J. Physiol. Pharmacol.* 70: 313–329.

DelaFlor–Weiss, E. et al. (1992) "Transfer and Expression of the Human Multidrug Resistance Gene in Mouse Erythroleukemia Cells" *Blood* 80(12):3106–3111.

Flens, M.J. et al. (1994) "Immunochemical Detection of the Multidrug Resistance–associated Protein MRP in Human Multidrug–resistant Tumor Cells by Monoclonal Antibodies" *Cancer Research* 54: 4557–4563.

Fojo, A.T. et al. (1985) "Amplification of DNA Sequences in Human Multidrug–Resistant KB Carcinoma Cells" *Proc. Natl. Acad. Sci. USA* 82:7661–7665.

Grant, C.E. et al. (1994) "Overexpression of Multidrug Resistance–Associated Protein (MRP) Increases Resistance to Natural Product Drugs" *Cancer Research* 54: 357–361.

Gros, P. et al. (1986) "Isolation and Characterization of DNA Sequences Amplified in Multidrug–Resistant Hamster Cells" *Proc. Natl. Acad. Sci. USA* 83: 337–341.

Higgins, C.F. (1992) "ABC Transporters: From Microorganisms to Man" *Annu. Rev. Cell Biol.* 8:67–113.

Hipfner, D.R. (1994) "Detection of the $M_r$ 190,000 Multidrug Resistance Protein, MRP, with Monoclonal Antibodies" *Cancer Research* 54: 5788–5792.

Hyde, S.C. et al. (1990) "Structural Model of ATP–Binding Proteins Associated With Cystic Fibrosis, Multidrug Resistance and Bacterial Transport" (1990) *Nature* 346:362–365.

Jeditschky, G. et al. (1994) "ATP–Dependent Transport of Glutathione S–Conjugates by the Multidrug Resistance–Associated Protein" *Cancer Research* 54: 4833–4836.

Jirsch, R.G. et al. (1993) "Inwardly Rectifying $K^+$ Channels and Volume–regulated Anion Channels in Multidrug–resistant Small Cell Lung Cancer Cells" *Cancer Research* 53:1–5.

Krebes, K.A. et al. (1993) "Peripheral Blood Mononuclear Cells Express Antigens Associated with Multidrug Resistance in a Small Cell Lung Cancer Cell Line" *Anticancer Research* 13: 317–322.

Krishnamachary, N. and M.S. Center (1993) "The MRP Gene Associated with a Non–P glycoprotein Multidrug Resistance Encodes a 190–kDa Membrane Bound Glycoprotein" *Cancer Research* 55: 3658–3661.

Kruh, G.D. et al. (1994) "Expression Complementary DNA Library Transfer Establishes mrp as a Multidrug Resistance Gene" *Cancer Research* 54: 1649–1652.

Kuss, B.J. et al. (1994) "Deletion of Gene for Multidrug Resistance in Acute Myeloid Leukaemia with Inversion in Chromosome 16: Prognostic Implications" *The Lancet* 343:1531–1534.

Leier, Inka et al. (1994) "The MRP Gene Encodes an ATP–dependent Export Pump for Leukotriene $C_4$ and Structurally Related Conjugates" *The Journal of Biological Chemistry* 269(45): 27807–27810.

Marquardt, D. et al. (1990) "Mechanisms of Multidrug Resistance in HL60 Cells: Detection of Resistance–Associated Proteins with Antibodies Against Synthetic Peptides That Correspond to the Deduced Sequence of P–Glycoprotein" *Cancer Res.* 50:1426–1430.

Mirski, S.E.L. et al. (1987) "Multidrug Resistance in a Human Small Cell Lung Cancer Cell Llne Selected in Adriamycin" *Cancer Research* 47: 2594–2598.

Ouellette, M. et al. (1990) "The Amplified H Circle of Methotrexate–Resistant Leishmania Tarentolae Contains a Novel P–glycoprotein Gene" *EMBO J.* 9(4):1027–1033.

Papadopoulou, B. et al. (1994) "Contribution of the Leishmania P–glycoprotein–related Gene ItpgpA to Oxyanion Resistance" *Journal of Biological Chemistry* 269(16): 11980–11986.

Podda, S. et al. (1992) "Transfer and Expression of the Human Multiple Drug Resistance Gene into Live Mice" *Proc. Natl. Acad. Sci. USA* 89:9676–9680.

Riordan, J.R. et al. (1985) "Amplification of P–glycoprotein Genes in Multidrug–Resistant Mammalian Cell Lines" *Nature* 316:817–819.

Rivoltini, L. et al. (1990) "Modulation of Multidrug Resistance By Verapamil or mdr1 Anti–Sense Oligodeoxynucleotide Does Not Change The High Susceptibility to Lymphokine–Activated Killers in mdr–Resistant Human Carcinoma (LoVo) Line" *Int. J. Cancer* 46:727–732.

Roninson, I.B. et al. (1984) "Amplification of Specific DNA Sequences Correlates with Multi–drug Resistance in Chinese Hamster Cells" *Nature* 309: 626–628.

Roninson, I.B. et al. (1986) "Isolation of Human mdr DNA Sequences Amplified in Multidrug–Resistant KB Carcinoma Cells" *Proc. Natl. Acad. Sci. USA* 83:4538–4542.

Slovak, M.L. et al. (1993) "Localization of a Novel Multidrug Resistance–associated Gene in the HT1080/DR4 and H69AR Human Tumor Cell Lines" *Cancer Research* 53: 3221–3225.

Sumizawa, T. et al. (1994) "Non–P–Glycoprotein–Mediated Multidrug–Resistant Human KB Cells Selected in Medium Containing Adriamycin, Cepharanthine, and Mezerein" *Somatic Cell and Molecular Genetics* 20(5): 423–435.

Sugawara, I. et al. (1994) "Expression of Multidrug Resistance–associated Protein (MRP) in Anaplastic Carcinoma of the Thyroid" *Cancer Letters* 82: 185–188.

Szczypka, M.S. (1994) "A Yeast Metal Resistant Protein Similar to Human Cystic Fibrosis Transmembrane Conductance Regulator (CFTR) and Multidrug Resistance–associated Protein" *Journal of Biological Chemistry* 269(36): 22853–22857.

Ueda, K. et al. (1986) "The mdr1 Gene, Responsible For Multidrug–Resistance, Codes For P–Glycoprotein" *Biochem. and Biophys. Res. Comm.* 141(3):956–962.

Zaman, G.J.R. et al. (1994) "The Human Multidrug Resistance–associated Protein MRP is a Plasma Membrane Drug–fflux Pump" *Proc. Natl. Acad. Sci USA* 91: 8822–8826.

| | | |
|---|---|---|
| Hum/MRP | MALRGFCSADGSDPLWDWNVTWNTSNPDFTKCFQNTV | 37 |
| Hum/MRP | LVWVPCFYLWACFPFYFLYLSRHDRGYIQMTPLNKTK | 74 |
| Lei/PgpA | MVDNGHVT | 8 |
| Hum/MRP | TALGFLLWIVCWADLFY-SFWERSRGIFLAPVFLVSP | 110 |
| Lei/PgpA | IAMADLGTVVEIAQVRCQQEAQRKFAEQLDELWGGEP | 45 |
| Hum/MRP | TLLGITTLLATFLIQLERRKGVQSSGIMLTFWLVALV | 147 |
| Lei/PgpA | AYTPTVEDQASWFQQL-----------YYGWIGDYI | 70 |
| Hum/MRP | CALAILRSKIMTALKEDAQVDLFRDITFYVYFSLLLI | 184 |
| Lei/PgpA | YKAAA--GNITEA---DLPPPTRSTRTYHIGRKLSRQ | 102 |
| Hum/MRP | QLVLSCFSDRSPLFSETIHDPNPCPESSASFLSRITF | 221 |
| Lei/PgpA | AHADIDASRRWQGYIGCEVVYKSCAEAKG------VL | 133 |
| Hum/MRP | WWITGLIVRGYRQPLEGSDLWSLNKEDTSEQVVPVLV | 258 |
| Lei/PgpA | RWVGHLQQSDYPRSLVAGVEWRMP-----------P | 158 |
| Hum/MRP | KNWKKECAKTRKQPVKVVYSSKDPAQPKESSKVDANE | 295 |
| Lei/PgpA | RHRRLAVLGSAAALHNGVVHGERLFWPHEDNYLCSCE | 195 |
| Hum/MRP | EVEALIVKS------PQKEWNPSLFKVLYKTFGPYFL | 326 |
| Lei/PgpA | PVEQLYVKSKYNLIPPRPPPSPDLLRTLFKVHWYHVW | 232 |

Fig. 3A-1

```
Hum/MRP   MSFFFKAIHDLMMFSGPQILKLLIKFVNDTKAPDWQG    363
          . : :.   . : .:  ..:..:   :     :
Lei/PgpA  AQILPKLLSDVTALMLPVLLEYFVKYLNADNATWGWG    269

Hum/MRP   YFYTVLLFVTACLQTLVLHQYFHICFVSGMRIKTAVI    400
          . .:.:  .:      : : ::            :
Lei/PgpA  LGLALTIFLTNVIQSCSAHKYDHISIRTAALFETSSM    306

Hum/MRP   GAVYRKALVITNSA--RKSSTVGEIVNLMSVDAQRFM    435
          .. : . .        :     :: : :.     :
Lei/PgpA  ALLFEKCFTVSRRSLQRPDMSVGRIMNMVGNDVDNIG    343

Hum/MRP   DLATYINMIWSAPLQVILALYLLWLNLGPSVLAGVAV    472
          :   :..    :::::::...: : ::    .:  . : ::
Lei/PgpA  SLNWYVMYFWSAPLQLVLCLLLLIRLVGWLRVPGMAV    380

Hum/MRP   MVLMVPVNAVMAMKTKTYQVAHMKSKDNRIKLMNEIL    509
          . . .:. ::              : ::: ::.:
Lei/PgpA  LFVTLPLQAVISKHVQDVSERMASVVDLRIKRTNELL    417

Hum/MRP   NGIKVLKLYAWELAFKDKVLAIRQEELKVLKKSAYLS    546
          :.....:.  ::  :   ..    :  ::. :.
Lei/PgpA  SGVRIVKFMGWEPVFLARIQDARSRELRCLRDVHVAN    454

Hum/MRP   AVGTFTWVCTPFLVALCTFAVYVTIDENNILDAQTAF    583
          :      :: ::     :  .:           .:      :
Lei/PgpA  VFFMFVNDATPTLVIAVVFILYHV--SGKVLKPEVVF    489

Hum/MRP   VSLALFNILRFPLNILPMVISSIVQASVSLKRLRIFL    620
          .::..  .:   .  .:  .::::.:  :: ::.   :.
Lei/PgpA  PTIALLNTMRVSFFMIPIIISSILQCFVSAKRVTAFI    526

Hum/MRP   SHEE---------------LEPDSIE-------       631
          .                       . ::
Lei/PgpA  ECPDTHSQVQDIASIDVPDAAAIFKGASIHTYLPVKL    563
```

Fig. 3A-2

```
Hum/MRP    ------------------RRPVKD---------GGGT      641
                             :: :  .
Lei/PgpA   PRCKSRLTAMQRSTLWFRRRGVPETEWYEVDSPDASA       600

Hum/MRP    NSITVRNATFTWARSDPPT------------------      660
            :. :    :
Lei/PgpA   SSLAVHSTTVHMGSTQTVITDSDGAAGEDEKGEVEEG       637

Hum/MRP    ------------LNGITFSIPEGALVAVVGQVGCGKL       685
                        :  . .::  :  :  :.:  : ::
Lei/PgpA   DREYYQLVSKELLRNVSLTIPKGKLTMVIGSTGSGKS       674
                                          A

Hum/MRP    SLLSALLAEMDKVEGHVAIKGSVAYVPQQAWIQNDSL       722
           ::  ::. :      : .      :.::::::::: :  :
Lei/PgpA   TLLGALMGEYSVESGELWAERSIAYVPQQAWIMNATL       711

Hum/MRP    RENILFGCQLEEPYYRSVIQACALLPDLEILPSGDRT       759
           :  ::::     ::   : :   : ::   .  :   :
Lei/PgpA   RGNILFFDEERAEDLQDVIRCCQLEADLAQFCGGLDT       748

Hum/MRP    EIGEKGVNLSGGQKQRVSLARAVYSNADIYLFDDPLS       796
           ::::  :::::::::: :::::::::: :  :..:.:::::
Lei/PgpA   EIGEMGVNLSGGQKARVSLARAVYANRDVYLLDDPLS       785
                      C                 B

Hum/MRP    AVDAHVGKHIFENVIGPKGMLKNKTRILVTHSMSYLP       833
           :..::::: :    ::    : :.. :::.: ::        ::
Lei/PgpA   ALDAHVGQRIVQDVI--LGRLRGKTRVLATHQIHLLP       820

Hum/MRP    QVDVIIVMSGGKISEMGSYQELLARDGAFAEFLRTYA       870
           : :..:.  :  :    :  : . :     :. :::
Lei/PgpA   LADYIVVLQHGSIVFAGDFAAFSA--TALEETLR---       852

Hum/MRP    STEQEQDAEENGVTGVSGPGKEAKQMENGMLVTDSAG       907
            :    :    :         .          . :.::
Lei/PgpA   -------GELKGSKDVESCSSD--------VDTESAT       874
```

Fig. 3A-3

```
Hum/MRP   KQLQRQLSSSSSYSGDISRHHNSTAELQKAEAKKEET        944
          .              .    : :              :
Lei/PgpA  AETAPYVAKAKGLNAE---QETSLAGGEDPLRSDVEA        908

Hum/MRP   WKLMEADKAQTGQVKLSVYWDYMKAIGLFISFLSIF-        980
          .:: .    :: :  : :  :.: :  .  ..
Lei/PgpA  GRLMTTEEKATGKVPWSTYVAYLKSCGGLEAWGCLLA        945
                                             ---

Hum/MRP   -LFMCNHVSALASNYWLSLWTDDPIVNGTQEHTKVRL       1016
           . .   : : ::  :::.:     .        : :
Lei/PgpA  TFALTECVTA-ASSVWLSIWSTGSLMWSADTYLYVYL        981
          ----------------

Hum/MRP   SVYGALGISQGIAVFGYSMAVSIGGILASRCLHVDLL       1053
           .         . :  . ::    ::  .: :::
Lei/PgpA  FIVFLEIFGSPLRFFLCYYLIRIG----SRNMHRDLL       1014

Hum/MRP   HSILRSPMSFFERTPSGNLVNRFSKELDTVDSMIPEV       1090
          ::    ::::. :: :  ..:::  :..  .:  . .
Lei/PgpA  ESIGVARMSFFDTTPVGRVLNRFTKDMSILDNTLNDG       1051

Hum/MRP   IKMFMGSLFNVIGACIVILLATPIAAIIPPLGLIYF        1127
          ..  .:      :. .. :   .: :        :.
Lei/PgpA  YLYLLEYFFSMCSTVIIMVVVQPFVLVAIVPCVYSYY       1088

Hum/MRP   FVQRFYVASSRQLKRLESVSRSPVYSHFNETLLGVSV       1164
           .  : :: :  .:. :.  :::.  . : :
Lei/PgpA  KLMQVYNASNRETRRIKSIAHSPVFTLLEESLQGQRT       1125

Hum/MRP   IRAFEEQERFIHQSDLKVDENQKAYYPSIVANRWLAV       1201
          :   .       ..:   : :    : ::::  :
Lei/PgpA  IATYGKLHLVLQEALGRLDVVYSALYMQNVSNRWLGV       1162

Hum/MRP   RLECVGNCIVLFAALFAVISR----HSLSAGLVGLSV       1234
          :::  .   . . :. :: .     :  ::. ::.
Lei/PgpA  RLEFLSCVVTFMVAFIGVIGKMEGASSQNIGLISLSL       1199
```

Fig. 3A-4

```
Hum/MRP   SYSLQVTTYLNWLVRMSSEMETNIVAVERLKEYS-ET    1270
          :.  .: :::::::        : :    :::.   :  :
Lei/PgpA  TMSMTLTETLNWLVRQVAMVEANMNSVERVLHYTQEV    1236

Hum/MRP   EKE-----APWQIQETRPPSSWP--------------    1288
          : :          :   :   :  .
Lei/PgpA  EHEHVPEMGELVAQLVRSESGRGANVTETVVIESAGA    1273

Hum/MRP   --------QVGRVEFRNYCLRYREDLDFVLRHINVTI    1317
                  :  :  . .    .::::  :  .:::  .    :
Lei/PgpA  ASSALHPVQAGSLVLEGVQMRYREGLPLVLRGVSFQI    1310

Hum/MRP   NGGEKVGIVGRTGAGKSSLTLGLFRINESAEGEIIID    1354
          :::::::::::: :::  :  .  :    :    : :  .
Lei/PgpA  APREKVGIVGRTGSGKSTLLLTFMRMVEVCGGVIHVN    1347
                       A

Hum/MRP   GINIAKIGLHDLRFKITIIPQDPVLFSGSLRMNLDPF    1391
          :    ::  .::    :::::::::  :  .: :.:::
Lei/PgpA  GREMSAYGLRELRRHFSMIPQDPVLFDGTVRQNVDPF    1384

Hum/MRP   SQYSDEEVWTSLELAHLKDFVSALPDKLDHECAEGGE    1428
          :   :::   :::    :...  :      . .:     :::
Lei/PgpA  LEASSAEVWAALELVGLRERVASESEGIDSRVLEGGS    1421

Hum/MRP   NLSVGQRQLVCLARALLRKTK-ILVLDEATAAVDLET    1464
          : :::::::: :..::::::..  ...:::::  .:
Lei/PgpA  NYSVGQRQLMCMARALLKRGSGFILMDEATANIDPAL    1458
           C                     B

Hum/MRP   DDLIQSTIRTQFEDCTVLTIAHRLNTIMDYTRVIVLD    1501
          :  ::  :.    :   .::.::::::: :.    :  ..:::
Lei/PgpA  DRQIQATVMSAFSAYTVITIAHRLHTVAQYDKIIVMD    1495

Hum/MRP   KGEIQEYGAPSDL-LQQRGLFYSMAKDAGLV         1531
          :  . :   :    : .:  .     .: ::        :
Lei/PgpA  HGVVAEMGSPRELVMNHQSMFHSMVESLGSRGSKDFY   1532

Lei/PgpA  ELLMGRRIVQPAVLSD                        1548
```

| | | | |
|---|---|---|---|
| Hum/MRP (C) | LRHINVTINGGEKVGIVGRTGAGKSSLTLGLFRINESAEGEIIIDGINIAKIGHDLRFKITLIPQDPVLFSGSLRMNL | 1388 |
| Lei/PgpA (C) | LRGVSFQIAPREKVGIVGRTGSGKSTLLLTLMRMVEVCGGVIHVNGREMSAYGLREIRRHFSMIPQDPVLFDGTVRQNV | 1381 |
| Hum/CFTR (C) | LENISFSISPGQRVGLLGRTCSGKSTLLSAFLRLLN-TEGEIQIDGVSWDSITLQQWRKAFGVIPQKVFIFSGTFRKNL | 1304 |
| Hum/Mdr1 (C) | LQGLSLEVKKGQTLALVGSSGCGKSTVVQLLERFYDPLAGKVLLDGKEIKRLNVQWLRAHLGIVSQEPILFDCSIAENIAYG | 1134 |

A

| | | | |
|---|---|---|---|
| Hum/MRP (C) | DPFSQYSDEEVWTSLELAHLKDFVSALPDKLDHECAEGGENLSVGQRQLVCLARALLRKTK-ILVLDEATAAVDLETDDLIQ | 1469 |
| Lei/PgpA (C) | DPFLEASSAEVWAALELVGLRERVASESEGIDSRVLEGGSNYSVGQRQLMCMARALLKRGSGFILMDEATANIDPALDROIQ | 1463 |
| Hum/CFTR (C) | DPYEQWSDQEIWKVADEVGLRSVIEQFPGKLDFVLVDGGCVLSHGHKQLMCLARSVLSKAK-ILLLDEPSAHLDPVTYQIIR | 1385 |
| Hum/Mdr1 (C) | DNSRVVSQEEIVRAAKEANIHAFIESLPNKYSTKVGDKGTQLSGGQKQRIAIARALVRQPH-ILLLDEATSALDTESEKVVQ | 1215 |

C                                          B

METHODS FOR IDENTIFYING CHEMOSENSITIZERS

CROSS REFERENCE TO RELATED APPLICATIONS

This application is a continuation-in-part of application Ser. No. 08/407,207 filed Mar. 20, 1995, pending, which is a continuation-in-part of application Ser. No. 08/141,893 filed Oct. 26, 1993, now U.S. Pat. No. 5,489,519, issued Feb. 6, 1996, which is a continuation-in-part of application Ser. No. 08/029,340 filed Mar. 8, 1993, now abandoned, which is a continuation-in-part of application Ser. No. 07/966,923 filed Oct. 27, 1992, now abandoned, the entire contents of each of which are incorporated herein by reference.

BACKGROUND OF THE INVENTION

It is well known that many types of cancer regress initially in response to currently available drugs. However, if the disease should recur, as it does with variable frequency, it is often refractory to further treatment with either the agent originally used for treatment or agents to which the patient has not been previously exposed. Currently there is little that can be done for patients whose tumors display this form of multidrug resistance.

One mechanism by which cancer cells can simultaneously develop resistance to an array of structurally diverse drugs has been elucidated over the last 15 years with the characterization of P-glycoprotein.

P-glycoprotein is a member of a superfamily of membrane proteins that serve to transport a variety of molecules, ranging from ions to proteins, across cell membranes. This superfamily is known as the ATP-binding cassette (ABC) superfamily of membrane transport proteins. For a review see C. F. Higgins, *Ann. Rev. Cell Biol.* 8, 67 (1992). For example, in addition to P-glycoprotein which transports chemotherapeutic drugs, this family includes the cystic fibrosis transmembrane conductance regulator, which controls chloride ion fluxes, as well as insect proteins that mediate resistance to antimalarial drugs. P-glycoprotein is believed to confer resistance to multiple anticancer drugs by acting as an energy dependent efflux pump that limits the intracellular accumulation of a wide range of cytotoxic agents and other xenobiotics. Compounds that are excluded from mammalian cells by P-glycoprotein are frequently natural product-type drugs but other large heterocyclic molecules are also "substrates" for this efflux pump.

The discovery of P-glycoprotein and its occurrence in a variety of tumor types has stimulated the search for compounds that are capable of blocking its function and consequently, of reversing resistance. These investigations have resulted in identification of a large number of so-called chemosensitizers or reversing agents. Some of these compounds act by inhibiting the pumping action of P-glycoprotein while the mechanism of action of others is still undetermined. A select group of these agents are currently under intensive clinical investigation and they show considerable promise as adjuncts to conventional chemotherapy. Chemosensitizers which can reverse P-glycoprotein-mediated multidrug resistance include verapamil and cyclosporin A.

Unfortunately, overexpression of P-glycoprotein does not explain the high frequency of multidrug resistance in some of the more prevalent forms of cancer, such as lung cancer. In the Western world, lung cancer accounts for approximately 30% of total cancer deaths. There are four major histological categories of lung tumors: epidermoid or squamous cell adenocarcinomas, large cell carcinomas, adenocarcinomas and small cell carcinomas. The first three categories, known collectively as non-small cell lung cancers, differ from the last in their initial response to chemotherapy and radiotherapy. Non-small cell lung cancers are relatively resistant to both forms of treatment from the outset. In contrast, small cell lung cancer, which accounts for 20% of all lung tumors, exhibits a high initial response rate (80–90% in limited disease) to chemotherapy. However, almost all patients relapse with a multidrug resistant form of the disease and two year survival rates are less than 10%. Although the drug resistance profile displayed in relapsed small cell lung cancer patients is similar to that conferred by P-glycoprotein, P-glycoprotein appears not to be involved. In addition, limited studies in cell culture and in patients indicate that multidrug resistance in small cell lung cancer does not respond to chemosensitizers, such as verapamil and cyclosporin A, that show promise with other types of drug resistant tumors.

Survival rates in lung cancer have not improved significantly in forty years and, because of its common occurrence, there is clearly a great need for improved therapy for this disease.

SUMMARY OF THE INVENTION

The present invention is based, at least in part, on the discovery of a nucleic acid which encodes a protein which can confer multidrug resistance on a drug sensitive mammalian cell when expressed in the cell and which is overexpressed in certain multidrug resistant cancer cell lines. The nucleic acid of the invention was isolated from a multidrug resistant cancer cell line which does not overexpress P-glycoprotein and whose resistance is not substantially reversed by chemosensitizers which inhibit P-glycoprotein. The nucleic acid and encoded protein of the present invention represent molecules which can be targeted therapeutically in multidrug resistant tumors expressing the nucleic acid and protein.

The present invention provides an isolated nucleic acid having a nucleotide sequence which encodes a protein associated with multidrug resistance which is overexpressed in multidrug resistant cells independently of overexpression of P-glycoprotein. The protein has been named multidrug resistance-associated protein (referred to as MRP). The protein of the invention differs in amino acid sequence from P-glycoprotein. The isolated nucleic acid, when expressed in a cell which is not multidrug resistant, can confer on the cell multidrug resistance.

In a preferred embodiment, an isolated nucleic acid is provided having a sequence which codes for a protein associated with multidrug resistance having an amino acid sequence which has substantial sequence homology with the amino acid sequence shown in SEQ ID NO: 2. Most preferably the isolated nucleic acid has a sequence having substantial sequence homology with the nucleotide sequence shown in SEQ ID NO: 1. In one embodiment, the invention provides an isolated human MRP nucleic acid molecule, as shown in SEQ ID NO: 1 and encoding a human MRP protein as shown in SEQ ID NO: 2. In another embodiment, the invention provides a natural variant of the human MRP nucleic acid molecule of SEQ ID NO: 1, shown in SEQ ID NO: 3 and encoding a human MRP protein shown in SEQ ID NO: 4, which differs by three nucleotide base pairs from the sequence of SEQ ID NO: 1. In yet another embodiment, the invention provides an isolated mouse MRP nucleic acid molecule, as shown in SEQ ID NO: 5 and encoding a mouse MRP protein as shown in SEQ ID NO: 6. The invention further provides an isolated nucleic acid which is antisense to a nucleic acid having substantial sequence homology with the nucleotide sequence shown in SEQ ID NO: 1.

The invention further provides a recombinant expression vector adapted for transformation of a host cell comprising the nucleic acid of the invention operatively linked to a regulatory sequence. The invention also provides a recombinant expression vector adapted for transformation of a host cell comprising a DNA molecule operatively linked to a regulatory sequence to allow expression of an RNA molecule which is antisense to a nucleotide sequence of SEQ ID NO: 1.

The invention also provides a method of preparing a protein capable of conferring multidrug resistance utilizing the nucleic acid of the invention. The method comprises culturing a transformant host cell including a recombinant expression vector comprising a nucleic acid of the invention and an regulatory sequence operatively linked to nucleic acid in a suitable medium until a multidrug resistance protein is formed and thereafter isolating the protein.

The invention further provides an isolated protein having the biological activity of MRP, which can confer multidrug resistance on a drug sensitive cell when the protein is expressed in the cell, said resistance not being substantially reversed by chemosensitizers of P-glycoprotein. The isolated protein of the invention is associated with multidrug resistance in tumor cells and is overexpressed in multidrug resistant cells which may or may not overexpress P-glycoprotein. In a preferred embodiment the protein has an amino acid sequence which has substantial homology with the amino acid sequence shown in SEQ ID NO: 2.

The invention further provides an antibody specific for an epitope of a protein of the invention. Preferably the antibody is a monoclonal antibody. The antibody can be coupled to a detectable substance or a substance having toxic or therapeutic activity. The invention also provides a bispecific antibody capable of binding to a tumor cell which expresses a protein of the invention and to a detectable substance, or a substance having toxic or therapeutic activity. Preferably, the toxic substance is a cytotoxic cell and the bispecific antibody is capable of crosslinking the tumor cell and the cytotoxic cell thereby facilitating lysis of the tumor cell. The invention further provides a tetrameric antibody complex of a first monoclonal antibody which is capable of binding to a tumor cell expressing a protein of the invention and a second monoclonal antibody which is capable of binding to a detectable substance or a substance having toxic or therapeutic activity wherein the first and second antibody are from a first animal species, conjugated to form a cyclic tetramer with two monoclonal antibodies of a second animal species directed against the Fc fragment of the antibodies of the first animal species.

The antibodies, bispecific antibodies or tetrameric antibody complexes can be incorporated in compositions suitable for administration in a pharmaceutically acceptable carrier.

Molecules which bind to a protein of the invention, including the antibodies, bispecific antibodies and tetrameric antibody complexes of the invention, can be used in a method for identifying multidrug resistant tumor cells by labelling the molecule with a detectable substance, contacting the molecule with tumor cells and detecting the detectable substance bound to the tumor cells. A molecule which binds to a protein of the invention can further be used in a method for inhibiting multidrug resistance of a cell by blocking activity of an MRP protein. A molecule which binds to a protein of the invention can further be used to kill a multidrug resistant cell which expresses the protein by contacting the molecule, coupled to a toxic or therapeutic substance, with the multidrug resistant cell.

Nucleic acids of the invention can be used in a method for protecting a drug sensitive cell from cytotoxicity due to exposure to a drug by transfecting the cell with a nucleic acid in a form suitable for expression of the protein encoded by the nucleic acid in the cell, thereby conferring drug resistance on the cell.

The recombinant molecules of the invention can be used to produce transformant host cells expressing the protein of the invention. The recombinant molecules of the invention can be also used to produce transgenic nonhuman animals and nonhuman knockout animals. The transfected cells, transgenic animals and knockout animals can be used to test substances for their effect on multidrug resistance. A method for identifying a substance which is a chemosensitizer of a therapeutic agent and a method for identifying a cytotoxic substance for multidrug resistant cells, using transformant host cells or animals of the invention, are provided.

The invention also relates to a cell line which is multidrug resistant, does not overexpress P-glycoprotein and is substantially resistant to hydrophobic drugs. The cell line may be derived from small cell lung cancer cells, preferably the cell line NCI-H69. Most preferably the multidrug resistant cell line is H69AR (ATCC CRL 11351). A revertant drug sensitive cell line may be obtained from the multidrug resistant cell line by culturing the multidrug resistant cell line in the absence of a drug for a period of time sufficient to produce a revertant drug sensitive cell line. Preferably the revertant drug sensitive cell line is H69PR (ATCC CRL 11350).

BRIEF DESCRIPTIONS OF THE DRAWINGS

FIG. 3A is the complete amino acid sequence of the multidrug resistance protein of the invention aligned with the complete amino acid sequence of 1tPgpA (Lei/PgpA).

FIG. 3B is a diagram showing the alignment of the extended nucleotide binding regions of the multidrug resistance protein of the invention, human CFTR and leishmania 1tPgpA and human P-glycoprotein (Hum/Mdr1).

Figure 11:
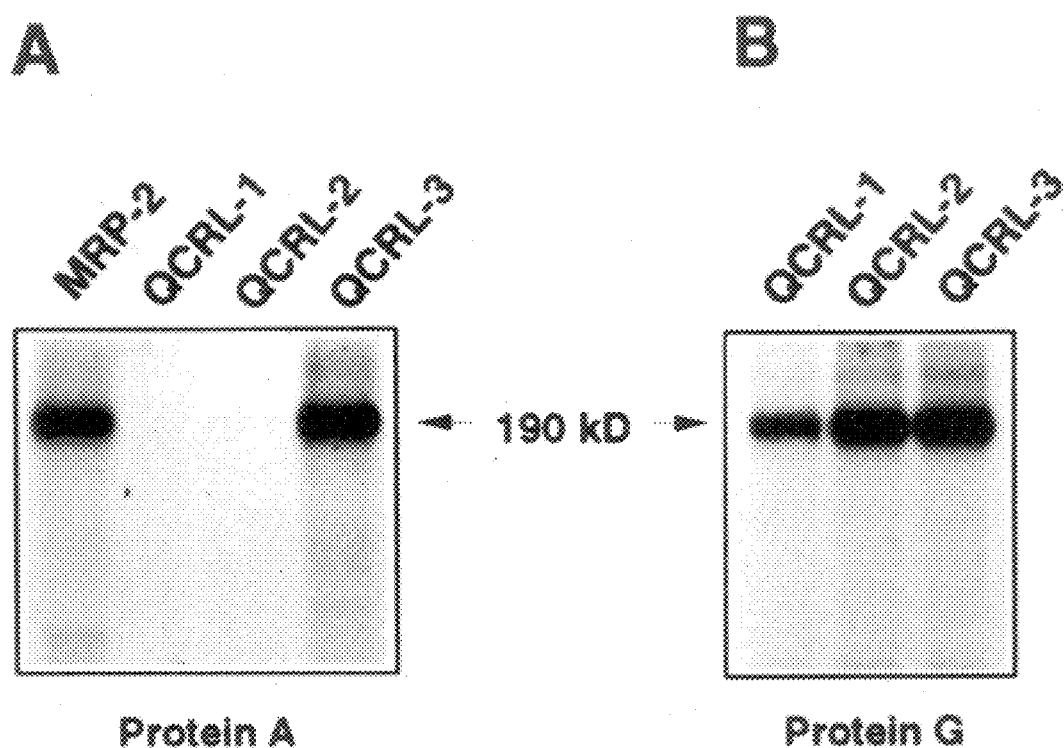

FIG. 11A–B are photographs of immunoprecipitation autoradiographs of labelled proteins from H69AR cells immunoprecipitated with anti-MRP mAbs (QCRL-1, -2 or -3) or anti-MRP peptide antisera (MRP-2). Immune complexes were precipitated with protein A-Sepharose (panel A) or protein G-Sepharose (panel B).

Figure 12:
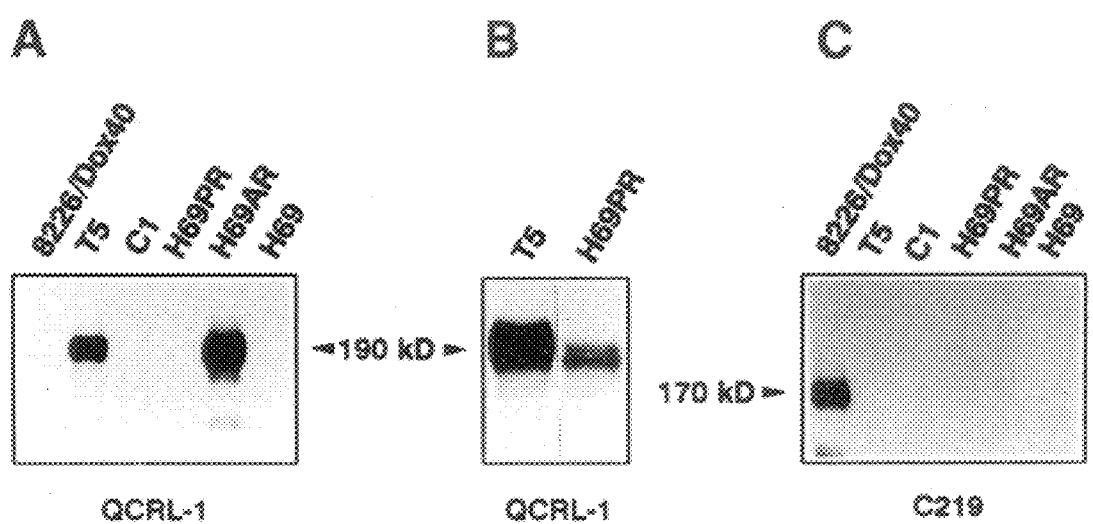

FIG. 12A–C are photographs of Western blots of proteins from membrane-enriched fractions of MRP-overexpressing cells (H69AR and T5), P-glycoprotein-overexpressing cells (8226/Dox40) or control cells (H69, H69PR and C1) screened with an anti-MRP mAb (QCRL-1) (panels A and B) or an anti-Pgp mAb (C219) (panel C).

FIG. 13A–B are flow cytometric profiles of fixed H69, H69AR or H69PR cells (panel A) or fixed T5 or C1 cells (panel B) reacted with anti-MRP mAb QCRL-3.

DETAILED DESCRIPTION OF THE INVENTION

Multidrug resistant mammalian cell lines have been derived from a number of tumor types and have provided in vitro models for the study of acquired resistance. Although selected by a single natural product-type drug, these cell lines are cross-resistant to a wide range of chemically unrelated xenobiotics with multiple subcellular targets. Typically, these cells are resistant to anthracyclines [e.g. doxorubicin (DOX), epipodophyllotoxins (e.g. VP-16) and the Vinca alkaloids (e.g. vinblastine)] but not to antimetabolites such as 5-fluorouracil, or to platinum-containing drugs. Multidrug resistant cells also frequently exhibit a collateral sensitivity to certain hydrophobic drugs including local anesthetics and steroid hormones.

The most commonly reported alteration in multidrug resistant tumor cells has been the increased expression of the 170 kDa plasma membrane glycoprotein, P-glycoprotein (P-gp), which is encoded by the MDR1 gene. Studies carried out in several laboratories with clinical samples and cell lines representing many tumor types have lead to the conclusion that P-gp, while clinically relevant in some malignancies, is unlikely to be important in others. Overexpression of P-gp is an infrequent occurrence in both small cell lung cancer (SCLC) and non small cell lung cancer (NSCLC).

One of the most widely used cell lines in experimental studies of SCLC is NCI-H69 (H69) (Gazdar et al., Cancer Res. 40, 3502–3507 (1980)) (ATCC HTB 119). This cell line was treated repeatedly with an anthracycline, such as daunorubicin or epirubicin and preferably DOX, and step-wise selected to a final concentration of 0.8 $\mu$M, to produce a multidrug resistant cell line, designated as H69AR. A description of the procedures which can be used to produce a multidrug resistant cell line such as H69AR is found in Cole, Cancer Chemother Pharmacol. 17, 259–263 (1986) and in Mirski et al., Cancer Research 47, 2594–2598 (1987).

The H69AR cell line (ATCC CRL 11351 ) is about 50-fold resistant to DOX as compared to the parental H69 cell line. H69AR is also cross-resistant to a wide variety of natural product-type drugs. On the other hand, drugs such as carboplatin, 5-fluorouracil and bleomycin are equally toxic to both sensitive H69 and resistant H69AR cells. Although the cross-resistance pattern of H69AR cells is typical of resistance associated with increased levels of P-gp, these cells are different in that they display little or no collateral sensitivity to hydrophobic drugs such as steroids or local anaesthetics. Another distinguishing feature of H69AR of potential clinical relevance that distinguishes it from P-gp overexpressing cell lines is the limited ability of verapamil, cyclosporin A and other chemosensitizing agents that interact with P-gp, to reverse DOX resistance in these cells. The absence of P-gp overexpression supports the suggestion that H69AR provides a clinically relevant model of drug resistance in lung cancer.

A revertant drug sensitive cell line H69PR (Cole et al., Br J. Cancer 65, 498–502, 1992) (ATCC CRL 11350) was isolated by culturing the H69AR cell line in the absence of drugs such as DOX for a sufficient time to produce a revertant cell line. Preferably the cell line H69PR is cultured in the absence of drugs for at least 3 months and up to about 48 months, most preferably 42 months.

The cell lines of the invention may be used to assay for a substance that affects a multidrug resistant tumor cell. Cells from a cell line of the invention may be incubated with a test substance which is suspected of affecting multidrug resistance. The effect of the substance can be determined by analyzing the drug resistance pattern of the cells and comparing the results to a control. As discussed above, the multidrug resistant cell line of the invention is resistant to anthracyclines, epipodophyllotoxins, Vinca alkaloids and other natural-product type drugs. Thus, it is possible to screen for an agonist or antagonist substance of multidrug resistance or an antagonist that inhibits the effects of an agonist.

In an embodiment of the invention, a substance that is suspected of being cytotoxic to a multidrug resistant tumor cell can be identified. Therefore, it is possible using the above described method to identify substances which may be useful in the treatment of multidrug resistant tumors.

As described in the Examples, the H69AR cell line has been used to identify a cDNA encoding a novel protein associated with multidrug resistance designated MRP. The DNA sequence and deduced amino acid sequence of MRP are shown in SEQ ID NO: 1 and SEQ ID NO. 2, respectively. MRP mRNA is overexpressed in certain multidrug resistant tumor cell lines, including H69AR. Furthermore, expression of MRP protein in a drug sensitive mammalian cell line confers multidrug resistance on the cell line. A protein described herein as "having biological activity of MRP" can confer on a mammalian cell multidrug resistance to anthracyclines, epipodophyllotoxins and Vinca alkaloids when the protein is expressed in the mammalian cell, and this resistance is not substantially reversed by chemosensitizers which reverse P-glycoprotein-mediated multidrug resistance, such as verapamil or cyclosporin A, in an MRP-dependent manner.

The terms "drug resistant" or "drug resistance" as used herein to describe a property of a cell refer to the ability of the cell to withstand without cytotoxicity increased concentrations of a drug as compared to an appropriate control cell. An appropriate control cell for a cell which has been made drug resistant by continued exposure to a drug is the parental cell from which the drug resistant cell was derived. An appropriate control cell for a cell which has been made drug resistant by expression in the cell of a protein which confers drug resistance on the cell is the same cell without the protein expressed. Appropriate control cells for naturally occurring tumor cells in vivo made drug resistant by continued exposure to a drug are the same tumor cells at the time of initial exposure to the drug.

The invention provides isolated nucleic acids encoding proteins having biological activity of MRP. In a preferred embodiment, the nucleic acid is a cDNA comprising a nucleotide sequence shown in SEQ ID NO: 1. The invention further provides antisense nucleic acids of nucleic acids encoding proteins having biological activity of MRP. The invention further provides recombinant expression vectors comprising the nucleic acids and antisense nucleic acids of the invention and transformant host cells containing recombinant nucleic acids of the invention.

The invention provides isolated proteins having biological activity of MRP and a method for preparing such proteins. In a preferred embodiment, the isolated protein having biological activity of MRP comprises an amino acid sequence shown in SEQ ID NO: 2. The protein comprising the amino acid sequence of SEQ ID NO: 2 is a member of the ABC superfamily of membrane transport proteins. The invention further provides antibodies specific for the isolated proteins of the invention and compositions suitable for administration comprising such antibodies. The invention further provides transgenic and knockout nonhuman animals produced using the nucleic acids of the invention.

The invention provides a method for identifying multi-drug resistant cell using the nucleic acids and antibodies of the invention. The invention further provides methods for inhibiting multidrug resistance of a multidrug resistant cell and for killing a multidrug resistant cell using the nucleic acids and antibodies of the invention. The invention further provides methods for identifying substances which are chemosensitizers of therapeutic agents or cytotoxic to drug resistant cells using the transformant host cells and animals of the invention. Furthermore, the invention provides diagnostic kits for identifying drug resistant tumor cells. These and other aspects of this invention are described in detail in the following subsections.

I. Isolated Nucleic Acids

The invention provides isolated nucleic acids encoding proteins having biological activity of MRP. The term "isolated" refers to a nucleic acid substantially free of cellular material or culture medium when produced by recombinant DNA techniques, or chemical precursors or other chemicals when chemically synthesized. An "isolated" nucleic acid is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded. In a preferred embodiment, the nucleic acid is a cDNA comprising a nucleotide sequence shown in SEQ ID NO: 1. In another embodiment, the nucleic acid is a cDNA comprising the coding region of the nucleotide sequence shown in SEQ ID NO: 1. In another embodiment, the nucleic acid encodes a protein comprising an amino acid sequence shown in SEQ ID NO: 2.

It will be appreciated that the invention includes nucleic acids having substantial sequence homology with the nucleotide sequence shown in SEQ ID NO: 1 or encoding proteins having substantial homology to the amino acid sequence shown in SEQ ID NO: 2. Homology refers to sequence similarity between sequences and can be determined by comparing a position in each sequence which may be aligned for purposes of comparison. When a position in the compared sequence is occupied by the same nucleotide base or amino acid, then the molecules are homologous at that position. A degree of homology between sequences is a function of the number of matching or homologous positions shared by the sequences. Examples of sequences having substantial homology to that of SEQ ID NOs: 1 and 2 are naturally-occuring variants thereof from the same species (i.e., humans, from which the nucleic acid of SEQ ID NO: 1 is derived) and homologues from other species (e.g., non-human mammalian forms of MRP). Regarding the former, in one embodiment the invention provides a natural human MRP variant having the nucleotide and encoded amino-acid sequences shown in SEQ ID NOs: 3 and 4, respectively. This variant differs from in nucleotide sequence from that of SEQ ID NO: 1 at three nucleotide positions: 2249 (a change from T to C), 4039 ( a change from C to G) and 4040 (a change from G to C). These nucleotide changes in this human variant lead to two changes in the amino acid sequence of the encoded MRP protein, one at position 685 ( a change from a Leu to a Ser) and the other at position 1282 (a change from an Arg to an Ala). Regarding species homologues of the human MRP sequence of SEQ ID NO: 1, in another embodiment the invention provides a murine nucleic acid molecule encoding a murine MRP. The nucleotide sequence and encoded amino acid sequence of a murine MRP cDNA is shown in SEQ ID NOs: 5 and 6, respectively. The human and murine MRP proteins exhibit 88% amino acid identity. The strongest conservation between the two protein is within a stretch of amino acid residues located at positions 1126 to 1239 of the human MRP protein and positions 1123 to 1236 of the mouse MRP protein.

The term "sequences having substantial sequence homology" means those nucleotide and amino acid sequences which have slight or inconsequential sequence variations from the sequences disclosed in SEQ ID NO: 1 and SEQ ID NO: 2, i.e. the homologous nucleic acids function in substantially the same manner to produce substantially the same polypeptides as the actual sequences. The variations may be attributable to local mutations or structural modifications. It is expected that substitutions or alterations can be made in various regions of the nucleotide or amino acid sequence without affecting protein function, particularly if they lie outside the regions predicted to be of functional significance.

Analysis of the protein encoded by SEQ ID NO: 1, comprising the amino acid sequence of SEQ ID NO: 2, reveals 12 hydrophobic stretches predicted to be membrane-spanning regions and of functional importance. These amino acid residues correspond to positions 99–115, 137–153, 175–191, 365–381, 444–460, 466–482, 555–571, 591–607, 969–985, 1028–1044, 1102–1118 and 1205–1221 of SEQ ID NO: 2. Nucleotide substitutions that result in amino acid sequence changes within these regions, especially those that reduce the hydrophobic nature of these regions, are not likely to be translated into a functional protein.

Analysis of the protein encoded by SEQ ID NO: 1, comprising the amino acid sequence of SEQ ID NO: 2, reveals two regions having the structural characteristics of nucleotide binding folds (NBFs) typical of ATP-binding cassette domains (ABC domains). See Hyde, S. C. et al., *Nature* 346, 362–365 (1990). Elements comprising part of the structure of these NBFs are conserved in other members of the ABC superfamily of membrane transport proteins and the domains have been shown to bind nucleotides and to be functionally important. For example see Higgins, C. F., *Ann. Rev. Cell Biol.* 8, 67–113 (1992). In the protein comprising the amino acid sequence shown in SEQ ID NO: 2, the two NBFs are located between about amino acid residues 661–810 and 1310–1469 of SEQ ID NO: 2. Nucleotide and corresponding amino acid substitutions which decrease the degree of homology of these regions compared to other members of the ABC superfamily of membrane transport proteins are likely not to be tolerated in a functional protein. Alternatively, nucleotide and corresponding amino acid substitutions which maintain the structure of an NBF are likely to be tolerated. For example, it has been demonstrated that nucleotides encoding an NBF of one member of the ABC superfamily of membrane transport proteins can be substituted for the homologous domain of another member while maintaining function of the protein. See Buschman, F. and Gros, P. *Mol. Cell. Biol.* 11, 595–603 (1991). Accordingly, the invention provides for a nucleic acid encoding a protein comprising an amino acid sequence represented by V-W-X-Y-Z, wherein V are amino acid residues corresponding to amino acid residues from about 1 to 660 of SEQ ID NO: 2, W are amino acid residues of an NBF substantially homologous with amino acid residues from about 661 to 810 of SEQ ID NO: 2, X are amino acid residues corresponding to amino acid residues from about 811 to 1309 of SEQ ID NO: 2, Y are amino acid residues of an NBF substantially homologous with amino acid residues from about 1310 to 1469 of SEQ ID NO: 2 and Z are amino acid residues corresponding to amino acid residues from about 1470 to 1531 of SEQ ID NO: 2. The term "from about" is intended to mean that the junction between two regions of the protein (e.g. between V and W) may vary by a few amino acids from those specifically indicated.

It is anticipated that, outside of the regions specified above, a nucleic acid encoding a protein comprising an amino acid sequence which is about 50% similar with the amino acid sequence shown SEQ ID NO: 2 will provide functional proteins. Alternatively, proteins comprising an amino acid sequence which is 60%, 70%, 80% or 90% homologous with the amino acid sequence shown SEQ ID NO: 2 may provide proteins having MRP activity. The invention encompasses a nucleic acid encoding a protein having biological activity of MRP which is at least 50% homologous with the amino acid sequence of SEQ ID NO: 2. Specific examples of such additional nucleic acid molecules encoded by the invention include the human MRP variant shown in SEQ ID NOs: 3 (which differs in nucleotide sequence from that of SEQ ID NO: 1 by only three nucleotide base pairs) and the mouse MRP cDNA shown in SEQ ID: 5 (which encodes a mouse MRP protein, shown in SEQ ID NO: 6, which is 88% identical in amino acid sequence to the human MRP protein of SEQ ID NO: 2).

It will further be appreciated that variant forms of the nucleic acids of the invention which arise by alternative splicing of an mRNA corresponding to a cDNA of the invention are encompassed by the invention. Hybridization of a cDNA of the invention, containing all or part of SEQ ID NO: 1, to cellular RNA identifies an mRNA of approximately 6.5 kb with an extended open reading frame of 1531 amino acids. Several cDNA clones have been isolated that contain internal deletions which maintain the original reading frame, suggesting that they may be produced by alternative splicing. The existence of mRNA species containing these deletions was confirmed by reverse PCR of RNA from both multidrug resistant and sensitive cells. In most cases, the variant mRNAs represent minor components of 10% or less. However, some comprise more than 20% of total MRP mRNA. Alternative splice forms have been identified which remove nucleotides 657 to 783 of SEQ ID NO: 1 (amino acids 155–196 inclusive of SEQ ID NO: 2), 1845 to 1992 (amino acids 551–599 inclusive), 2287 to 2463 (amino acids 698–756 inclusive), 2287 to 2628 (amino acids 698–811 inclusive) and 4230 to about 4818 (amino acids 1346 to 1531 inclusive). Two of the more common variants lack segments of the $NH_2$ proximal NBF. Both begin at the same site (amino acid 698) and they affect regions of the cassette that are very near and COOH proximal to the common exon 9 splicing variant of the cystic fibrosis transmembrane conductance regulator (CFTR) mRNA. See Chu, C.-S. et al., *EMBO Journal* 10, 1355–1363 (1991). The shorter of the two (amino acids 698–756) eliminates a phenylalanine at a position corresponding to F508 of CFTR. The longer one (amino acids 698–811) removes the active transport family signature that includes the conserved LSGGQ sequence and the Walker B motif. Another of the more common variants (amino acids 1346–1531) lacks a region specifying a segment of the protein close to the COOH terminus, similar to the location affected by alternative splicing of exon 23 of CFTR mRNA. See Yoshimura. K., et al. *J. Biol. Chem.* 268, 686–690 (1993). In addition, two other deletions have been identified, one of which eliminates two of the transmembrane domains in the NH2 proximal half of the molecule (amino acids 551–599), and another which removes a potential secretory signal cleavage site located between amino acids 189/190 (amino acids 155–196).

Another aspect of the invention provides a nucleic acid which hybridizes under high or low stringency conditions to a nucleic acid which encodes a protein having all or a portion of an amino acid sequence shown SEQ ID NO: 2. Appropriate stringency conditions which promote DNA hybridization, for example, 6.0× sodium chloride/sodium citrate (SSC) at about 45° C., followed by a wash of 2.0× SSC at 50° C. are known to those skilled in the art or can be found in *Current Protocols in Molecular Biology,* John Wiley & Sons, N.Y. (1989), 6.3.1–6.3.6. For example, the salt concentration in the wash step can be selected from a low stringency of about 2.0× SSC at 50° C. to a high stringency of about 0.2× SSC at 50° C. In addition, the temperature in the wash step can be increased from low stringency conditions at room temperature, about 22° C. to high stringency conditions, at about 65° C.

Isolated nucleic acids encoding a protein having the biological activity of MRP, as described herein, and having a sequence which differs from a nucleotide sequence shown in SEQ ID NO: 1 due to degeneracy in the genetic code are also within the scope of the invention. Such nucleic acids encode functionally equivalent proteins (e.g., a protein having MRP activity) but differ in sequence from the sequence of SEQ ID NO: 1 due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of an MRP protein (especially those within the third base of a codon) may result in "silent" mutations in the DNA which do not affect the amino acid encoded. However, it is expected that DNA sequence polymorphisms that do lead to changes in the amino acid sequences of an MRP protein will exist within a population. It will be appreciated by one skilled in the art that these variations in one or more nucleotides (up to about 3–4% of the nucleotides) of the nucleic acids encoding proteins having the biological activity of MRP may exist among individuals within a population due to natural allelic variation. Any and all such nucleotide variations and resulting amino acid polymorphisms are within the scope of the invention. Furthermore, there may be one or more isoforms or related, cross-reacting family members of MRP described herein. Such isoforms or family members are defined as proteins related in biological activity and amino acid sequence to MRP, but encoded by genes at different loci.

An isolated nucleic acid of the present invention encoding a protein having the biological activity of MRP can be isolated from a multidrug resistant cell line which displays resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. One example of such a cell line is H69AR. Other suitable cell lines can be produced by stepwise selection of a non-resistant cell line in the presence of increasing concentrations of a drug for which resistance is to be acquired over a period of several months to years. For example, a cell line is cultured in the presence of an anthracycline, preferably doxorubicin, for about 14 months. Multidrug resistance is then assessed by exposing the selected cell line to other drugs, e.g. an epipodo-phyllotoxin such as VP-16 and a Vinca alkaloid such as vincristine, and determining the cytotoxicity of the drug for the cell line. The ability of chemosensitizers which reverse P-glycoprotein-mediated multidrug resistance, such as verapamil and cyclosporin A, to reverse the multidrug resistance is then assessed by exposing the selected cell line to these agents in the presence of the resistant drugs. A detailed description of the procedures which can be used to produce appropriate multidrug resistant cell line such as H69AR is found in Cole, *Cancer Chemother Pharmacol.* 17, 259–263 (1986), Mirski et al., *Cancer Research* 47, 2594–2598 (1987) and Cole, et al. *British J. Cancer* 2:42–46 (1989).

An appropriate multidrug resistant cell line (e.g. a multidrug resistant cell line which displays resistance to anthracyclines, epipodophyllotoxins and Vinca alkaloids that is not substantially reversed by verapamil or cyclosporin A) is used to isolate a nucleic acid of the invention by preparing a cDNA library from this cell line by standard techniques and screening this library with cDNA produced from total mRNA isolated from the multidrug resistant cell line and its drug sensitive parental cell line. For example, a cDNA library constructed from total mRNA from H69AR cells is prepared. The library is plated and two sets of replica filters are prepared by standard methods. One set of filters is then screened with cDNA prepared from H69AR mRNA and the other set of filters is screened with a comparable amount of cDNA prepared from H69 mRNA. The cDNA used for screening the library is labelled, typically with a radioactive label. Following visualization of the hybridization results by standard procedures, cDNA clones displaying increased hybridization with H69AR cDNA when compared to H69 cDNA can be selected from the library. These cDNAs are derived from mRNAs overexpressed in H69AR cells when compared with H69 cells. For descriptions of differential cDNA library screening see King, C. R., et al. *J. Biol. Chem.* 254, 6781 (1979); Van der Bliek, A. M., et al., *Mol. Cell. Biol.* 6, 1671 (1986).

Determination of whether a cDNA so isolated has the biological activity of MRP can be accomplished by expressing the cDNA in a nonresistant mammalian cell, by standard techniques, and assessing whether expression in the cell of the protein encoded by the cDNA confers on the cell multidrug resistance to anthracyclines, epipodophyllotoxins and Vinca alkaloids that is not substantially reversed by verapamil or cyclosporin A. A cDNA having the biological activity of MRP so isolated can be sequenced by standard techniques, such as dideoxynucleotide chain termination or Maxam-Gilbert chemical sequencing, to determine the nucleic acid sequence and the predicted amino acid sequence of the encoded protein.

An isolated nucleic acid of the invention which is DNA can also be isolated by preparing a labelled nucleic acid probe encompassing all or part of the nucleotide sequence shown in SEQ ID NO: 1 and using this labelled nucleic acid probe to screen an appropriate DNA library (e.g. a cDNA or genomic DNA library). For instance, a cDNA library made from a multi-drug resistant cell line as described above can be used to isolate a cDNA encoding a protein having MRP activity by screening the library with the labelled probe using standard techniques. Preferably, an H69AR cDNA library is used. Alternatively, a genomic DNA library can be similarly screened to isolate a genomic clone encompassing a gene encoding a protein having MRP activity. As demonstrated in Example 4, a human MRP gene has been mapped to chromosome 16. Therefore, a chromosome 16 library rather than a total genomic DNA library can also be used to isolate a human MRP gene. Nucleic acids isolated by screening of a cDNA or genomic DNA library can be sequenced by standard techniques.

An isolated nucleic acid of the invention which is DNA can also be isolated by selectively amplifying a nucleic acid encoding a protein having MRP activity using the polymerase chain reaction (PCR) method and genomic DNA or mRNA. To prepare cDNA from mRNA, total cellular mRNA can be isolated, for instance from a multidrug resistant cell line, by a variety of techniques, e.g., by using the guanidinium-thiocyanate extraction procedure of Chirgwin et al., *Biochemistry*, 18, 5294–5299 (1979). cDNA is then synthesized from the mRNA using reverse transcriptase. Moloney MLV reverse transcriptase available from Gibco/ BRL, Bethesda, Md., or AMV reverse transcriptase available from Seikagaku America, Inc., St. Petersburg, Fla., are preferably employed. It is possible to design synthetic oligonucleotide primers from the nucleotide sequence shown in SEQ ID NO: 1 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis.

A isolated nucleic acid of the invention which is RNA can be isolated by cloning a cDNA of the invention into an appropriate vector which allows for transcription of the cDNA to produce an RNA molecule which encodes a protein having MRP activity. For example, a cDNA can be cloned downstream of a bacteriophage promoter, e.g. a T7 promoter, in a vector and the cDNA can be transcribed in vitro with T7 polymerase. A resultant RNA can be isolated by standard techniques.

A nucleic acid of the invention, for instance an oligonucleotide, can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Analysis of the nucleotide sequence of SEQ ID NO: 1 using currently available computer software designed for the purpose, such as PC/Gene—IntelliGenetics Inc., Calif., permits the identification of the initiation codon and untranslated sequences of an MRP cDNA. The cDNA coding strand, depicted as SEQ ID NO: 1, contains a 4593 nucleotide open reading frame encoding 1531 amino acids, as well as 195 5' untranslated nucleotides and 223 3' untranslated nucleotides. The intron-exon structure and the transcription regulatory sequences of the gene encoding the MRP cDNA can be identified by using a nucleic acid of the invention to probe a genomic DNA clone library. Regulatory elements, such as promoter and enhancers necessary for expression of the gene encoding the MRP in various tissues, can be identified using conventional techniques. The function of the elements can be confirmed by using them to express a reporter gene such as the bacterial gene lacZ which is operatively linked to the fragments. Such a construct can be introduced into cultured cells using standard procedures or into non-human transgenic animal models. In addition to identifying regulatory elements in DNA, such constructs can also be used to identify nuclear proteins interacting with said elements, using techniques known in the art.

A number of unique restriction sites for restriction enzymes are present in the nucleic acid comprising the nucleotide sequence shown in SEQ ID NO: 1 These restriction sites provide access to nucleotide fragments which code for polypeptides unique to the protein encoded by SEQ ID NO: 1 (i.e. a protein of the invention).

The isolated nucleic acids of the invention or oligonucleotide fragments of the isolated nucleic acids, allow those skilled in the art to construct nucleotide probes for use in the detection of nucleotide sequences in biological materials, such as tumor cell samples. A nucleotide probe can be labelled with a radioactive element which provides for an adequate signal as a means for detection and has sufficient half-life to be useful for detection, such as $^{32}$P, $^{3}$H, $^{14}$C or the like. Other materials which can be used to label the probe include antigens that are recognized by a specific labelled antibody, fluorescent compounds, enzymes, antibodies specific for a labelled antigen, and chemiluminescent compounds. An appropriate label can be selected having regard to the rate of hybridization and binding of the probe to the nucleotide to be detected and the amount of nucleotide available for hybridization.

II. Antisense Nucleic Acids

The invention also relates to an antisense nucleic acid, or oligonucleotide fragment thereof, of a nucleic acid of the invention. An antisense nucleic acid can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence found in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO: 1. A nucleic acid is designed which has a sequence complementary to a sequence of the coding or untranslated region of the shown nucleic acid. Alternatively, an antisense nucleic acid can be designed based upon sequences of an MRP gene, identified by screening a genomic library as described above. For example, the sequence of an important regulatory element can be determined as described above and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

III. Recombinant Expression Vectors

The nucleic acids of the present invention which encode proteins having MRP activity can be incorporated in a known manner into a recombinant expression vector which ensures good expression of the encoded protein or part thereof. The recombinant expression vectors are "suitable for transformation of a host cell", which means that the recombinant expression vectors contain a nucleic acid or an oligonucleotide fragment thereof of the invention and a regulatory sequence, selected on the basis of the host cells to be used for expression, which is operatively linked to the nucleic acid or oligonucleotide fragment. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the term regulatory sequence includes promoters, enhancers and other expression control elements. Such regulatory sequences are known to those skilled in the art or one described in Goeddel, *Gene Expression Technology: Methods in Enzymology* 185, Academic Press, San Diego, Calif. (1990) can be used. It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids as described herein.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, Calif. (1990).

Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET 11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector (e.g. a nucleic acid encoding an MRP protein) so that the individual codons for each amino acid would be those preferentially utilized in highly expressed *E. coli* proteins (Wada et al., (1992) *Nuc. Acids Res.* 20:2111–2118). Such alteration of nucleic acid sequences of the invention could be carried out by standard DNA synthesis techniques.

Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 5:113–123), and pYES2 (Invitrogen Corporation, San Diego, Calif.).

Baculovirus vectors available for expression of proteins in cultured insect cells (SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

Expression of an MRP protein in mammalian cells is accomplished using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral material. For example, commonly used promoters are derived from polyoma, Adenovirus 2, cytomegalovirus and most frequently, Simian Virus 40. Preferably, the pRc/CMV expression vector (Invitrogen) is used. In the pRc/CMV vector, nucleic acid introduced into the vector to be expressed is under the control of the enhancer/promoter sequence from the immediate early gene of human cytomegalovirus. Additionally, a gene conferring neomycin resistance is encoded by the vector. In one embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein. For example, a nucleic acid encoding a protein with MRP activity can be preferentially expressed in cardiac muscle cells using promoter and enhancer sequences from a gene which is expressed preferentially in cardiac muscle cells, such as a cardiac myosin gene or a cardiac actin gene.

The recombinant expression vector of the invention can be a plasmid. The recombinant expression vector of the invention further can be a virus, or portion thereof, which allows for expression of a nucleic acid introduced into the viral nucleic acid. For example, replication defective retroviruses, adenoviruses and adeno-associated viruses can be used.

The invention further provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to the nucleotide sequence of SEQ ID NO: 1. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA, as described above.

IV. Transformant Host Cells

The recombinant expression vectors of the invention can be used to make a transformant host cell including the recombinant expression vector. The term "transformant host cell" is intended to include prokaryotic and eukaryotic cell which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (*Molecular Cloning: A Laboratory Manual,* 2nd Edition, Cold Spring Harbor Laboratory press (1989)), and other laboratory textbooks.

The number of host cells transformed with a recombinant expression vector of the invention by techniques such as those described above will depend upon the type of recombinant expression vector used and the type of transformation technique used. Plasmid vectors introduced into mammalian cells are integrated into host cell DNA at only a low frequency. In order to identify these integrants, a gene that contains a selectable marker (i.e., resistance to antibiotics) is generally introduced into the host cells along with the gene of interest. Preferred selectable markers include those which confer resistance to certain drugs, such as G418 and hygromycin. Selectable markers can be introduced on a separate plasmid from the nucleic acid of interest or, preferably, are introduced on a the same plasmid. Host cells transformed with a one or more recombinant expression vectors containing a nucleic acid of the invention and a gene for a selectable marker can be identified by selecting for cells using the selectable marker. For example, if the selectable marker encoded a gene conferring neomycin resistance (such as pRc/CMV), transformant cells can be selected with G418. Cells that have incorporated the selectable marker gene will survive, while the other cells die.

As demonstrated in Examples 5 and 6, the nucleic acids of the invention can confer multidrug resistance to drugs including anthracyclines, epipodophyllotoxins and Vinca alkaloids on a drug sensitive cell when transfected into the cell. Thus, these drugs can be used as selecting agents when preparing a transformant host cell rather than using an independent selectable marker (such as neomycin resistance). Therefore, the nucleic acids of the invention are useful not only for conferring multidrug resistance on a cell but also as selectable markers for cells into which the nucleic acid has been introduced. See for example Pastan et al. U.S. Pat. No. 5,166,059; Croop et al. U.S. Pat. No. 5,198,344. Cells are selected by exposure to one or more drugs for which resistance is conferred by the nucleic acid. An MRP-encoding nucleic acid in a recombinant expression vector can be introduced into a cell together with a second nucleic acid comprising a gene of interest, either in the same vector or in separate vectors, and transformant cells can be selected based upon their acquired drug resistance. Drug resistant cells which are selected will contain the MRP-encoding nucleic acid often cointegrated with the gene of interest. Furthermore, by increasing stepwise the concentration of drug used in selecting the cells, it is possible to obtain transformant cells with a higher number of copies of the introduced nucleic acid, including both the MRP-encoding nucleic acid and a gene of interest. Therefore, the nucleic acids of the invention are also useful as amplifiable markers.

The nucleic acids of the invention encode proteins "having biological activity of MRP". The biological activity of MRP is defined as the ability of the protein, when expressed in a drug sensitive mammalian cell, to confer on the cell multidrug resistance to such drugs as anthracyclines, epipodophyllotoxins and Vinca alkaloids that is not substantially reversed by chemosensitizers which reverse P-glycoprotein-mediated multidrug resistance, such as verapamil or cyclosporin A. An isolated nucleic acid of the invention can be tested for MRP activity by incorporating the nucleic acid into a recombinant expression vector of the invention, transforming a drug sensitive mammalian cell with the recombinant expression vector to make a transformant host cell of the invention as described above and testing the multidrug resistance of the transformant host cell. The multidrug resistance of the transformant host cell is tested by determining the cytotoxicity of the drugs to be tested (i.e. anthracyclines, epipodophyllotoxins and Vinca alkaloids) for the transformed cell as compared to the untransformed cell, and the ability of other drugs (i.e. verapamil and cyclosporin A) to reverse multidrug resistance. For example, in a preferred embodiment, the transformant host cell is a HeLa cell, and the multidrug resistance of transfected HeLa cells is compared to that of untransfected HeLa cells or preferably to HeLa cells transfected with the parental expression vector lacking the nucleic acid encoding a protein having MRP activity.

V. Isolated Proteins

The invention provides isolated proteins having biological activity of MRP. The term "isolated" refers to a protein substantially free of cellular material or culture medium when produced by recombinant DNA techniques, or chemical precursors or other chemicals when chemically synthesized. In a preferred embodiment the protein having biological activity of MRP comprises an amino acid sequence shown in SEQ ID NO: 2. Alternatively, the protein can be encoded by a nucleic acid comprising the nucleotide sequence of SEQ ID NO: 1. Proteins having biological activity of MRP which have substantial sequence homology to the amino acid sequence of SEQ ID NO: 2, as defined above, are also encompassed by the invention. Furthermore, proteins having biological activity of MRP that are encoded by nucleic acids which hybridize under high or low stringency conditions, as defined above, to a nucleic acid comprising a nucleotide sequence shown in SEQ ID NO: 1 are encompassed by the invention. Additionally, immunogenic portions of MRP proteins are within the scope of the invention. As demonstrated in Example 7, two immunogenic portions of a protein comprising an amino acid sequence shown in SEQ ID NO: 2 correspond to amino acid residues 932–943 shown in SEQ ID NO: 2 (residues AELQKAEAKKEE) and amino acid residues 1427–1441 (residues GENLSVGQRQLVCLA). Two other immunogenic portions correspond to amino acid residues 243–252 shown in SEQ ID NO: 2 (residues SLNKEDTSEQ) and amino acid residues 765–779 (residues GVNLSGGQKQRVSLA). Preferred immunogenic portions correspond to regions of the protein not conserved in other ABC superfamily members, i.e. outside of the two NBF domains (amino acid residues 661–810 and 1310–1469), and include regions between the 12 membrane spanning regions. An immunogenic portion will be of at least about eight amino acids in length. See Alnquist et al. *Cancer Research* 55:102–110 (1995).

The MRP protein, or isoforms or parts thereof, of the invention can be isolated by expression in a suitable host cell using techniques known in the art. Suitable host cells include prokaryotic or eukaryotic organisms or cell lines, for example, yeast, *E. coli* and insect cells. The recombinant expression vectors of the invention, described above, can be used to express a protein having MRP activity in a host cell in order to isolate the protein. The invention provides a method of preparing an isolated protein of the invention comprising introducing into a host cell a recombinant nucleic acid encoding the protein, allowing the protein to be expressed in the host cell and isolating the protein. Preferably, the recombinant nucleic acid is a recombinant expression vector. Proteins can be isolated from a host cell expressing the protein according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22, 233–577 (1971)).

Alternatively, the protein or parts thereof can be prepared by chemical synthesis using techniques well known in the chemistry of proteins such as solid phase synthesis (Merrifield, 1964, J. Am. Chem. Assoc. 85:2149–2154) or synthesis in homogeneous solution (Houbenweyl, 1987, Methods of Organic Chemistry, ed. E. Wansch, Vol. 15 I and II, Thieme, Stuttgart).

VI. Antibodies

The proteins of the invention, or portions thereof, can be used to prepare antibodies specific for the proteins. Antibodies can be prepared which bind a distinct epitope in an unconserved region of the protein. An unconserved region of the protein is one which does not have substantial sequence homology to other proteins, for example other members of the ABC superfamily of membrane transport proteins. For example, unconserved regions encompassing sequences between the twelve membrane spanning regions, excluding the NBF domains, can be used. Alternatively, a region from one of the two NBF domains can be used to prepare an antibody to a conserved region of an MRP protein. An antibody to a conserved region may be capable of reacting with other members of the ABC family of membrane transport proteins. Conventional methods can be used to prepare the antibodies. For example, by using a peptide of an MRP protein, polyclonal antisera and monoclonal antibodies can be made using standard methods. As demonstrated in Example 7, a mammal, (e.g., a mouse, hamster, or rabbit) can be immunized with an immunogenic form of the peptide which elicits an antibody response in the mammal. Alternatively, polyclonal antisera and monoclonal antibodies can made by immunizing an animal with a cell which expresses MRP or by immunizing with a membrane fraction of an MRP expressing cell. As demonstrated in Example 8, a mammal (e.g., a mouse, hamster, or rabbit) can be immunized with enriched membrane fractions of the H69AR cell line to elicit a polyclonal antibody response against antigens expressed by the membrane fractions, including MRP. Monoclonal antibodies can then be made by conventional techniques and a monoclonal antibody specific for an MRP protein can be selected, as described further in Example 8.

Two hybridomas, designated QCRL-1 and QCRL-3, producing monoclonal antibodies QCRL-1 and QCRL-3 described in further detail in Example 8, have been deposited with the American Type Culture Collection on Nov. 30, 1994, under the provisions of the Budapest Treaty and have been assigned accession numbers HB 11765 and HB 11766, respectively.

To generate suitable anti-MRP antibodies, the immunogen should contain an effective, immunogenic amount of an MRP peptide or protein, e.g., as a membrane-bound protein, isolated protein, recombinantly produced protein, synthetic peptide, or other suitable form of the immunogen. The immunogen can optionally be used as a conjugate linked to a carrier. The effective amount of immunogen per unit dose depends, among other things, on the species of animal inoculated, the body weight of the animal and the chosen immunization regimen, as is well known in the art. An immunization preparation can also include an adjuvant as part of the diluent. Adjuvants such as complete Freund's adjuvant (CFA), incomplete Freund's adjuvant (IFA) and alum are materials well known in the art, and are available commercially from several sources. Techniques for conferring immunogenicity on a peptide include conjugation to a carrier. The progress of immunization can be monitored by detection of antibody titers in plasma or serum. Standard ELISA or other immunoassay can be used with the immunogen as antigen to assess the level of antibody titers. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* 256, 495–497 (1975)) as well as other techniques such as the human B-cell hybridoma technique (Kozbor et al., *Immunol. Today* 4, 72 (1983)), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* 246, 1275 (1989)). Hybridoma cells can be screened immunochemically for production of antibodies specifically reactive with an MRP protein or peptide and monoclonal antibodies isolated by standard techniques (see Example 8).

The term antibody as used herein is intended to include fragments thereof which are also specifically reactive with a protein, or peptide thereof, having the biological activity of MRP. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing an immunoglobulin variable region which recognizes an MRP protein of the invention. See, for example, Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a protein, or peptide thereof, having the biological activity of a MRP as described herein can be further humanized by producing human variable region chimeras, in which parts of the variable regions, especially the conserved framework regions of the antigen-binding domain, are of human origin and only the hypervariable regions are of non-human origin. Such altered immunoglobulin molecules, referred to herein as "humanized" antibodies, may be made by any of several techniques known in the art, (e.g., Teng et al., *Proc. Natl. Acad. Sci. U.S.A.*, 80, 7308–7312 (1983); Kozbor et al., *Immunology Today*, 4, 7279 (1983); Olsson et al., *Meth. Enzymol.*, 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

Another method of generating specific antibodies, or antibody fragments, reactive against protein, or peptide thereof, having the biological activity of a MRP is to screen expression libraries encoding immunoglobulin genes, or portions thereof, expressed in bacteria with peptides produced from the nucleic acid molecules of the present invention. For example, complete Fab fragments, $V_H$ regions, $V_L$ regions, and $F_V$ regions can be expressed in bacteria using phage expression libraries. See for example Ward et al., *Nature* 341, 544–546: (1989); Huse et al., *Science* 246, 1275–1281 (1989); and McCafferty et al. *Nature* 348, 552–554 (1990). To identify an anti-MRP antibody, or antibody fragment, such libraries can be screened with an MRP protein of the invention, or peptide thereof. Alternatively, the SCID-hu mouse available from Genpharm can be used to produce antibodies, or fragments thereof.

The polyclonal, monoclonal or chimeric monoclonal antibodies can be used to detect the proteins of the invention, portions thereof or closely related isoforms in various biological materials, for example they can be used in an ELISA, radioimmunoassay or histochemical tests. Thus, the antibodies can be used to quantify the amount of an MRP protein of the invention, portions thereof or closely related isoforms in a sample in order to diagnose multidrug resistance, and to determine the role of MRP proteins in particular cellular events or pathological states, particularly its role in multidrug resistance. Using methods described hereinbefore, polyclonal, monoclonal antibodies, or chimeric monoclonal antibodies can be raised to nonconserved regions of MRP and used to distinguish MRP from closely related isoforms and other proteins that share a common conserved epitope.

The polyclonal or monoclonal antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic-group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{13}I$, $^{35}S$ or $^3H$.

The present invention allows the skilled artisan to prepare bispecific antibodies and tetrameric antibody complexes. Bispecific antibodies can be prepared by forming hybrid hybridomas. The hybrid hybridomas can be prepared using the procedures known in the art such as those disclosed in Staerz & Bevan, (PNAS (USA) 83: 1453, 1986 and Immunology Today, 7:241, 1986). In general, a hybrid hybridoma is formed by fusing a first cell line which produces a first monoclonal antibody which is capable of binding to a tumor cell expressing a protein of the invention and a second cell line which produces a second monoclonal antibody which is capable of binding to a detectable substance, or a substance having toxic or therapeutic activity. The bispecific antibodies can also be constructed by chemical means using procedures such as those described by Staerz et al., (Nature, 314:628, 1985) and Perez et al., (Nature 316:354, 1985).

Bispecific monoclonal antibodies containing a variable region of an antibody, preferably a human antibody, specific for an MRP protein of the invention or portion thereof, a variable region of an antibody which is capable of binding to a detectable substance, or a substance having toxic or therapeutic activity and the constant regions of human immunoglobulins such as human IgG1, IgG2, IgG3 and IgG4 can also be constructed as described above. Bispecific chimeric monoclonal antibodies can also be constructed as described above.

A tetrameric antibody complex can be prepared by preparing a first monoclonal antibody which is capable of binding to a tumor cell expressing a protein of the invention and a second monoclonal antibody which is capable of binding to a detectable substance or a substance having toxic or therapeutic activity. The first and second antibody are from a first animal species. The first and second antibody are reacted with an about equimolar amount of antibodies of a second animal species or Fab fragments thereof, which are directed against the Fc-fragments of the antibodies of the first animal species. The tetrameric complex formed is then isolated. (See U.S. Pat. No. 4,868,109 to Lansdorp for a description of methods for preparing tetrameric antibody complexes).

Examples of detectable substances are enzymes, such as horseradish peroxidase, alkaline phosphatase, glucose oxidase and galactosidase. Examples of substances having toxic activity are cytotoxic cells such as macrophages, neutrophils, eosinophils, NK cells, LAK cells, and large granular lymphocytes or substances which are toxic to tumor cells such as radionuclides, and toxins such as diptheria toxin and ricin or attenuated derivatives thereof. It will be appreciated that the antibody can be directed against the Fc receptor on cytotoxic cells. Examples of substances having therapeutic activity are chemotherapeutic agents such as carboplatin and methotrexate. Preferably, the chemotherapeutic agent is not a drug to which a protein having MRP activity confers resistance.

The antibodies, bispecific antibodies and tetrameric antibody complexes of the invention directed against a protein having MRP activity, optionally coupled with a substance having toxic or therapeutic activity, can be used to treat multidrug resistant tumors. Accordingly, the invention provides a composition comprising antibodies, bispecific antibodies or tetrameric antibody complexes in a pharmaceutically acceptable carrier. Preferably, the antibodies, bispecific antibodies or tetrameric antibody complexes are coupled to or capable of binding to a substance having toxic or therapeutic activity and to a tumor cell expressing a protein of the invention.

The compositions of the invention are administered to subjects in a biologically compatible form suitable for pharmaceutical administration in vivo. By "biologically compatible form suitable for administration in vivo" is meant a form of the antibody to be administered in which any toxic effects are outweighed by the therapeutic effects of the antibody. The term subject is intended to include living organisms in which an immune response can be elicited, e.g., mammals. Examples of subjects include humans, dogs, cats, mice, rats, and transgenic species thereof. Administration of a therapeutically active amount of the therapeutic compositions of the present invention is defined as an amount effective, at dosages and for periods of time necessary to achieve the desired result. For example, a therapeutically active amount of an antibody reactive with an MRP protein of the invention may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

An antibody composition can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. To administer an antibody reactive with an MRP protein by other than parenteral administration, it may be necessary to coat the antibody with, or co-administer the antibody with, a material to prevent its inactivation. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., antibody reactive against an MRP protein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

VII. Transgenic and Knockout Animals

Nucleic acids which encode proteins having biological activity of MRP can be used to generate either transgenic animals or "knock out" animals which, in turn, are useful in the development and screening of therapeutically useful reagents. A transgenic animal (e.g., a mouse) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, a human MRP cDNA, comprising the nucleotide sequence shown in SEQ ID NO: 1, or an appropriate sequence thereof, can be used to clone a murine MRP gene in accordance with established techniques and the genomic nucleic acid used to generate transgenic animals that contain cells which express MRP protein. Methods for generating transgenic animals, particularly animals such as mice, have become conventional in the art and are described, for example, in U.S. Pat. Nos. 4,736,866 and 4,870,009. In a preferred embodiment, plasmids containing recombinant molecules of the invention are microinjected into mouse embryos. In particular, the plasmids are microinjected into the male pronuclei of fertilized one-cell mouse eggs; the injected eggs are transferred to pseudo-pregnant foster females; and, the eggs in the foster females are allowed to develop to term. [Hogan, B. et al., (1986) A Laboratory Manual, Cold Spring Harbor, New York, Cold Spring Harbor Laboratory].

Alternatively, an embryonal stem cell line can be transfected with an expression vector containing nucleic acid encoding a protein having MRP activity and cells containing the nucleic acid can be used to form aggregation chimeras with embryos from a suitable recipient mouse strain. The chimeric embryos can then be implanted into a suitable pseudopregnant female mouse of the appropriate strain and the embryo brought to term. Progeny harbouring the transfected DNA in their germ cells can be used to breed uniformly transgenic mice.

Typically, particular cells would be targeted for MRP transgene incorporation by use of tissue specific enhancers operatively linked to the MRP-encoding gene. For example, promoters and/or enhancers which direct expression of a gene to which they are operatively linked preferentially in cardiac muscle cells can be used to create a transgenic animal which expresses an MRP protein preferentially in cardiac muscle tissue. Examples of suitable promoters and enhancers include those which regulate the expression of the genes for cardiac myosin and cardiac actin. Transgenic animals that include a copy of an MRP transgene introduced into the germ line of the animal at an embryonic stage can also be used to examine the effect of increased MRP expression in various tissues.

The pattern and extent of expression of a recombinant molecule of the invention in a transgenic mouse is facilitated by fusing a reporter gene to the recombinant molecule such that both genes are co-transcribed to form a polycistronic mRNA. The reporter gene can be introduced into the recombinant molecule using conventional methods such as those described in Sambrook et al., 1989, Molecular Cloning, A Laboratory Manual. Cold Spring Harbor Laboratory Press. Efficient expression of both cistrons of the polycistronic mRNA encoding the protein of the invention and the reporter protein can be achieved by inclusion of a known internal translational initiation sequence such as that present in poliovirus mRNA. The reporter gene should be under the control of the regulatory sequence of the recombinant molecule of the invention and the pattern and extent of expression of the gene encoding a protein of the invention can accordingly be determined by assaying for the phenotype of the reporter gene. Preferably the reporter gene codes for a phenotype not displayed by the host cell and the phenotype can be assayed quantitatively. Examples of suitable reporter genes include lacZ (B-galactosidase), neo (neomycin phosphotransferase), CAT (chloramphenicol acetyltransferase) dhfr (dihydrofolate reductase), aphIV (hygromycin phosphotransferase), lux (luciferase), uidA (B-glucuronidase). Preferably, the reporter gene is lacZ which codes for B-galactosidase. B-galactosidase can be assayed using the lactose analogue X-gal(5-bromo-4-chloro-3-indolyl-b-D-galactopyranoside) which is broken down by B-galactosidase to a product that is blue in color. (See for example Old R. W. & Primrose S. B., Principles of Gene Manipulation. An Introduction to Genetic Engineering, 4th ed. Oxford University Press at pages 63–66 for a discussion of procedures for screening for recombinants).

Although experimental animals used in the preferred embodiment disclosed are mice, the invention should not be limited thereto. It can be desirable to use other species such as rats, hamsters and rabbits.

The transgenic animals of the invention can be used to investigate the molecular basis of multidrug resistance. The transgenic animals of the invention can also be used to test substances for the ability to prevent, slow or reverse the development of multidrug resistance. A transgenic animal can be treated with the substance in parallel with an untreated control transgenic animal.

Cells from the transgenic animals of the invention can be cultured using standard tissue culture techniques. In particular, cells carrying the recombinant molecule of the invention can be cultured and used to test substances for the ability to prevent, slow or reverse multidrug resistance.

Additionally, the non-human homologues of genes encoding proteins having MRP activity can be used to construct an MRP "knock out" animal which has a defective or altered MRP gene. For example, a human MRP cDNA, comprising the nucleotide sequence shown in SEQ ID NO: 1, or an appropriate sequence thereof, can be used to clone a murine MRP gene in accordance with established techniques. A portion of the isolated genomic MRP DNA (e.g., an exon) can be deleted or replaced with another gene, such as a gene encoding a selectable marker which can be used to monitor integration. The altered MRP DNA can then be transfected into an embryonal stem cell line. The altered MRP DNA will homologously recombine with the endogenous MRP gene in certain cells and clones containing the altered gene can be selected. Cells containing the altered gene are injected into a blastocyst of an animal, such as a mouse, to form aggregation chimeras as described for transgenic animals. Chimeric embryos are implanted as described above. Transmission of the altered gene into the germline of a resultant animal can be confirmed using standard techniques and the animal can be used to breed animals having an altered MRP gene in every cell. Accordingly, a knockout animal can be made which cannot express a functional MRP protein. Such a knockout animal can be used, for example, to test the effectiveness of a chemotherapeutic agent in the absence of an MRP multidrug resistance protein.

VIII. Uses of the Invention

The isolated nucleic acids of the invention are useful as molecular probes for use diagnostically to determine multidrug resistance of a tumor. As demonstrated in Example 1, multidrug resistance of certain tumor cell lines is associated with increased expression of cellular mRNA corresponding to the nucleotide sequence of SEQ ID NO: 1. Accordingly, the nucleic acids of the invention can be labelled with a detectable marker, such as a radioactive, fluorescent or biotinylated marker, and used in conventional dot blot, Northern hybridization or in situ hybridization procedures to probe mRNA molecules of total cellular or poly(A)+ RNAs from a biological sample, for instance cells of a tumor biopsy.

The nucleic acid probes can be used to detect genes, preferably in human cells, that encode proteins related to or analogous to the MRP of the invention. Preferably, nucleic acid comprising the nucleotide sequence of the invention, or a segment thereof, can be used as a probe to identify DNA fragments comprising genes or parts of genes that are co-amplified with the gene of the invention and which reside within the same amplification unit, or amplicon, at the chromosomal location 16p13.1. More specifically a nucleic acid of the invention can be used as a probe to screen human genomic DNA libraries constructed in cosmid or yeast artificial chromosome vectors, using procedures standard in the art, to define a contiguous segment of DNA that comprises the amplification unit detected in a multidrug resistant cell line such as H69AR. In this manner additional genes can be identified which also confer or contribute to the multidrug resistance phenotype of H69AR and other human cell lines yet to be examined but which are known to include the HeLa cell line J2c and HT1080 DR4 cell line.

The antisense nucleic acids of the invention are useful for inhibiting expression of nucleic acids (e.g. mRNAs) encoding proteins having MRP activity, thereby decreasing expression of proteins having MRP activity. Since increased expression of proteins having MRP activity is associated with and can confer multidrug resistance on a cell, decreasing expression of such proteins can inhibit or reverse multidrug resistance of a cell into which the antisense nucleic acid has been introduced. Antisense nucleic acids can be introduced into a multidrug resistant cell in culture to inhibit MRP expression. One or more antisense nucleic acids, such as oligonucleotides, can be added to cells in culture media, typically at 200 µg/ml. A cultured multidrug resistant cell in which MRP expression is inhibited is useful for testing the efficacy of potential therapeutic agents. For example, MRP expression could be inhibited in a tumor cell line which expresses both MRP and P-glycoprotein to determine the contribution of MRP to an observed resistance or sensitivity of the cell to a particular therapeutic agent.

The antisense nucleic acids of the invention, or oligonucleotides thereof, can also be used in gene therapy to correct or prevent multidrug resistance in a subject. For example, antisense sequences can be used to render multidrug resistant malignant cells sensitive to chemotherapeutic agents. Administration of antisense nucleic acids to a subject may be most effective when the antisense nucleic acid is contained in a recombinant expression vector which allows for continuous production of antisense RNA. Recombinant molecules comprising an antisense nucleic acid or oligonucleotides thereof, can be directly introduced into tissues, including lung tissue in vivo, using delivery vehicles such as liposomes, retroviral vectors, adenoviral vectors and DNA virus vectors. A delivery vehicle can be chosen which can be targeted to a cell of interest in the subject (e.g. a multidrug resistant tumor cell). Antisense nucleic acids can also be introduced into isolated cells, such as those of the hematopoietic system, ex vivo using viral vectors or physical techniques such as microinjection and electroporation or chemical methods such as coprecipitation and incorporation of DNA into liposomes and such cells can be returned to the donor. Recombinant molecules can also be delivered in the form of an aerosol or by lavage. In the treatment of lung malignancies, antisense sequences can be directly delivered to lung tissue by an aerosol or by lavage.

Accordingly, the invention provides a method for inhibiting multidrug resistance of a multidrug resistant cell by introducing into the multidrug resistant cell a nucleic acid which is antisense to a nucleic acid which encodes the protein shown in SEQ ID NO: 2.

The nucleic acids of the invention can further be used to design ribozymes which are capable of cleaving a single-stranded nucleic acid encoding a protein having MRP activity, such as an mRNA. A catalytic RNA (ribozyme) having ribonuclease activity can be designed which has specificity for an MRP-encoding mRNA based upon the sequence of a nucleic acid of the invention. For example, a derivative of a Tetrahymena L-19 IVS RNA can be constructed in which the base sequence of the active site is complementary to the base sequence to be cleaved in an MRP-encoding mRNA. See for example Cech et al. U.S. Pat. No. 4,987,071; Cech et al. U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. *Science* 261, 1411–1418 (1993).

The isolated nucleic acids and antisense nucleic acids of the invention can be used to construct recombinant expression vectors as described previously. These recombinant expression vectors are then useful for making transformant host cells containing the recombinant expression vectors, for expressing proteins encoded by the nucleic acids of the invention, and for isolating proteins of the invention as described previously. The isolated nucleic acids and antisense nucleic acids of the invention can also be used to construct transgenic and knockout animals as described previously.

As demonstrated in Examples 5 and 6, a recombinant expression vector containing a nucleic acid of the invention can be used to transfect a drug sensitive cell line to produce a protein in the cell which can confer multidrug resistance on the transfected cell line. Thus, the recombinant expression vectors of the invention are useful for conferring multidrug resistance on a drug sensitive cell. Accordingly, the invention provides a method for protecting a drug sensitive cell from cytotoxicity due to exposure to a drug by transfecting the cell with nucleic acid comprising a nucleotide sequence shown in SEQ ID NO: 1 to confer drug resistance on the cell. In preferred embodiments, the drug sensitive cell is a cardiac muscle cell or a hematopoietic stem cell. The ability to confer drug resistance on a cell has important clinical applications. A major dose-limiting factor for chemotherapeutic agents is their cytotoxicity for normal cells in a patient as well as tumor cells. In patients with multi-drug resistant tumors, increasing the dosage of chemotherapeutic agents is prohibited by the toxicity of these agents for normal cells. In the case of anthracyclines, cardiotoxicity of the drugs can be a major clinical limitation. For chemotherapeutic drugs which target rapidly dividing cells, toxicity to hematopoietic cells can be a major clinical limitation. Additionally, neurotoxicity can occur. Protecting nonresistant nontumor cells from the effects of chemotherapeutic agents, by conferring on the cell multidrug resistance, thus has major clinical importance.

The transformant host cells of the invention, and recombinant expression vectors used to make them, are useful for testing potential therapeutic agents for their effectiveness against multidrug resistant cells. These agents include agents which are themselves cytotoxic for multidrug resistant cells or which are chemosensitizers of other therapeutic agents. As used herein, the term "chemosensitizer" refers to a substance which can increase the efficacy of a therapeutic agent against a multidrug resistant cell and/or decrease the resistance of a multidrug resistant cell for a therapeutic agent.

A method is provided for identifying a chemosensitizer of a therapeutic agent. The method involves incubating the therapeutic agent with a cell transfected with a nucleic acid which confers resistance to the therapeutic agent on the cell, both with and without a substance to be tested, determining resistance of the cell to the therapeutic agent when incubated with and without the substance to be tested and identifying a substance which is a chemosensitizer of the therapeutic agent by the ability of the substance to decrease the resistance of the cell to the therapeutic agent when incubated with the substance as compared to the resistance of the cell to the therapeutic agent when incubated without the substance. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential chemosensitizing substances can be a cell in culture, e.g. a transformant host cell of the invention, and the therapeutic agent and substance to be tested are incubated in culture with the cell. Alternatively, the cell can be a multidrug resistant cell in a transgenic animal, transgenic for a nucleic acid of the invention, and the therapeutic agent and substance to be tested are administered to the transgenic animal. Furthermore, the cell can be a cell in culture isolated from a multidrug resistant transgenic animal of the invention. The resistance of the cell for the therapeutic agent in the presence and absence of the potential therapeutic agent is assessed by determining the concentration of the therapeutic agent which is cytotoxic for the cell either in the presence or in the absence of the substance being tested.

The invention provides a method for identifying a substance which is directly cytotoxic to a multidrug resistant cell involving incubating a substance to be tested with a cell transfected with a nucleic acid which confers multidrug resistance on the cell and determining the cytotoxicity of the substance for the cell. In a preferred embodiment, the nucleic acid is a recombinant expression vector containing nucleic acid comprising a nucleotide sequence shown in SEQ ID NO: 1. Preferably, the cell into which the nucleic acid is transfected is drug sensitive prior to transfection so that the effects of a potential chemosensitizer are assessed in the presence of a single, isolated multidrug resistance-conferring protein. The cell used to test potential cytotoxic substances can be a cell in culture, e.g. a transformant host cell of the invention, and the substance to be tested is incubated in culture with the cell. Alternatively, the cell can be a multidrug resistant cell in a transgenic animal, transgenic for a nucleic acid of the invention and the substance to be tested is administered to the transgenic animal. Furthermore, the cell can be a cell in culture isolated from a multidrug resistant transgenic animal of the invention.

Additionally, a multidrug resistant cell line such as H69AR, or an equivalent cell line, can be used in the same methods for identifying a chemosensitizer of a therapeutic agent or for identifying a substance which is directly cytotoxic to a multidrug resistant cell.

The isolated proteins of the invention are useful for making antibodies reactive against proteins having MRP activity, as described previously. Alternatively, the antibodies of the invention can be used to isolate a protein of the invention by standard immunoaffinity techniques. Furthermore, the antibodies of the invention, including bispecific antibodies and tetrameric antibody complexes, are useful for diagnostic purposes and for therapeutic purposes.

In one embodiment of the invention, antibodies labelled with a detectable substance, such as a fluorescent marker, an enzyme or a radioactive marker, can be used to identify multidrug resistant tumor cells in a tumor sample or in vivo. Tumor tissue removed from a patient can be used as the tumor sample. In order to prevent tumor samples from being degraded, the samples can be stored at temperatures below $-20°$ C. A tissue section, for example, a freeze-dried or fresh frozen section of tumor tissue removed from a patient, can also be used as the tumor sample. The samples can be fixed and the appropriate method of fixation is chosen depending upon the type of labelling used for the antibodies. Alternatively, a cell membrane fraction can be separated from the tumor tissue removed from a patient and can be used as the tumor sample. Conventional methods such as differential or density gradient centrifugation can be used to separate out a membrane fraction.

A multidrug resistant tumor cell is identified by incubating an antibody of the invention, for example a monoclonal antibody, with a tumor cell to be tested for multidrug resistance. Binding of the antibody to the tumor cell is indicative of the presence on the tumor cell of a protein having MRP activity. The level of antibody binding to the tumor cell can be compared to the level of antibody binding to a normal control cell, and increased binding of the antibody to the tumor cell as compared to the normal cell can be used as an indicator of multidrug resistance. Binding of the antibody to a cell (e.g. a tumor cell to be tested or a normal control cell) can be determined by detecting a detectable substance with which the antibody is labelled. The detectable substance may be directly coupled to the antibody, or alternatively, the detectable substance may be coupled to another molecule which can bind the antibody. For example, an antibody of the invention which has a rabbit Fc region (e.g. which was prepared by immunization of a rabbit) can be detected using a second antibody directed against the rabbit Fc region, wherein the second antibody is coupled to a detectable substance.

A multidrug resistant tumor cell can be detected as described above in vitro in a tumor sample prepared as described above. For example, a tumor section on a microscope slide can be reacted with antibodies using standard immunohistochemistry techniques. Additionally, if a single cell suspension of tumor cells can be achieved, tumor cells can be reacted with antibody and analyzed by flow cytometry. Alternatively, a multidrug resistant tumor cell can be detected in vivo in a subject bearing a tumor. Labelled antibodies can be introduced into the subject and antibodies bound to the tumor can be detected. For example, the antibody can be labelled with a radioactive marker whose presence and location in a subject can be detected by standard imaging techniques.

The antibodies of the invention, and compositions thereof, can also be used to inhibit the multidrug resistance of a multidrug resistant cell. The invention provides a method for inhibiting the multidrug resistance of a multidrug resistant cell comprising inhibiting activity of a protein comprising an amino acid shown in SEQ ID NO: 2 expressed by the multidrug resistant cell. Preferably, the multidrug resistant cell is a tumor cell. In preferred embodiments, the molecule which binds to a protein comprising an amino acid sequence shown in SEQ ID NO: 2 is a monoclonal antibody, bispecific antibody or tetrameric immunological complex of the invention. Multidrug resistance can be inhibited by interfering with the MRP activity of the protein to which the molecule binds. For example, the ability of an MRP protein to transport drugs may be impaired. Accordingly, any molecule which binds to a protein having MRP activity and whose binding inhibits the MRP activity of the protein are encompassed by invention. Isolated proteins of the invention, comprising the amino acid sequence shown in SEQ ID NO: 2, can be used to identify molecules, including and in addition to the antibodies of the invention, which can bind to a protein having MRP activity in a standard binding assay. A multidrug resistant cell in which multidrug resistance is inhibited, by inhibiting the activity of an MRP protein, can further be treated with a therapeutic agent to which the cell is no longer resistant or less resistant due to inhibition of MRP activity in order to kill the cell.

Molecules which bind to a protein comprising an amino acid sequence shown in SEQ ID NO: 2 can also be used in a method for killing a multidrug resistant cell which expresses the protein. Preferably, the multidrug resistant cell is a tumor cell. Destruction of a multidrug resistant cells can be accomplished by labelling the molecule with a substance having toxic or therapeutic activity. The term "substance having toxic or therapeutic activity" as used herein is intended to include molecules whose action can destroy a cell, such as a radioactive isotope, a toxin (e.g. diptheria toxin or ricin), or a chemotherapeutic drug, as well as cells whose action can destroy a cell, such as a cytotoxic cell. The molecule binding to multidrug resistant cells can be directly coupled to a substance having toxic or therapeutic activity (e.g. a ricin-linked monoclonal antibody), or may be indirectly linked to the substance. For example, a bispecific antibody which is capable of crosslinking a tumor cell and a cytotoxic cell can be used, thereby facilitating lysis of the tumor cell. A bispecific antibody can crosslink a tumor cell and the cytotoxic cell by binding to the Fc receptors of cytotoxic cells.

The compositions and methods of the invention can be used to treat patients with tumors displaying multidrug resistance particularly those displaying resistance to anthracyclines, epipodophyllotoxins, vinca alkaloids, and hydrophobic drugs. The methods of the invention for inhibiting the multidrug resistance of a tumor cell and for killing a multidrug resistant tumor cell can be applied to patients having a multidrug resistant tumor. The compositions and methods can be particularly useful in treating breast cancer, leukemias, fibrosarcomas, cervical cancer, gliomas, thyromas, neuroblastomas and lung cancer, in particular small cell lung cancers and non small cell lung cancers.

The invention also provides a diagnostic kit for identifying multidrug resistant tumor cells comprising a molecule which binds to a protein comprising an amino acid sequence shown in SEQ ID NO: 2 for incubation with a sample of tumor cells; means for detecting the molecule bound to the protein, unreacted protein or unbound molecule; means for determining the amount of protein in the sample; and means for comparing the amount of protein in the sample with a standard. Preferably, the molecule is a monoclonal antibody. Other molecules which can bind a protein having MRP activity can be used, including the bispecific antibodies and tetrameric antibody complexes of the invention. The diagnostic kit can also contain an instruction manual for use of the kit.

The invention further provides a diagnostic kit for identifying multidrug resistant tumor cells comprising a nucleotide probe complementary to the sequence, or an oligonucleotide fragment thereof, shown in SEQ ID NO: 1 for hybridization with mRNA from a sample of tumor cells; means for detecting the nucleotide probe bound to mRNA; means for determining the amount of mRNA in the sample; and means for comparing the amount of mRNA in the sample with a standard. The diagnostic kit can also contain an instruction manual for use of the kit.

The invention is further illustrated by the following examples. However, the examples are merely intended to illustrate embodiments of the invention and are not to be construed to limit the scope of the invention. The contents of all references and published patents and patent applications cited throughout this application are hereby incorporated by reference.

EXAMPLE 1

Isolation of cDNA Sequences Derived from mRNAs Overexpressed in H69AR Cells

Figure 1A:
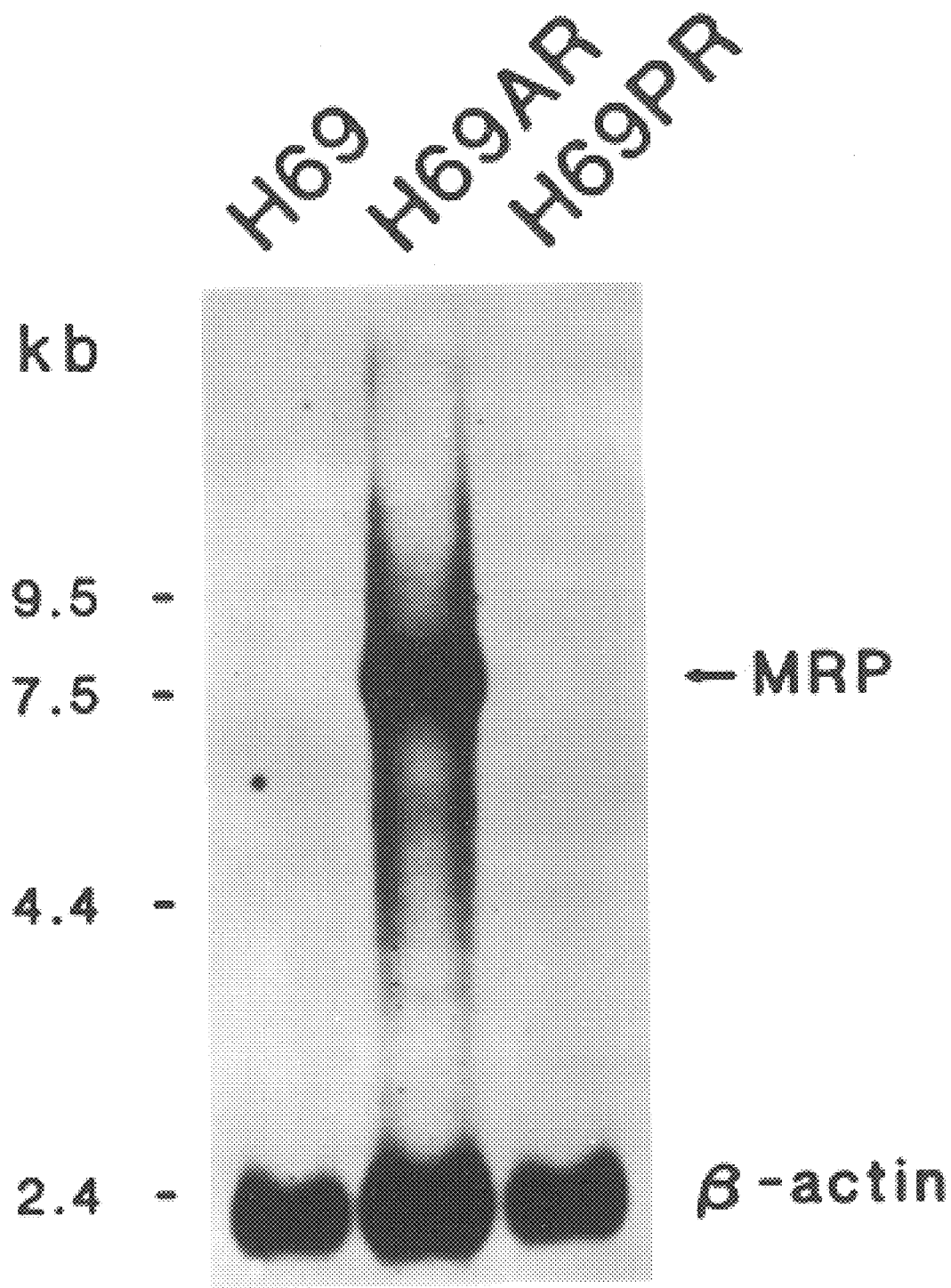
FIG. 1A is a Northern blot of poly(A$^+$)RNA from H69, H69AR and H69PR cells hybridized with a 1.8 kb EcoR1 cDNA fragment of the multidrug resistance protein of the invention.

As part of a search of proteins responsible for the multidrug resistance displayed by H69AR cells, a randomly primed cDNA library constructed from H69AR mRNA was screened using differential hybridization with total cDNA prepared from H69 and H69AR mRNA. One of the clones isolated contained a 2.8 kb cDNA insert and gave a particularly strong differential signal when analyzed on northern blots (FIG. 1A). The analysis of 1 $\mu$g of poly(A$^+$)RNA from each cell line was carried out using standard procedures. Poly(A$^+$)RNA was obtained using a Fast Track™ mRNA isolation kit (Invitrogen) and 1 $\mu$g was electrophoresed on a denaturing formaldehyde agarose gel. The RNA was transferred to nitrocellulose membrane and prehybridized in 50% formamide, 5× SSPE (1×=150 mM NaCl, 10 mM NaH$_2$PO$_4$, 1 mM EDTA, pH 7.4), 2.5× Denhardt's solution (50×=1% bovine serum albumin, 1% polyvinylpyrrolidone, 1% ficoll) and sheared, denatured herring testes DNA (100 $\mu$g/ml) for 4–16 hours at 42° C. The blot was probed with a 1.8 kb EcoRI fragment of MRP, labelled to a specific activity of >5×10$^8$ cmp/$\mu$g DNA with $\alpha$-[$^{32}$P]-dCTP (3000 Ci/mmol; Dupont/NEN) by the random priming method [A. P. Feinberg, B. Vogelstein, Analyt. Biochem. 132, 6 (1983)]. Hybridization was carried out for 16–20 hours at 42° C. Blots were washed three times in 0.1% SDS and 0.1× SSC (pH 7.0) for 30 minutes each at 52° C. and then exposed to film. To estimate variation in RNA loading of the gel, the blot was reprobed with a $^{32}$P-labelled $\beta$-actin cDNA (201pBv2.2) [H. Ueyama, H. Hamada, N. Battula, T. Kakunaga, Mol. Cell. Biol. 4, 1073 (1984)]. The autoradiograph shown in FIG. 1A is a 5 hour exposure with intensifying screens at −70° C. The size of the overexpressed mRNA in H69AR cells was estimated to be approximately 7 kb. Prolonged exposure of the film revealed low levels of this mRNA in H69 and H69PR cells. The concentration of this mRNA was increased 100 fold in H69AR cells relative to H69 cells. The level of this mRNA in H69PR, a drug sensitive revertant of H69AR, had decreased approximately 20-fold relative to that found in H69AR, further substantiating the correlation of overexpression of this particular mRNA with a multidrug resistance phenotype.

Figure 1B:
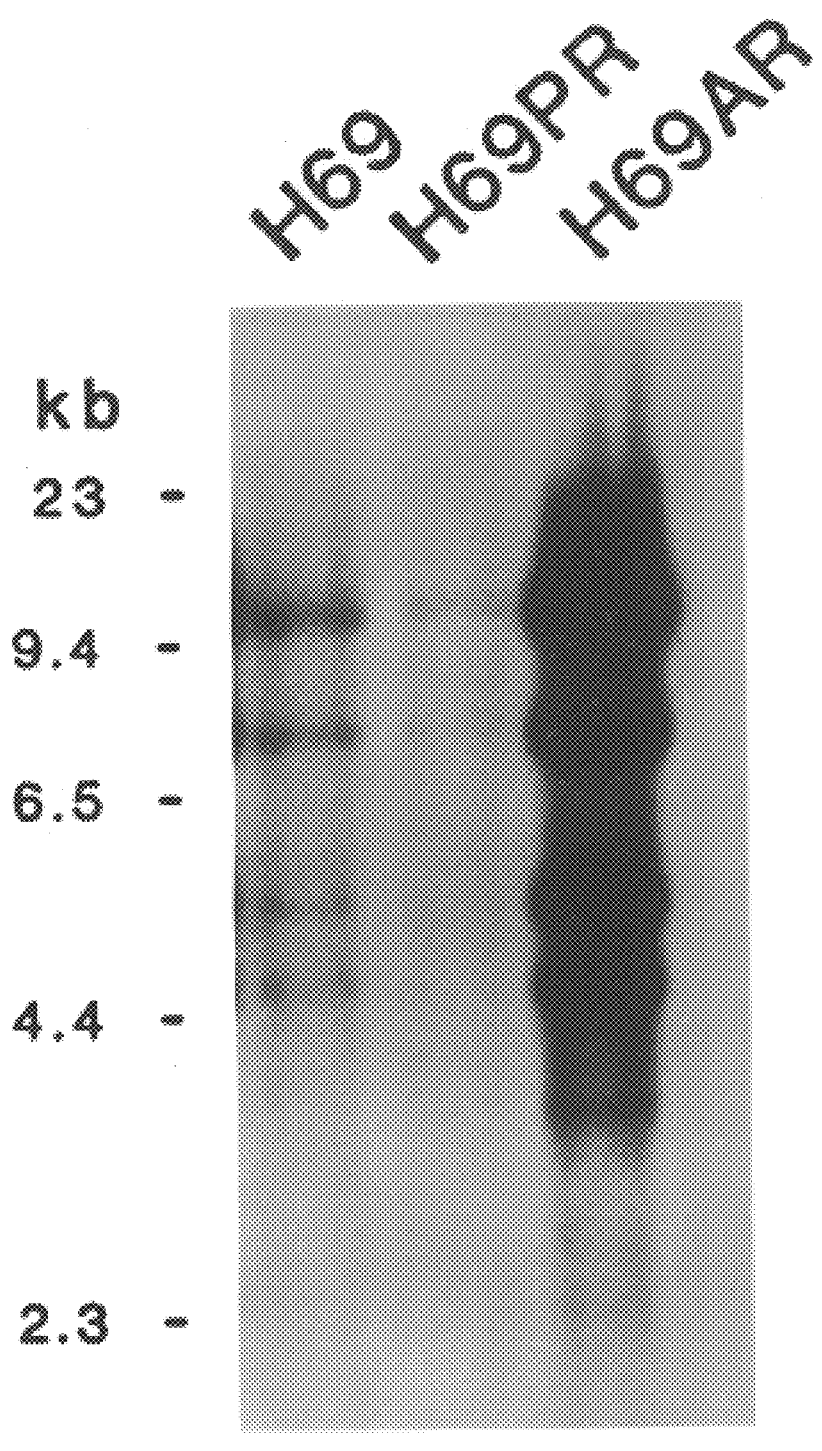
FIG. 1B is a Southern blot analysis of EcoRI-digested genomic DNA from H69, H69AR and H69PR cells hybridized with a 1.8 kb EcoR1 cDNA fragment of the multidrug resistance protein of the invention.

Southern blot analyses of H69, H69AR and H69PR DNA indicated that the major mechanism underlying overexpression was gene amplification. Ten µg of each DNA was digested with EcoRI, electrophoresed through a 0.7% agarose gel and blotted onto a nitrocellulose membrane. The DNA was hybridized with a 1.8 kb EcoRI cDNA fragment of MRP, labelled by random priming with $\alpha$-[$^{32}$P]-dCTP. The autoradiograph shown in FIG. 1B is a 6 hour exposure at −70° C. Based on the examination of several restriction digests and normalization of the amounts of DNA loaded, the MRP gene was amplified 40–50 fold in resistant H69AR cells and no differences in the copy number of the gene in H69 and H69PR cells were detected.

Figure 1C:
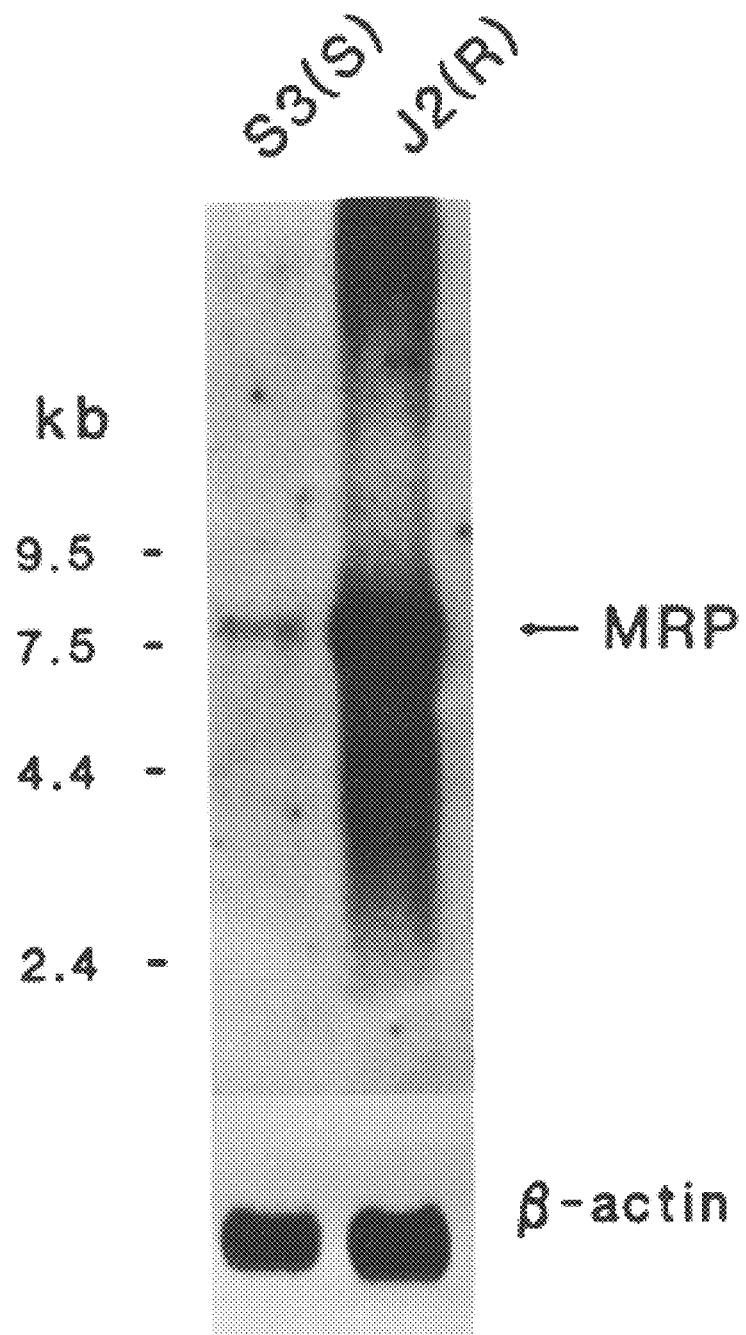
FIG. 1C is a Northern blot of sensitive and resistant HeLa cell poly (A$^+$)RNA hybridized with a 1.8 kb EcoRI cDNA fragment of the multidrug resistance protein of the invention.

The mRNA was also overexpressed 10–15 fold in a doxorubicin-selected multidrug resistant HeLa cell line that does not overexpress P-glycoprotein (FIG. 1C). S3 and J2c are drug sensitive and resistant HeLa cell lines obtained from the laboratory of Dr. R. M. Baker (Roswell Park Memorial Institute). Two µg of poly(A$^+$)RNA from each cell line was electrophoresed, blotted and probed with MRP cDNA as described for FIG. 1A. The MRP and β-actin autoradiographs shown in FIG. 1C are 18 hour and 1 hour exposures, respectively, at −70° C. Southern blotting of DNA from S3 and J2c cells indicated that the MRP gene was amplified 10–15 fold in the resistant cell line. These findings provide further evidence of the association of elevated levels of this mRNA with multidrug resistance.

The initial 2.8 kb cDNA clone was sequenced, allowing the isolation of overlapping clones by rescreening the H69AR cDNA library with synthetic oligonucleotides. A single, extended open reading frame of 1531 amino acids was defined encoding a protein designated as multidrug resistance associated protein (MRP). The translated GenBank and SwissProt databases were searched for similarities to MRP using the FASTA program. The search revealed that MRP is a novel member of the ATP-binding cassette (ABC) superfamily of transport systems. Members of this superfamily are involved in the energy dependent transport of a wide variety of molecules across cell membranes in both eukaryotes and prokaryotes. Included in this superfamily are the human multidrug transporter P-glycoprotein (MDR1) and the cystic fibrosis transmembrane conductance regulator (CFTR).

Figure 2:
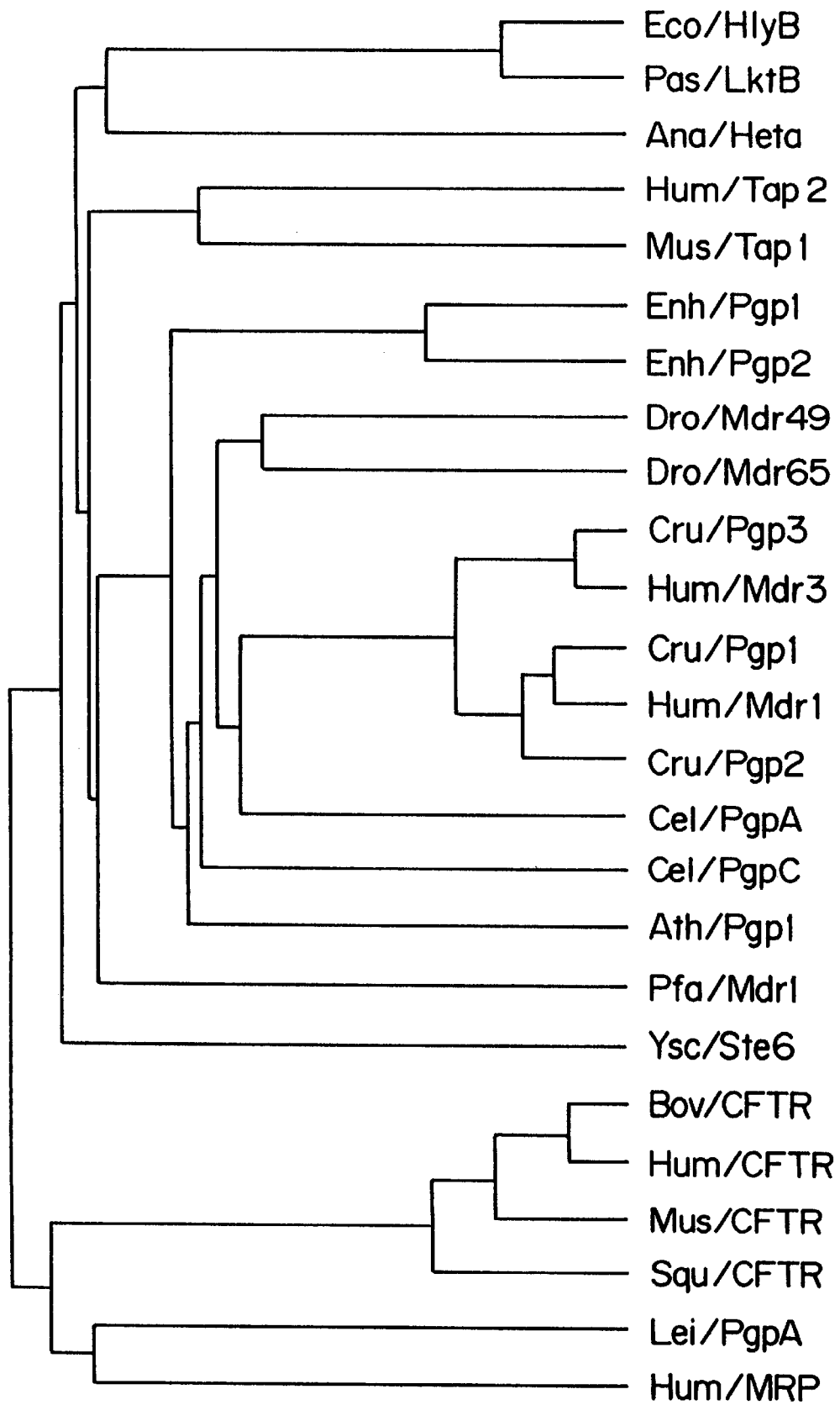
FIG. 2 is a cluster analysis of the relative similarity of the multidrug resistance protein of the invention to selected members of the ATP-binding cassette transporter superfamily that contain hydrophobic transmembrane regions followed by nucleotide binding folds.

EXAMPLE 2
Relationship of MRP to Other Members of the ABC Transporter Superfamily The relationship of MRP to the various members of the ABC transporter superfamily was examined using the PILEUP program from the Genetics Computer Group package (version 7) using a modified version of the progressive alignment method of Feng and Doolittle [J. Mol. Evol. 25, 351 (1987)]. A representative selection of a phylogenetically broad range of ABC proteins that are comprised of hydrophobic transmembrane regions followed by nucleotide binding regions, and whose sequences could be retrieved from GenBank and SwissProt databases, were included in this analysis. The analysis divides this family of proteins into two major subgroups (FIG. 2). One of the major subgroups consists of the cluster containing MRP (Hum/MRP), the leishmania P-glycoprotein-related molecule (Lei/PgpA) and the CFTRs (Hum/CFTR, Bov/CFTR, Mus/CFTR and Squ/CFTR). The other subgroup consists of the P-glycoproteins, the MHC class II-linked peptide transporters (Hum/Tap2, Mus/Tap1), the bacterial exporters (Eco/HlyB, Pas/LktB), the heterocyst differentiation protein (Ana/HetA), the malarial parasite transporter (Pfa/Mdr1) and the yeast mating factor exporter (Ysc/Ste6).

The dendrogram in FIG. 2 indicates that MRP is only distantly related to previously identified members of the ABC transporter superfamily. Although the analysis suggests that it is most closely related to Lei/PgpA, the similarity between MRP and Lei/PgpA resides predominantly in two regions, both containing signatures of nucleotide binding folds (NBFs) (FIG. 3A). The alignment was generated using PILEUP as described in FIG. 2. The MRP sequence shown was compiled from four overlapping lambda gt11 cDNA clones. The alignment begins at a methionine residue in MRP that aligns with the initiator methionine of Lei/PgpA. The predicted initiator methionine of MRP itself is located 66 amino acids upstream. Identical and conserved amino acids are identified in FIG. 3A by double and single dots, respectively. The Walker A and B motifs and the 'active transport' family signature that are characteristic of nucleotide binding folds (NBFs) of ABC transporters are indicated by single lines and denoted A, B, and C, respectively. The predicted transmembrane regions of each protein are indicated by double lines. The region in Lei/PgpA indicated by a dashed line has a mean hydrophobicity value approaching that of a transmembrane region.

Figure 3B:
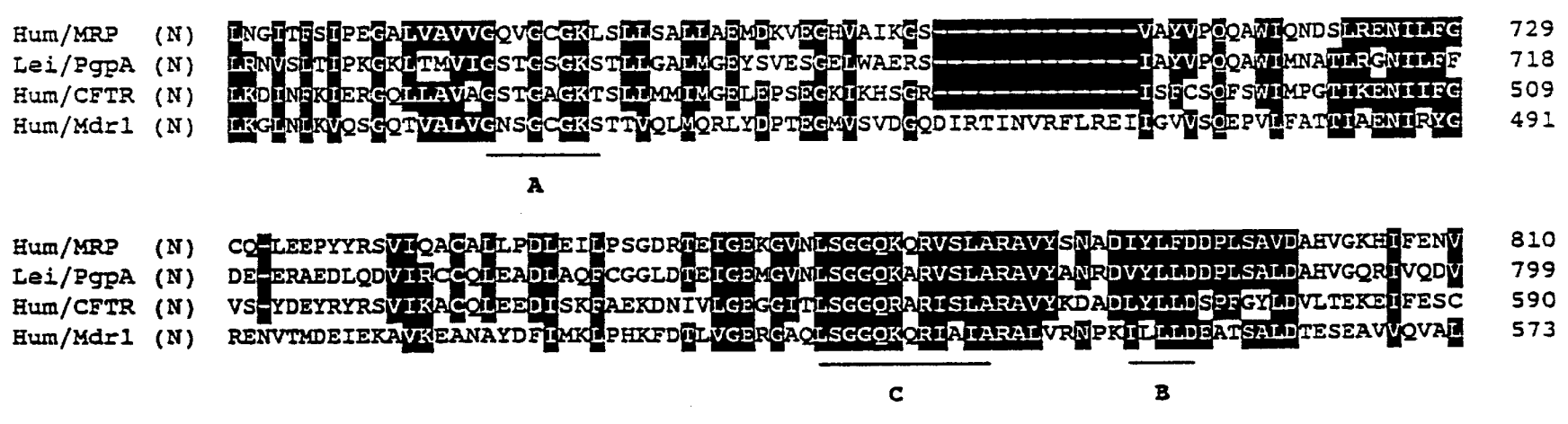

It has been proposed that the bipartite structure of P-glycoproteins reflects duplication of an ancestral gene that occurred prior to the evolutionary separation of animals and plants. However, comparison of the NH$_2$- and COOH-terminal NBFs of MRP and Lei/PgpA revealed less similarity than typically found between the two corresponding regions of P-glycoproteins. To determine whether this was a common structural feature of MRP, Lei/PgpA and Hum/CFTR, their NH$_2$- and COOH-terminal NBFs were aligned with each other and those of several P-glycoproteins. One such comparison using human P-glycoprotein (Hum/Mdr1) as an example is shown in FIG. 3B. Shown in FIG. 3B are the NH$_2$-terminal (N) and COOH-terminal (C) halves of the deduced amino acid sequence of MRP corresponding to 1tpgpA (Lei/PgpA) (amino acids 650–799 and 1303–1463), human CFTR (Hum/CFTR) (amino acids 441–590 and 1227–1385), and MDR1 (Hum/Mdr1)(amino acids 410–573 and 1053–1215). The sequences are presented as aligned by PILEUP. Reverse type indicates that 3 of 4 amino acids at that position are identical or conserved. The conserved motifs A, B, and C described in FIG. 3A are underscored by a single line. The NH$_2$-terminal NBFs of MRP, Hum/CFTR and Lei/PgpA share structural features that clearly distinguish them from the NH$_2$-terminal NBF of Hum/Mdr1, particularly in the spacing of conserved motifs. This difference in spacing also contributes to the relatively low similarity between NH$_2$- and COOH-terminal NBFs in each of the three proteins. In addition, the COOH-terminal NBFs of MRP, Lei/PgpA and Hum/CFTR are more similar to each other than to either the COOH or NH$_2$-terminal NBFs of Hum/Mdr1. Similarity scores for the NH$_2$-terminal NBFs relative to MRP are: Lei/PgpA (0.93), Hum/CFTR (0.85) and Hum/Mdr1(0.60). Comparable COOH-terminal scores are Lei/PgpA (0.87), Hum/CFTR (0.84) and Hum/Mdr1 (0.73). Similarity scores for NH$_2$- and COOH-terminal NBFs within the same protein are: MRP (0.61), Lei/PgpA (0.60), Hum/CFTR (0.62) and Hum/Mdr1 (1.10). These observations, combined with the overall analysis shown in FIG. 2, suggest that MRP, Lei/PgpA and CFTR evolved from a common ancestor containing both NH$_2$- and COOH-terminal NBFs, which was distinct, or diverged from the ancestral gene of the P-glycoproteins prior to the animal/plant separation.

EXAMPLE 3
Expression of MRP in Normal Tissues

Figure 4:
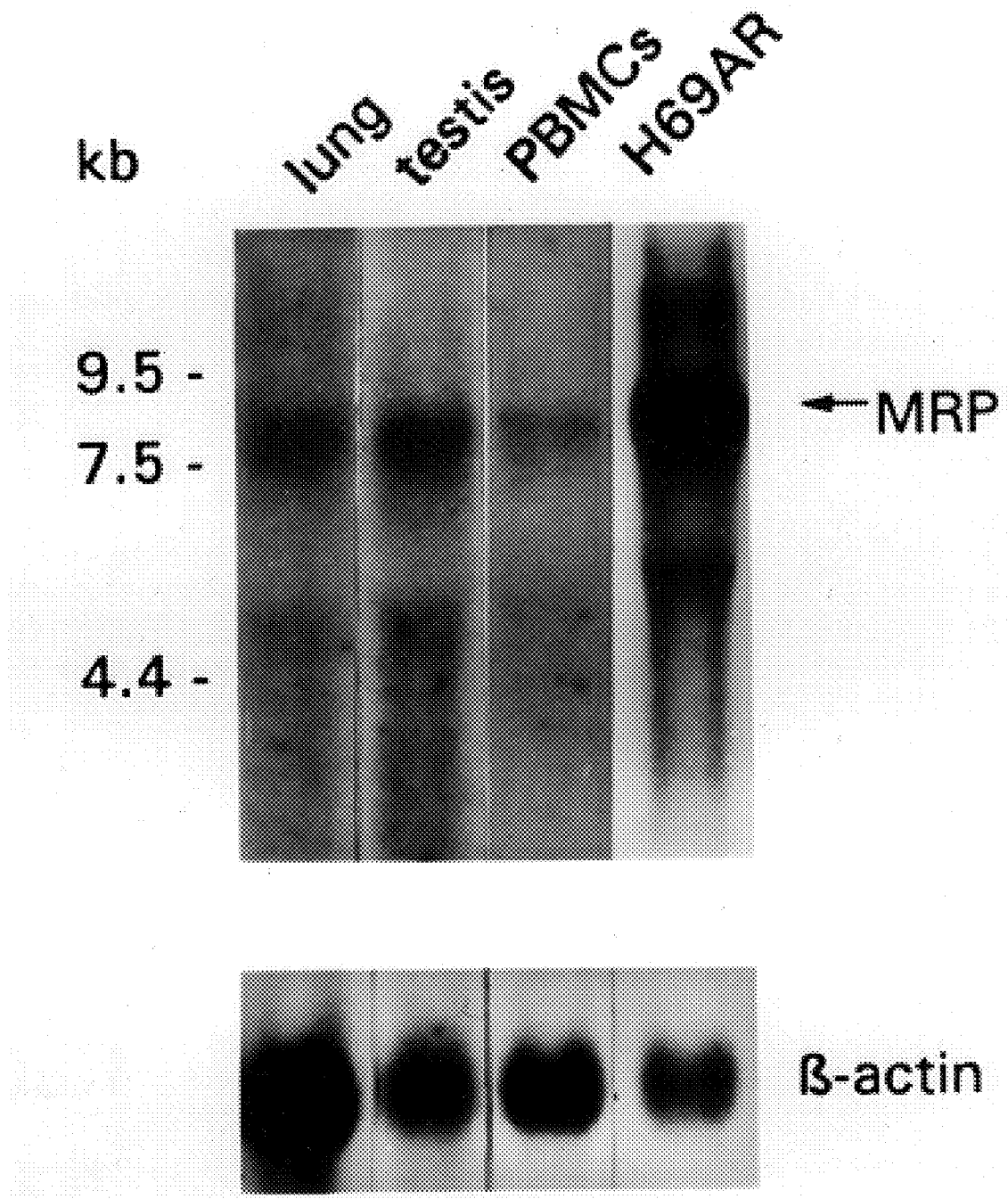
FIG. 4 is a Northern blot of total RNA from normal tissues hybridized with a 0.9 kb EcoRI cDNA fragment of the multidrug resistance protein of the invention.

Despite knowledge of its structure and its ability to act as a drug efflux pump, the normal physiological role(s) of P-glycoprotein has not been elucidated. Some possible clues to its function have been provided by its distribution in normal tissues. P-glycoprotein is highly expressed in secretory organs and tissues, such as the adrenals, kidneys, lumenal epithelium of the colon and the murine gravid uterus. It has also been detected in the lung although this finding is variable. Based on the cell types in which it is expressed, it has been postulated that P-glycoprotein may be involved in steroid transport and/or protection against xenobiotics. Northern blot analyses of total RNA preparations from a range of human tissues shown that MRP is expressed at relatively high levels in lung, testis and peripheral blood mononuclear cells (PBMCs) (FIG. 4). Lung and testis RNAs were obtained from Clontech Laboratories (Palo Alto, Calif.). PBMC RNA was prepared from cells isolated by centrifugation over Ficoll-Isopaque (specific gravity 1.078 g/ml; Pharmacia) of peripheral blood from healthy volunteers. Total RNAs from lung, testis and PBMCs (30 µg) and H69AR cells (10 µg) were analyzed as for FIG. 1A. The autoradiograph shown in FIG. 4 is from a blot probed with a 0.9 kb EcoRI cDNA fragment of MRP and exposed for 38 hours for the normal tissue RNAs and for 24 hours for the H69AR RNA. The blot was stripped and reprobed with $^{32}$P-labelled β-actin cDNA. The actin autoradiograph is a 24 hour exposure. MRP transcripts were below the level of detection in placenta, brain, kidney, salivary gland, uterus, liver and spleen.

EXAMPLE 4
Mapping of the Human MRP Gene

Figure 5:
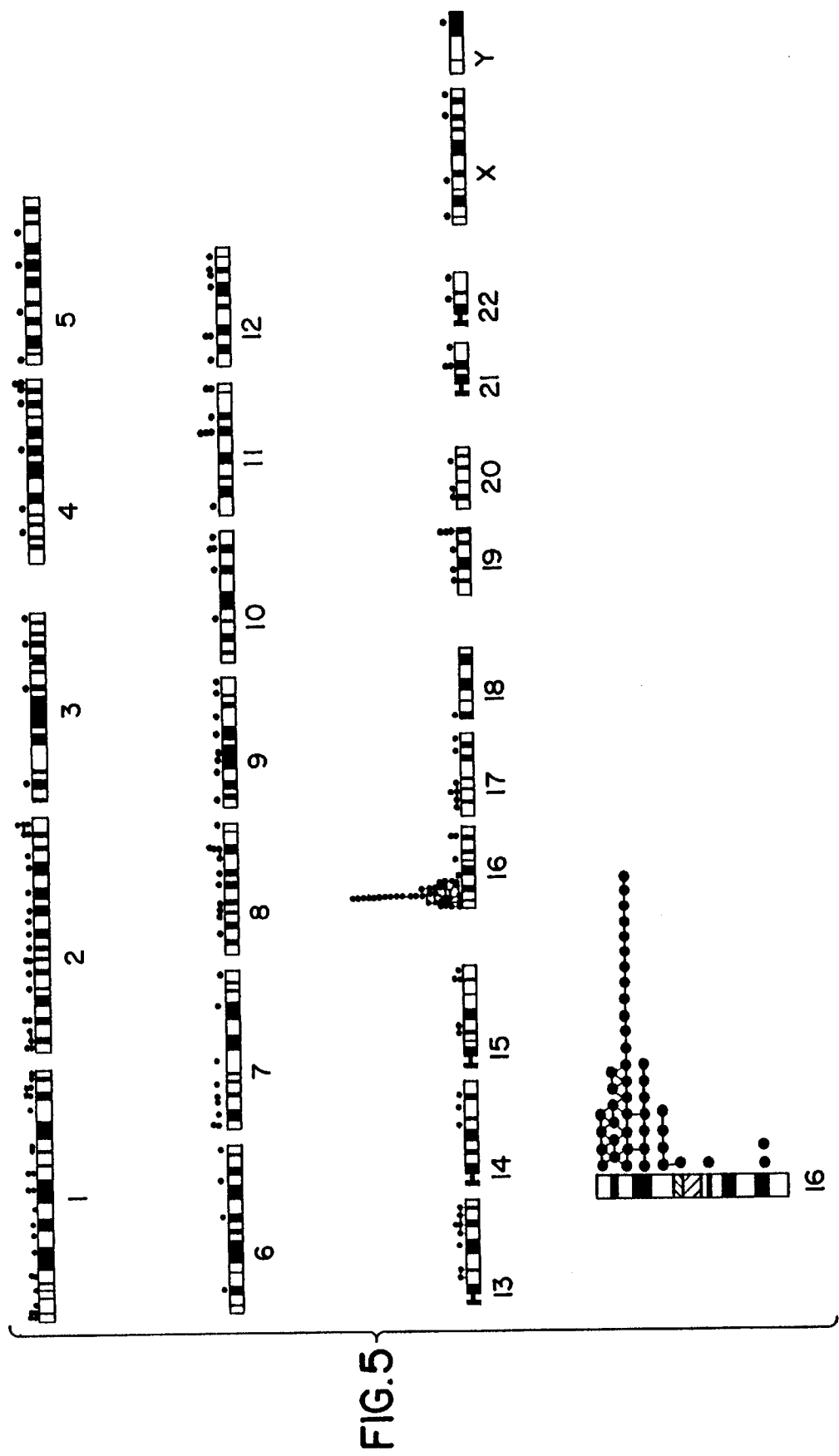
FIG. 5 is an ISCN-derived idiogram of the human karyotype showing silver grain distribution following in situ hybridization of a 1.8 kb EcoRI cDNA fragment of the multidrug resistance protein of the invention to metaphase chromosomes.

The human CFTR and MDR1 genes have been mapped to chromosome 7 at bands q31 and q21, respectively. The possible evolutionary relationship of MRP to these proteins prompted examination of the possibility that the MRP gene may be linked to one of these previously identified loci. In situ hybridization of a 1.8 kb EcoRI fragment of MRP cDNA was performed using the method of Harper and Saunders [Chromosoma 8, 431 (1981)]. Metaphase chromosomes on slides were denatured for 2 minutes at 70° C. in 70% deionized formamide, 2× SSC and then dehydrated with ethanol. The hybridization mixture consisted of 50% deionized formamide, 10% dextran sulfate, 2× SSC (pH 6), 20 µg/ml sonicated salmon sperm DNA and 0.2 µg/ml $^3$H-labelled MRP cDNA. The cDNA probe was labelled to a specific activity of 8.5×10$^8$ cpm/µg DNA with [$^3$H]-dTTP and [$^3$H]-dATP (New England Nuclear) using a Multiprime DNA Labelling System (Amersham) and denatured in the hybridization solution at 70° C. for 5 minutes. Fifty µl of the probe solution was placed on each slide and incubated at 37° C. overnight. After hybridization, the slides were washed in 50% deionized formamide, 2× SSC followed by 2× SSC (pH 7) and then dehydrated sequentially in ethanol. The slides were coated with Kodak NTB/2 emulsion and developed after exposure for 5 weeks at 4° C. Chromosomes were stained with a modified fluorescence, 0.25% Wright's stain procedure [C. C. Lin, P. N. Daper, M. Braekeleer, Cytogenet. Cell Genet. 39, 269 (1985)]. The positions of 200 silver grains directly over or touching well-banded metaphase chromosomes were recorded on the ISCN-derived idiogram of the human karyotype. A significant clustering of grains (40) was observed in the 16p region (p<0.0001) and the peak of the distribution was at 16p13.1, confirming that MRP was not linked to either CFTR or MDR genes. Approximately 160 metaphases were examined. These results are summarized in FIG. 5.

EXAMPLE 5
Expression of MRP in a Drug Sensitive Cell Confers Doxorubicin Resistance on the Cell While increased concentrations of MRP and mRNA have been detected in multidrug resistant cell lines derived from a variety of tissues and several of these cell lines have also been shown to contain multiple copies of the MRP gene as a result of amplification and translocation of a region of chromosome 16 spanning the MRP gene at band p13.1, it remained possible, in view of the multistep selection procedures used to derive the cell lines, that overexpression of the MRP gene is only one component of a set of alterations required to confer multidrug resistance. The ability of MRP alone to confer drug resistance on a drug sensitive cell line was determined by constructing an MRP expression vector, transfecting the expression vector into drug sensitive cells and assessing the relative drug resistance of the transfected cell populations.

A DNA fragment corresponding to the complete coding region of MRP mRNA plus 86 nucleotides of 5' and 32 nucleotides of 3' untranslated sequence was assembled and transferred into the expression vector pRc/CMV under the control of the human cytomegalovirus promoter. A DNA fragment containing the complete coding region of MRP mRNA was assembled in the vector, pBluescript 11 KS$^+$ (Stratagene), using overlapping cDNA clones or PCR products generated from these clones. The fidelity of the MRP sequence was confirmed by DNA sequence analysis before moving the intact MRP fragment to the eukaryotic expression vector, pRc/CMV (Invitrogen). The integrity of the MRP fragment in the expression vector was assessed by detailed restriction mapping and DNA sequence analysis of the cloning sites. In the pRc/CMV vector, MRP expression is under the control of the enhancer/promoter sequence from the immediate early gene of human cytomegalovirus. The MRP transcript also contains part of the 3' untranslated region and the polyadenylation signal from bovine growth hormone mRNA which is provided by the vector. Thus, the pRc/CMV-MRP construct generates a transcript of 5.2 to 5.3 kb that includes the entire coding sequence (86 nucleotides of which are derived from MRP mRNA sequence), and approximately 250 nucleotides of 3' untranslated sequence (32 nucleotides of which are derived from MRP mRNA sequence). This vector also contains the bacterial aminoglycoside 3' phosphotransferase gene which confers resistance to geneticin (G418).

HeLa cells were transfected with either the parental vector, or the vector containing the MRP coding region, using supercoiled DNA and a standard calcium phosphate transfection procedure. HeLa cells were transfected with the pRc/CMV vector or the vector containing the MRP coding sequence using a standard calcium phosphate transfection procedure [J. Sambrook, E. F. Firtsch, T. Maniatis, *Molecular Cloning: A Laboratory Manual*, Cold Spring Harbor Laboratory Press, Cold Spring Harbor, N.Y. (1989)]. Approximately, 50,000 cells in each well of a 6-well tissue culture plate were exposed for 16 hours to 10 µg of supercoiled DNA in a calcium phosphate precipitate. After forty-eight hours, the growth medium was changed to include G418 at 200 µg/ml which selected for cells that expressed the neomycin resistance gene encoded by the pRc/CMV vector. Three weeks later, six independently transfected populations of cells were tested for resistance to doxorubicin using a tetrazolium salt microtiter plate assay (S. P. C. Cole, *Cancer Chemother. Pharmacol.* 26, 250 (1990)). Those populations demonstrating increased relative resistance to the drug were expanded for testing for cross-resistance to other cytotoxic drugs, and analysis of MRP mRNA and protein levels.

Poly(A)$^+$ RNA was isolated using the Micro-FastTrack RNA isolation kit (Invitrogen). The RNA was subjected to electrophoresis on a formaldehyde agarose gel and transferred to Zetaprobe membrane (Bio-Rad). The blots were hybridized with $^{32}$P-labeled cDNA fragment probes complementary to the mRNAs for MRP, MDR1 [A. M. Van der Bliek, F. Baas, T. Ten Houte de Lange, P. M. Kooiman, T. Van der Velde Koerts, P. Borst, EMBO J. 6, 3325 (1987)], topoisomerase 11 α [T. D. Y. Chung, F. H. Drake, K. B. Tan, S. R. Per, S. T. Crooke, C. K. Mirabelli, *Proc. Natl. Acad. Sci. U.S.A.* 86 9431 (1989)], topoisomerase 11 β [ibid.], annexin 11 (S. P. C. Cole, M. J. Pinkoski, G. Bhardwaj, R. G. Deeley, Br. J. Cancer 65, 498 (1992)), and a region of the pRc/CMV vector encoding part of the 3' untranslated region and polyadenylation signal from the bovine growth hormone gene. Hybridization of the probes was quantified by densitometry of the autoradiographs on a Molecular Dynamics Computing Densitometer. Care was taken to compare autoradiographic exposures that were within the linear range of the film. In addition, variations in loading of RNA on the gels were estimated by probing blots with a $^{32}$P-labeled glyceraldehyde-3-phosphate dehydrogenase (GAPDH) cDNA fragment (ATCC/NIH #57090), and by densitometric scanning of the ethidium bromide-stained ribosomal RNA bands on photographic negatives of the RNA gels.

The relative amounts of MRP protein were assessed by immunoblot analysis of total cell extracts and membrane-enriched fractions. Cell pellets were resuspended at $5 \times 10^7$ cells/ml in buffer containing 10 mM Tris-HCl, pH 7.4, 10 mM KCl, 1.5 mM $MgCl_2$, and protease inhibitors (2 mM phenylmethylsulfonyfluoride, 50 μg/ml antipain, 2 μg/ml aprotinin, 200 μg/ml EDTA, 200 μg/ml benzamidine, 1 μg/ml pepstatin). After 10 min on ice, cells were homogenized with approximately 80 strokes of a Tenbroeck homogenizer. The homogenate was adjusted to 250 mM in sucrose before remaining intact cells and nuclei were removed by centrifugation at 800× g at 4° C. for 20 min. To prepare a membrane-enriched fraction, the supernatant was centrifuged at 100,000× g at 4° C. for 20 min in a Beckman TL-100 ultracentrifuge and the pellet resuspended in 10 mM Tris-HCl, pH 7.4, 125 mM sucrose, and the protease inhibitors listed above. For sodium dodecyl sulphate (SDS) polyacrylamide gel electrophoresis and immunoblotting, appropriate amounts of protein were mixed 1:1 with solubilizing buffer (final concentration 4 M urea, 0.5% SDS, 50 mM dithiothreitol). Samples were loaded without heating onto a 7% resolving gel with a 4% stacking gel. Proteins were transferred to Immobilon-P PVDF membranes (Millipore) using 50 mM 3-(cyclohexylamino)-1-propanesulfonate, pH 11.0. For detection of MRP, blots were incubated with an affinity-purified, rabbit polyclonal antibody raised against a synthetic peptide, the sequence of which was predicted from that of the cloned MRP cDNA and which is not found in any other known protein. Antibody binding was visualized with horseradish peroxidase-conjugated goat anti-rabbit IgG and enhanced chemiluminescence detection (Amersham). The affinity-purified anti-MRP antibody recognizes a glycosylated, integral membrane protein with an apparent molecular weight of 190 kilodaltons. In its deglycosylated form, the molecular weight of the protein decreases to 165- to 170 kilodaltons which is in agreement with the molecular weight of 171 kilodaltons predicted from the primary amino acid sequence of MRP.

At this time, the level of G418 in the growth medium was increased to 400 or 800 μg/ml without any noticeable effect on the growth rate of cells transfected with either the parental vector or the vector containing the MRP coding sequence. Transfected populations have been grown continuously for up to four months in G418-containing medium without any change in the level of resistance to doxorubicin. Integration of these vectors into genomic DNA has the potential to alter the expression of endogenous genes that might adventitiously increase drug resistance. Consequently, chemotherapeutic drugs were not used as selecting agents. Populations of transfected cells were selected solely by their ability to grow in the presence of G418. Since cells overexpressing MRP do not display increased resistance to this antibiotic, variable levels of expression of MRP are to be expected in the transfected cell populations.

Figure 6:
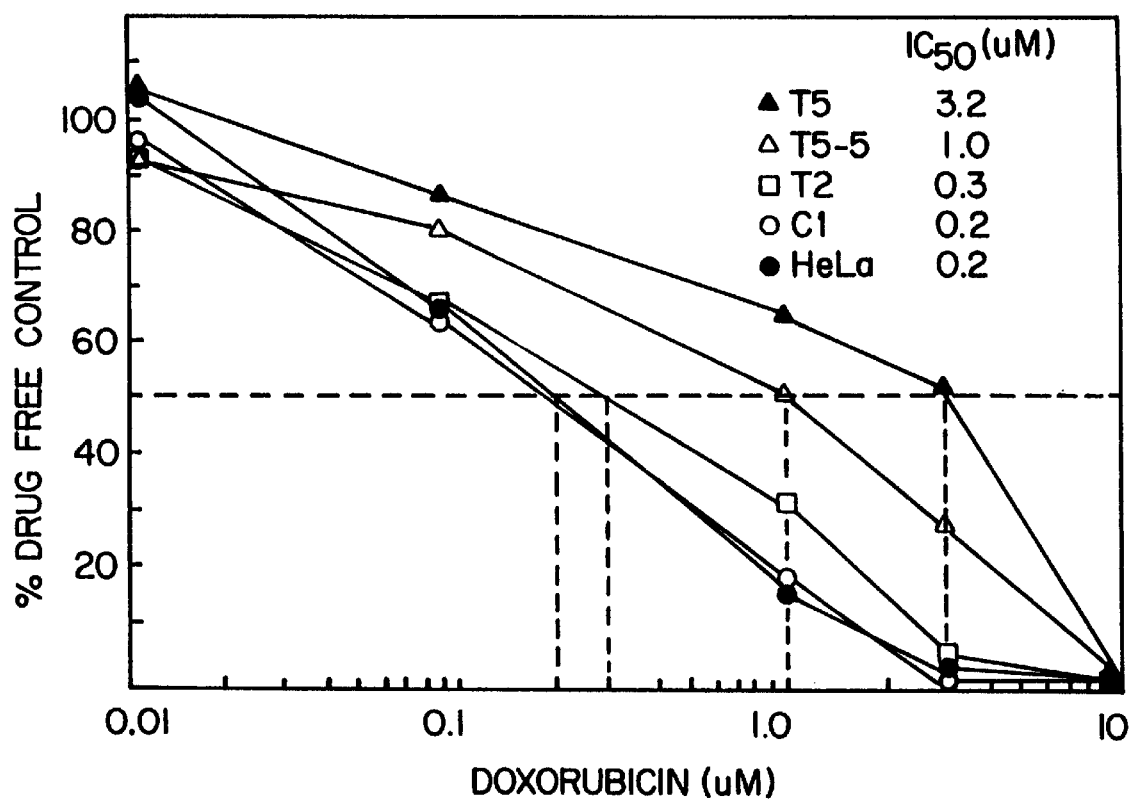
FIG. 6 is a graph depicting the relative cytotoxicity of doxorubicin on MRP-transfected HeLa cell populations (T2, T5), a clone of the T5 population (T5-5), untransfected HeLa cells and HeLa cells transfected with the parental expression vector (C1).

The relative resistances to doxorubicin are shown for two examples of G418 resistant cell populations transfected with the MRP expression vector (T2 and T5), as well as untransfected HeLa cells and a population transfected with the parental vector (C1) (FIG. 6). Key: HeLa cells ('); HeLa cells transfected with the expression vector pRc/CMV (C1, °); HeLa cells transfected with the vector containing the MRP coding sequence (T2, □; T5, Δ); and a clone isolated from the doxorubicin-resistant transfected T5 cells shown (Δ, T5-5). Each point represents the mean of triplicate determinations in a single experiment and standard deviations were <5%. Similar results were obtained in three additional experiments. The $IC_{50}$ is indicated on the figure and is defined as the concentration of doxorubicin required to decrease by 50% the values obtained with untreated cells. In the examples shown, one of the populations transfected with the MRP expression vector (T2) displayed little change in doxorubicin resistance while resistance of the other (T5) was increased 15-fold. In addition, several clones from the resistant population were grown in the presence of G418 and their degree of doxorubicin resistance determined. Dose response curves for two of the transfectants (T2, T5) and for one of the clones (T5-5) were then compared to determine whether their resistance to doxorubicin correlated with the concentrations of MRP mRNA.

Figure 7A:
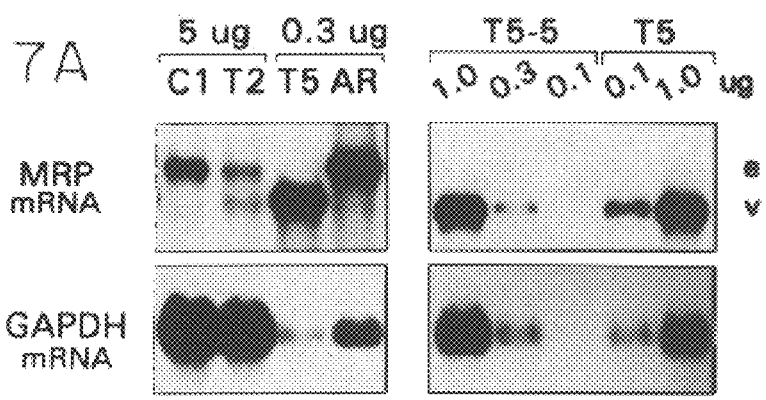
FIG. 7A is a Northern blot of poly(A)+RNA from transfected and control HeLa cells hybridized with a 4 kb MRP cDNA fragment which hybridizes with endogenous MRP mRNA (e) and expression vector-derived MRP mRNA (v). Hybridization with a GAPDH cDNA demonstrates the relative amounts of poly(A)+ RNA in each lane.
Figure 7B:
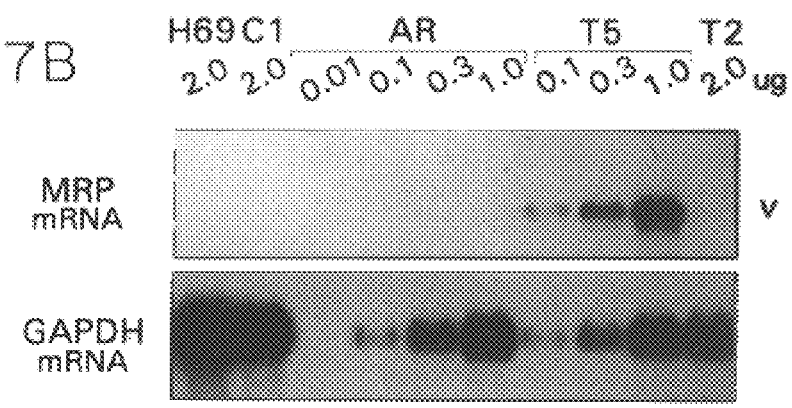
FIG. 7B is a Northern blot of poly(A)+ RNA from transfected HeLa cells and control cells hybridized with a DNA fragment from the pRc/CMV vector which hybridizes only to expression vector-derived MRP mRNA (v). Hybridization with a GAPDH cDNA demonstrates the relative amounts of poly(A)+ RNA in each lane.

The MRP mRNA produced from the expression vector has a predicted length of 5.2 to 5.3 kb including a poly(A) tail, thus allowing it to be distinguished from the longer, endogenous MRP mRNA by Northern analysis. A blot of poly(A)$^+$ RNA from the cell populations shown in FIG. 6 that was hybridized with a cloned cDNA probe corresponding to part of the MRP coding sequence, revealed a relatively abundant mRNA of approximately 5.3 Kb in the resistant transfectants and low levels of the endogenous MRP mRNA (FIG. 7A). The relative concentration of the 5.3 kb mRNA is 70- to 80-fold and 20- to 30- fold higher in the resistant cell population (T5) and clone (T5-5), respectively, than that of endogenous MRP mRNA present in the control population (C1). Relative levels of mRNAs were determined by densitometry and normalization to the levels of GAPDH mRNA. Expression of the 5.3 kb MRP mRNA in the transfected cell population which showed little change in resistance (T2) was only approximately half that of endogenous MRP mRNA. Similar RNA blots were also probed with a DNA fragment from the pRc/CMV plasmid that forms part of the 3' untranslated region of the vector encoded MRP mRNA. This probe hybridized only with the 5.3 kb MRP mRNA, confirming that it was transcribed from the vector and did not result from the increased expression of an endogenous MRP-related gene (FIG. 7B). Thus in cells transfected with the MRP expression vector the relative level of drug resistance increases with the concentration of MRP mRNA.

Figure 7C:
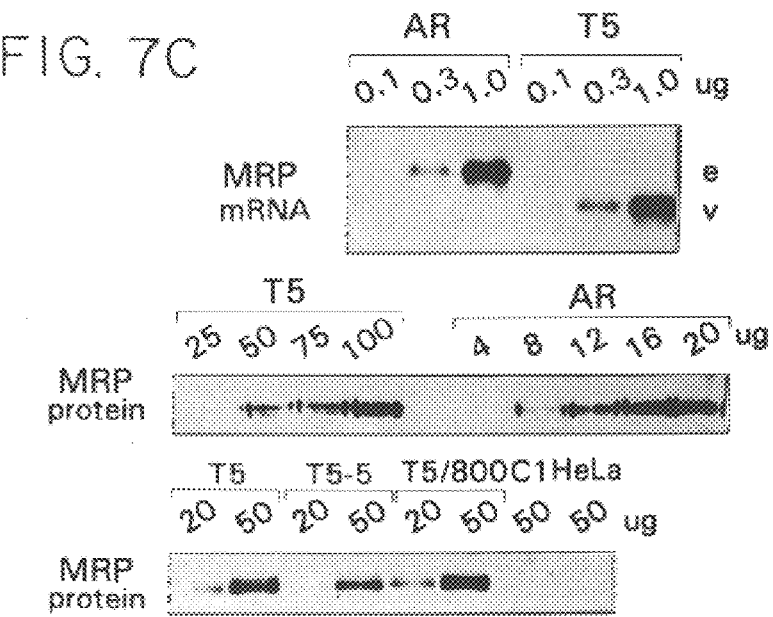
FIG. 7C is a Northern blot (MRP mRNA) and immunoblots (MRP protein) depicting the relative levels of expression vector-derived MRP mRNA and protein in transfected HeLa cells and endogenous MRP mRNA and protein in the H69AR cell line.

The concentration of endogenous MRP mRNA in the multidrug resistant H69AR cells (labeled AR in the figures) is approximately 100-fold higher than in the H69 parental cells (labeled H69 in the figures) and the relative resistances of the two cell lines to doxorubicin also differ by 50- to 100-fold. Vector encoded MRP mRNA levels in the T5 HeLa cell population are 70- to 80-fold higher than endogenous MRP mRNA levels in the parental cells. However, drug resistance is increased only 15-fold. To investigate why the relative increase in drug resistance was lower in the transfectants than in H69AR cells, we compared the levels of MRP mRNA and protein in the two different cell types. Northern analysis revealed that the levels of endogenous MRP mRNA in H69 cells and HeLa cells transfected with the pRc/CMV parental vector were similar. The relative abundance of vector encoded MRP mRNA in the drug resistant transfectant cell population (T5) was also comparable to that of endogenous MRP mRNA in H69AR cells (FIG. 7C). However, a protein blot with affinity purified anti-MRP antibody indicated that the level of protein in the T5 HeLa cell transfectants was 5- to 8-fold lower than in H69AR cells (FIG. 7C). These findings are consistent with the 15-fold increase in resistance observed in the transfected T5 cells compared to the 50- to 100-fold increase in H69AR cells. The lower level of protein in the transfected cells in most likely attributable to a difference in translational efficiency between the vector encoded and endogenous MRP mRNAs, although a difference in rates of degradation of the protein between the two cell types cannot excluded.

Figure 8A:
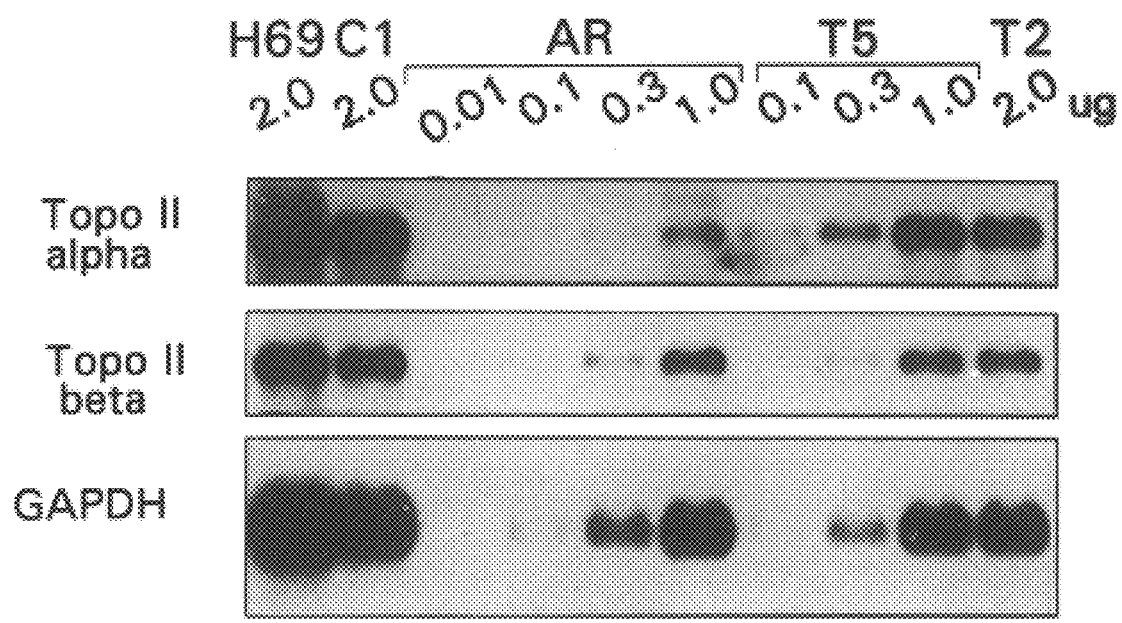
FIG. 8A is a Northern blot of poly(A)+ RNA from transfected HeLa cells and control cells hybridized with cDNA probes for topoisomerase II (Topo II) alpha and beta mRNAs. Hybridization with a GAPDH cDNA demonstrates the relative amounts of poly(A)+ RNA in each lane.
Figure 8B:
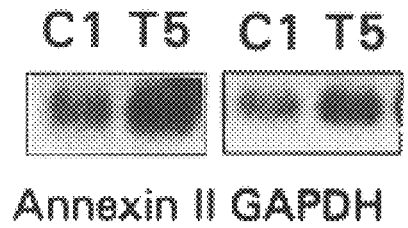
FIG. 8B is a Northern blot of poly(A)+ RNA from transfected HeLa cells and control cells hybridized with a cDNA probe for annexin II mRNA. Hybridization with a GAPDH CDNA demonstrates the relative amounts of poly (A)+ RNA in each lane.

Since H69AR cells were obtained by multistep selection, it is possible that additional alterations have occurred which may, either independently or in concert with MRP, influence their degree of resistance to some drugs. H69AR cells have been shown to have decreased levels of topoisomerase 11 α and β mRNA and protein which could enhance their resistance to anthracyclines and epipodophyllotoxins. They have also been shown to overexpress annexin 11 which may affect the trafficking of membrane proteins. Annexin 11 has been shown to be involved in formation of fusogenic vesicles and in exocytosis. S. P. C. Cole, M. J. Pinkoski, G. Bhardwaj, R. G. Deeley, Br. J. Cancer 65, 498 (1992). It is unknown to what extent these additional changes influence the degree of resistance of H69AR cells or whether they are linked in any way to overexpression of MRP. However, overexpression of MRP in the transfected cells does not alter the levels of mRNAs specifying either topoisomerase 11 isoform (FIG. 8A) or annexin 11 (FIG. 8B), nor do the transfected HeLa cells display any alterations in the level of Mdr1 mRNA. These observations strongly support the conclusion that increased resistance to doxorubicin in the transfected cells is directly attributable to overexpression of MRP.

EXAMPLE 6

Expression of MRP in a Drug Sensitive Cell Confers Multidrug Resistance on the Cell To determine whether the increased doxorubicin resistance of transfected cells was accompanied by increased resistance to other classes of chemotherapeutic drugs, the cells were tested for cross-resistance to vincristine (a Vinca alkaloid), VP-16 (an epipodophyllotoxin) and cisplatin (FIG. 9). Cytotoxicity assays were performed on untransfected HeLa cells (`), HeLa cells transfected with the expression vector pRc/CMV (C1, °), HeLa cells transfected with the expression vector pRc/CMV-MRP and maintained in G418 at 400 µg/ml for 4 months (T5, Δ), and T5 cells maintained at 800 µg/ml G418 for 1 month (T5–800/1, Δ) and 3 months (T5-800/3, □). Each point represents the mean of triplicate determinations in a single experiment and standard deviations were <5%. Similar results with vincristine and VP-16 were obtained in two to three additional experiments. The $IC_{50}$'s of the various cell lines are indicated on the figure. Dose response curves for several independently propagated cultures of MRP transfectants indicate that they are approximately 25-fold and 5- to 10-fold resistant to vincristine and VP-16, respectively, relative to untransfected HeLa cells or cells transfected with parental vector (C1). The transfectants showed no increase in cisplatin resistance which is consistent with the pharmacological phenotype of H69AR cells and which is also characteristic of cells that overexpress P-glycoprotein. These results demonstrate for the first time that this phenotype can be conferred by a member of the ABC superfamily of transporters that is structurally very different from the P-glycoproteins.

EXAMPLE 7

Preparation of Anti-MRP Antibodies Using MRP Peptides as the Immunogen

MRP is encoded by a mRNA of approximately 6.5 kb with an extended open reading frame of 1531 amino acids. The protein is predicted to contain two nucleotide binding folds (NBFs) and 12 transmembrane regions, divided 8 and 4 between the NH2- and COOH-proximal halves of the molecule, respectively. To confirm that-a protein of the predicted size and sequence is overexpressed in resistant H69AR cells, polyclonal antibodies were prepared against synthetic peptides based on the deduced amino acid sequence of MRP and used in immunoanalyses.

One peptide of sequence AELQKAEAKKEE was selected from the highly divergent cytoplasmic linker domain of MRP (MRP-L, position 932–943) while the second peptide (GENLSVGQRQLVCLA) was chosen from the second nucleotide binding domain of MRP (MRP-2, position 1427–1441). Both peptides were synthesized on Ultrasyn D resin for direct immunization by the Biotechnology Service Centre at the Hospital for Sick Children (Toronto, Ont.). Approximately 400 µg of bound peptide was resuspended in distilled water and sonicated. The resulting suspension was emulsified in an equal volume of complete Freund's adjuvant (Difco) and injected s.c. at four sites in 3-month old female New Zealand White rabbits. At 2- to 3-week intervals, the same amount of immunogen emulsified in incomplete Freund's adjuvant was injected s.c. Rabbits were bled by arterial puncture beginning 2 weeks following the third immunization and their sera were tested for the presence of antibodies by an enzyme-linked immunosorbent assay (ELISA) and by immunoblotting.

Rabbit antisera obtained after immunization with peptide MRP-L that were positive by ELISA or western blotting were concentrated by ammonium sulfate precipitation and purified by affinity chromatography. Affinity columns were constructed by coupling the MRP-L peptide to CNBr-activated Sepharose (5 µmole peptide/ml gel) according to the instructions of the supplier (Pharmacia LKB Biotechnology Inc.) followed by extensive washing with 10 mM Tris, pH 7.5. The ammonium sulfate precipitate was dissolved in phosphate-buffered saline, dialyzed extensively against the same buffer and then applied to the prewashed affinity column. The loaded column was washed first with 10 mM Tris pH 7.5 followed by 10 mM Tris, pH 7.5, 0.5 M NaCl before eluting the antibody with 0.1 M glycine, pH 2.5.

Fractions were neutralized in collection tubes containing 1 M Tris, pH 8.0. The desired fractions were pooled, dialyzed extensively against phosphate-buffered saline and concentrated by Amicon concentrators/filtration. The final protein concentration of the purified antibody was adjusted to 0.7–1.5 mg/ml. Rabbit antisera obtained after immunization with peptide MRP-2 were used without further purification.

ELISA positive antisera from these rabbits were used in immunoblot analyses. Polyacrylamide gel electrophoresis was carried out by the method of Laemmli with a 5% or 7% separating gel and a 4% stacking gel. Samples were diluted 1:1 in solubilizing buffer to a final concentration of 4 M urea, 0.5% SDS, 50 mM DTT and loaded on the gels without heating. For immunoblotting, proteins were transferred after gel electrophoresis to Immobilon-P PVDF membranes (Millipore, Mississauga. Ont.) using 50 mM CAPS, pH 11.0. Blots were incubated for 1 h in blocking solution (5% normal goat serum/5% HyClone serum/1% BSA) in TBS-T (10 mM Tris, pH 7.5, 0.05% Tween 20, 150 mM NaCl). Anti-MRP antibodies were added directly to the blocking solution and incubated for 2 h. The blot was washed 3×5 min in TBS-T and goat anti-rabbit IgG horseradish peroxidase-conjugate [affinity purified F(ab')2 fragment (Jackson ImmunoResearch) or whole molecule (ICN Biomedicals)] diluted in blocking buffer added. After a 1 h incubation, the blot was washed 5×5 min in TBS-T, and antibody binding detected by ECL (Amersham, UK) and exposure on Kodak XOMAT film. The antisera detected a 190 kD protein in resistant H69AR cells which was not detectable in sensitive H69 and revertant H69PR cells.

The antisera were also used in immunoprecipitation experiments using cell membrane preparations of cells metabolically labelled with $^{35}$S-methionine. Cells were cultured in 50 $\mu$Ci/ml $^{35}$S-methionine (Tran $^{35}$S-label; cell labelling grade; specific activity, 710 Ci/mmol) (Dupont NEN) overnight in methionine-deficient RPMI 1640 medium (Sigma) or with 500 $\mu$Ci/ml $^{32}$P-orthophosphoric acid (Carrier free, 500 mCi/ml) (Dupont NEN) in phosphate-deficient RPMI 1640 medium (ICN) for 4 h. Crude radiolabelled 100,000× g membrane-enriched fractions were prepared and immunoprecipitated as follows. Frozen or fresh cells (50×10$^6$/ml) were suspended in 10 mM Tris-HCl, pH 7.4 containing 10 mM KCl, 1.5 mM MgCl$_2$ with protease inhibitors (2 mM phenylmethylsulfonylfluoride, 50 $\mu$g/ml antipain, 2 $\mu$g/ml aprotinin, 200 $\mu$g/ml EDTA, 200 $\mu$g/ml benzamidine, 0.5 $\mu$g/ml leupeptin, 1 $\mu$g/ml pepstatin) and 0.025 mg/ml RNase A and 0.05 mg/ml DNase 1. After 10 min., the suspension was homogenized in a chilled Tenbroeck homogenizer with 80 strokes of the pestle. The homogenate was then centrifuged at 800× g at 4° C. for 15 min. to remove nuclei and remaining intact cells. A membrane-enriched fraction was prepared by ultracentrifugation of the supernatant at 100,000× g at 4° C. for 20 min. The pellets were resuspended in 10 mM Tris HCl, pH 7.6 with 125 mM sucrose and protease inhibitors as above. Protein concentrations were determined by the Peterson modification of the Lowry assay and aliquots were stored at −80° C.

Proteins were solubilized in 1% CHAPS, 100 mM KCl, 50 mM Tris-HCl, pH 7.5, at a detergent to protein ratio of 20:1 for 1 h at 4° C. with frequent vortexing followed by centrifugation at 100,000× g for 20 min using a T100.3 rotor in a Beckman Ultracentrifuge. The supernatant (whatever percentage of protein is solubilized from an initial 40 $\mu$g of membrane protein) was incubated with affinity purified MRP-L antisera (25 $\mu$g solubilized in 1% CHAPS, 100 mM KCl, 50 mM Tris-HCl, pH 7.5) overnight at 4° C. The samples were made up 700 $\mu$l with 1% CHAPS buffer then incubated with 50 $\mu$l (10% w/v) Protein A Sepharose C1-4B (Pharmacia) for 3 h at 4° C. with gentle rocking. The samples were centrifuged for 10 sec at 14,000× g and sequentially washed for 5 min with 1 ml each of Buffer 1 (10 mM Tris-HCl, pH 8.0, 0.5 mM NaCl, 0.5% Nonidet P-40, 0.05% SDS), Buffer 2 (10 mM Tris-HCl, pH 8.0, 0.15 M NaCl, 0.5% Nonidet P-40, 0.05% SDS, 0.5% deoxycholate) and Buffer 3 (10 mM Tris-HCl, pH 8.0, 0.05% SDS). The washed beads were incubated with 100 $\mu$l of 4 M urea, 0.5% SDS, 50 mM DTT for 1 h at room temperature with frequent vortexing. The samples were centrifuged and the supernatants analyzed on 7% polyacrylamide gels. The gels were fixed in isopropanol:water:acetic acid (25:65:10) for 30 min followed by the addition of the fluorographic reagent Amplify (Amersham). The gels were dried and then exposed to film overnight at −80° C. A 190 kD protein was detectable by immunoprecipitation of membrane-associated proteins from $^{35}$S-methionine labelled H69AR cells with the immunoreactive antiser.

The apparent molecular weight of the immunodetectable 190 kD protein in the H69AR cell membranes is approximately 20 kD greater than the predicted 171 kD molecular weight of MRP based upon the deduced primary amino acid sequence. However, analysis of the MRP sequence indicates the presence of three potential N-glycosylation sites in regions predicted to be asymmetrically distributed about a membrane bilayer. To determine whether or not the 190 kD protein was N-glycosylated, two sets of experiments were carried out. First, resistant H69AR cells were grown in the presence of tunicamycin, a potent inhibitor of N-linked glycosylation. N-linked glycosylation was inhibited in H69AR cells by culturing in 15 $\mu$g/ml tunicamycin (Sigma) for 24 h. Treated cells were washed twice with phosphate-buffered saline and then whole cell lysates were prepared by homogenization in lysis buffer (20 mM Tris HCl, pH 7.5, 20 mM KCl, 3 mM MgCl2. 0.5 mg/ml DNase 1, 0.25 mg/ml RNase A) with protease inhibitors as described above. Polyacrylamide gel electrophoresis and immunoblotting of the whole cell lysates were carried out as before. In the second approach, H69AR 100,000× g membranes were incubated with the deglycosylase PNGase F. Membrane-enriched fractions (200 $\mu$g protein) were diluted to a final concentration of 1 $\mu$g/$\mu$l in 50 mM Na phosphate buffer, pH 7.5, containing 25,000 NEB units PNGase F (New England Biolabs). After 8 h at 37° C., an additional 25,000 NEB units PNGase F was added followed by incubation overnight at 37° C. Sample buffer was added directly and SDS-PAGE and immunoblotting carried out as before. In both cases, a 170 kD protein was detected by immunoblot analyses which correlates well with the 171 kD predicted molecular weight of MRP. Similar results were observed with cells transfected with a full-length MRP cDNA (T5 cells) (see Almquist, et al. *Cancer Research* 55:102–110 (1995).

To confirm that MRP is an ATP-binding protein, as suggested by the presence of ATP-binding signature motifs, membranes from resistant H69AR and sensitive H69 cells were photolabelled with $^{32}$P-8-azido ATP. Crude membrane-enriched fractions were resuspended at 1 $\mu$g/$\mu$l protein in 10 mM Tris-HCl, pH 7.6, buffer containing 1 mM MgCl$_2$ and protease inhibitors as described above. After the addition of 3–4 $\mu$Ci $^{32}$P-8-azido-ATP (specific activity 2–10 Ci/mmol; ICN Biomedical, Mississauga, Ont.), incubation on ice was continued for 1–5 min. The azido-ATP was cross-linked to the protein on ice by irradiation at 366 nm about 10 cm from the light source for 8 min. using a Stratalinker set at 1100 $\mu$W. The labelled proteins were stored at −80° C. until polyacrylamide gel electrophoresis or immunoprecipitations were carried out.

Specificity of the labelling was confirmed by competition with cold excess ATP (Boehringer Mannheim, Laval, Que.) which was added to the membrane preparations prior to the addition of $^{32}$P-8-azido-ATP. These studies revealed strong, specific labelling of a 190 kD protein in membranes from the H69AR cells that was not detected in drug sensitive H69 cells. Our results indicate that in H69AR cells, the MRP gene encodes an N-glycosylated ATP-binding protein of 190 kD.

EXAMPLE 8

Preparation of Anti-MRP Monoclona Antibodies

In this Example, monoclonal antibodies reactive against MRP were prepared by immunizing mice with a multidrug resistant cell (1169AR) that expresses MRP followed by isolation of antibody-producing cells, fusion with immortalized cells and selection of specific monoclonal antibodies. The following methodologies were used:

Cell Culture

The parental H69, doxorubicin-selected multidrug resistant H69AR, and revertant H69PR small cell lung cancer cell lines were maintained as described in Mirski, S. E. L. et al. (1987) *Cancer Res.* 47:2594–2598; Cole, S. P. C. et al. (1992) *Br. J. Cancer* 6:498–502. T5 cells (HeLa cells that have been made multidrug resistant by transfection with a full length MRP cDNA expression vector, pRc/CMVMRP1) and C1 cells (HeLa cells that have been transfected with pRc/CMV vector alone). were maintained in the same medium as the lung cancer cells, supplemented with 400 µg/ml G-418 (Sigma Chemical Co., St. Louis, Mo.). SP2/0Ag14 myeloma cells (ATCC# CRL 1581) were maintained in DMEM (Hybri-Max, Sigma) supplemented with 4 mM L-glutamine and 5% heat inactivated bovine calf serum. Approximately one week prior to fusion, Sp2/0 cells were challenged with 0.132 mM 8-azaguanine (Sigma) for one passage.

Generation of Hybridomas

Membrane-enriched cell fractions were prepared and resuspended in Tris-sucrose buffer (10 mM Tris HCl, pH 7.5, 0.25 M sucrose) containing protease inhibitors. Female BALB/c mice (6–8 weeks old) received three i.p. injections of 150 µg H69AR membrane protein (without detergent) in PBS and mixed 1:1 with an emulsion of monophosphoryl lipid A (MPL), synthetic trehalose dicorynomycolate (TDM) and cell wall skeleton (CWS) (obtained commercially from RIBI ImmunoChem Research, Inc., Hamilton, Mont.) at approximately three week intervals. Three days before fusion, 100 µg H69AR membrane protein was injected i.v. into a tail vein. Spleen cells were fused with SP2/0 myeloma cells with polyethylene glycol 4000 (Sigma Chemical Co., St. Louis, Mo.) according to standard methods (see e.g., Kennett, R. H. (1979) *Meth. Enzymol.* 58:345–359; Mirski, S. E. L. et al. (1989) *Cancer Res.* 49:5719–5724). Cultures were fed with DMEM medium containing 100 µM hypoxanthine, 0.4 µM aminopterin, 16 µM thymidine, 20% heat-inactivated fetal bovine serum and gentamycin (25 µg/ml) (ICN Biomedicals, St. Laurent, Quebec, Canada). After initial screening, aminopterin was omitted from the growth medium.

Screening, Cloning, Isotyping and Ascites Production

After 11 days of growth in selective medium, 459 hybridoma supernatants were tested for the presence of MRP-specific antibody by immunodot blot analysis. H69, H69AR, and H69PR membrane proteins in TBS were blotted (4 µg protein/dot) onto Immobilon-P PVDF membrane (Millipore, Mississauga, Ontario, Canada) using a 96-well vacuum manifold and blots were kept wet at all times. The blots were cut into strips such that each strip had spots of membrane proteins from each of the three cell lines. After transfer to 24-slot incubation trays, strips were blocked for 1 h in blocking solution (5% bovine calf serum/5% normal goat serum/1% BSA in TBS-T). Hybridoma supernatants were added directly to the blocking solution at a final dilution of 1:9. After 90 min, the strips were washed 3×5 min in TBS-T, and secondary antibody (horseradish peroxidase-conjugated goat anti-mouse IgG+IgM (H+L), F(ab')2 fragment) (Pierce, Edmonton, Alberta) was added (diluted 1:10,000 in blocking buffer). After 1 h, the strips were washed 5×5 min in TBS-T, and antibody binding was determined by enhanced chemiluminescence detection (Amersham, Oakville, Ontario, Canada) and exposure on Kodak X-OMAT film.

Hybridomas which showed preferential reactivity with H69AR membrane dots were subjected to a second immunodot blot, using strips with C1 and T5 membrane protein dots in addition to the H69, H69AR, and H69PR dots. Hybridomas which reacted preferentially with H69AR and T5 membrane dots compared to H69, H69PR, and C1 dots were cloned twice by limiting dilution and then expanded.

Immunoglobulin subtypes of the MAbs produced by the five stable hybridoma clones obtained were determined using an isotyping reagent kit (Sigma). To produce ascites, $5 \times 10^6$ hybridoma cells resuspended in PBS were injected i.p. into pristane-pretreated BALB/c (nu/nu) mice. Ascites fluid was collected over the next 1–2 weeks and MAbs were purified by passage over Econo-Pac DEAE Blue cartridges (BioRad, Mississauga, Ontario, Canada) according to manufacturer's instructions.

Immblotting and Immunoprecipitation of MRP

Membrane protein was solubilized in Laemmli buffer (Laemmli, U.K. (1970) *Nature* 227:680–685), and subjected to SDS-PAGE and electroblotting by standard methods. Immunoblotting was performed as described above for dot blot strips. For H69, H69AR and H69PR membrane proteins, 2.5 µg/dot were used. For C1 and T5 membrane proteins, 5 µg/dot were used. The blots were incubated with hybridoma supernatants or with an anti-P glycoprotein mAb, C219 (Centocor, Malvern, Pa.; used at 1 µg/ml). In some experiments, a polyclonal antiserum (MRP-2) that was raised against a peptide corresponding to amino acids 1418 to 1432 of MRP, and which is known to cross-react with P-gp, was used as a positive control for MRP detection.

Immunoprecipitations were carried out as follows. Cells were incubated for 24 h in L-methionine-deficient RPMI 1640 medium (Sigma) supplemented with 10% dialyzed bovine calf serum and 50 µCi/ml [$^{35}$S]methionine (1110 Ci/mmol, cell labelling grade) (Dupont NEN, Markham, Ontario, Canada). Cells were washed twice with PBS and resuspended at approximately $6 \times 10^7$ cells/ml in solubilizing buffer (1% CHAPS, 100 mM KCl, 50 mM Tris-HCl, pH 7.5) containing protease inhibitors. After 1 h on ice, insoluble matter was removed by ultracentrifugation. Aliquots of the supernatant were brought up to 250 µl with solubilizing buffer, and incubated for at least 2 h at 4° C. with hybridoma supernatant diluted 1:6. Antibody-MRP complexes were recovered by incubation with 25% w/v GammaBind Plus Protein G Sepharose (30 µl) or 10% w/v Protein A Sepharose CL-4B (25 µl) (Pharmacia, Baie D'Urfe, Quebec, Canada) in solubilization buffer for at least 2 h at 4° C. The samples were sequentially washed and precipitated proteins were eluted from the beads with Laemmli buffer and analyzed by SDS-PAGE and fluorography.

Indirect Immunofluorescence and Flow Cytometry

Cells were washed twice with cold PBS and fixed with either 0.5% paraformaldehyde (Sigma) in PBS for 30 min at 4° C. or with 70% methanol at −20° C. for 10 min. All subsequent procedures were done at 4 ° C. Cells were washed once with blocking solution (1% BSA/5% normal goat serum/PBS). For MAbs QCRL-2 and QCRL-3, the cells were incubated in blocking solution with 0.1% Triton X-100 for 30 min, followed by direct addition of hybridoma supernatant or ascites diluted as required. After incubation for 1 h, the cells were washed once in blocking solution with 0.1% Triton X-100 followed by a wash in blocking solution alone. The washed cells were incubated with fluorescein-conjugated goat anti-mouse IgG (H+L) F(ab')2 fragment (Pierce) diluted 1:50 in blocking solution for 30 min, and then washed twice in blocking solution with 0.1% Triton X-100. For MAb QCRL-1, cells were treated similarly except Tween-20 was used at 0.1% instead of Triton X-100, and was included in all washes and incubations. Finally, cells were resuspended in 1% paraformaldehyde in PBS and either analysed on a Coulter Epic flow cytometer or cytospins were prepared for examination by fluorescence microscopy.

RESULTS

Using spleens from mice immunized with MRP-enriched membranes, murine hybridomas were generated and screened for their ability to detect MRP in non-denatured membranes. Five stable cloned hybridoma cell lines, designated QCRL-1, QCRL-2, QCRL-3, QCRL-4, and QCRL-6, were obtained.

Figure 10:
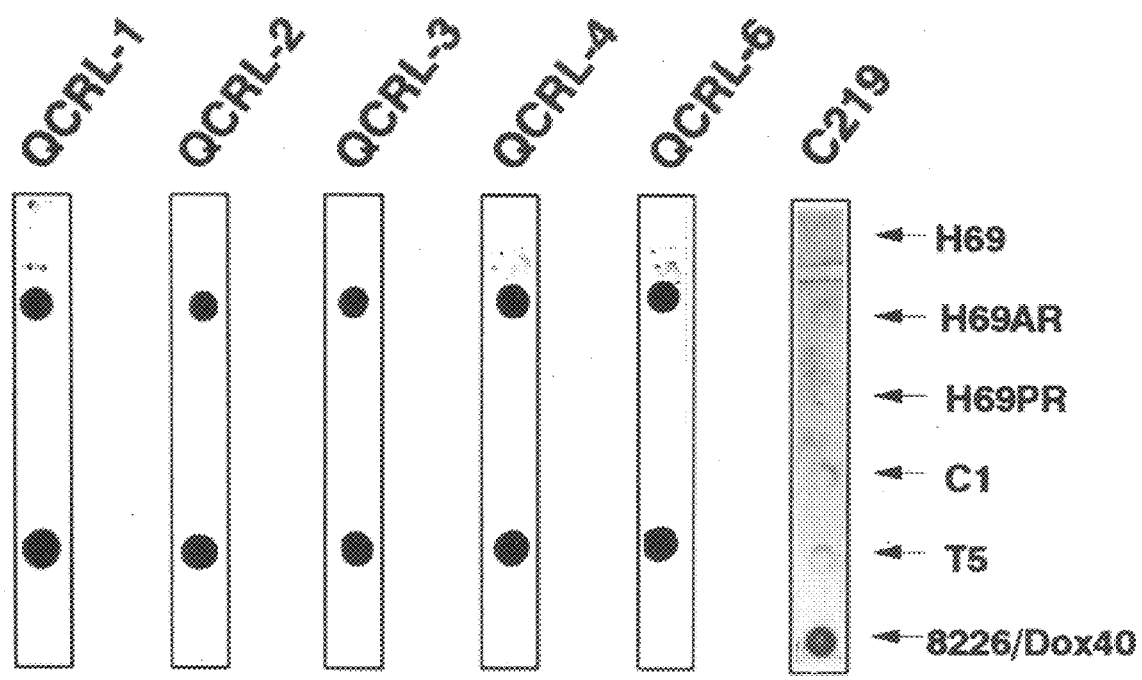
FIG. 10 is a photograph of immunodot blots of MRP-overexpressing cells (H69AR and T5), P-glycoprotein-overexpressing cells (8226/Dox40) or control cells (H69, H69PR and C1) screened with anti-MRP mAbs (QCRL-1, -2, -3, -4 or -6) or an anti-Pgp mAb (C219).

MAbs QCRL-1, QCRL-4, and QCRL-6 were determined to be of the IgG, subclass, MAb QCRL-2 was an IgG2b, and MAb QCRL-3 was an IgG2a. The MAbs reacted strongly with MRP-rich membrane fractions from both drug-selected H69AR cells and MRP-transfected T5 cells and weakly or not at all with parental H69, revertant H69PR and control C1 cell membranes (see the immunoblot analysis shown in FIG. 10). None of the MAbs cross-react with P-gp, since they showed no reactivity with membrane fractions from 8226/Dox40 cells which are known to overexpress this 170 kDa protein and which reacted with the P-gp-specific MAb C219.

To confirm the MRP-specificity of these MAbs, immunoprecipitation and immunoblot analyses were carried out. MAb QCRL-3 immunoprecipitated a single 190 kDa protein from [35S]methionine-labelled H69AR cells when protein A was used to bind immune complexes (see FIG. 11A). MAb QCRL-2 also precipitated this 190 kDa protein. This precipitated protein had the same electrophoretic mobility as the protein precipitated by the polyclonal antiserum MRP-2 which was raised against an MRP-derived peptide. To immunoprecipitate MRP with MAb QCRL-1, protein G was required to bring down immune complexes (see FIG. 11B). Protein G was also effective in precipitating MRP with MAbs QCRL-2 and QCRL-3. A 190 kDa protein was precipitated with all three MAbs from the MRP-transfected T5 cells but not from C1 control cells. Taken together, these data provide confirmation of the MRP-specificity of MAbs QCRL-1, -2 and -3.

Immunoblot analyses (Western blots) with the MAbs were carried out under both reducing and non-reducing conditions. The results for reducing conditions are shown in FIG. 12A–C. In panels A and C, 5 µg of H69, H69AR or H69PR protein were used, 10 µg T5 or C1 protein were used, and 25 µg 8226/Dox40 protein were used. In panel B, 15 µg T5 protein were used and 75 µg of H69PR protein were used.

As shown in FIGS. 12A and B, MAb QCRL-1 detected a protein of 190 kDa. This protein is easily detectable at high levels in membranes from H69AR and T5 cells using QCRL-1 hybridoma supernatant and the relative levels in the two cell types are approximately the same as those observed using MRP-specific polyclonal antisera. The very low levels of the 190 kDa protein found in the drug-sensitive revertant H69PR cells could also be detected with a very high degree of specificity using MAb QCRL-1 ascites (see FIG. 12B). The 170 kDa P-gp, detectable in 8226/Dox40 cells with MAb C219 (see FIG. 12C), was not detected in immunoblots with MAb QCRL-1, consistent with the immunodot blot analyses.

Figure 13:
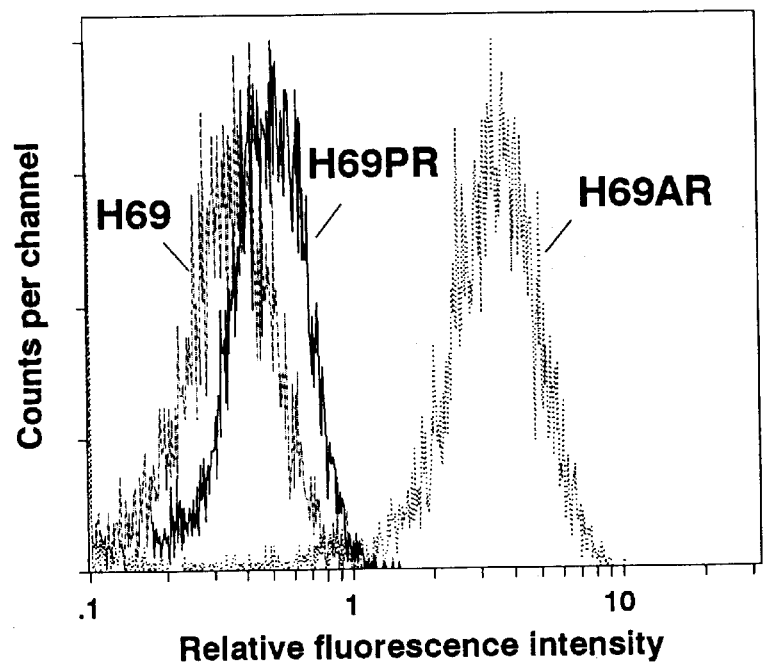
Figure 13:
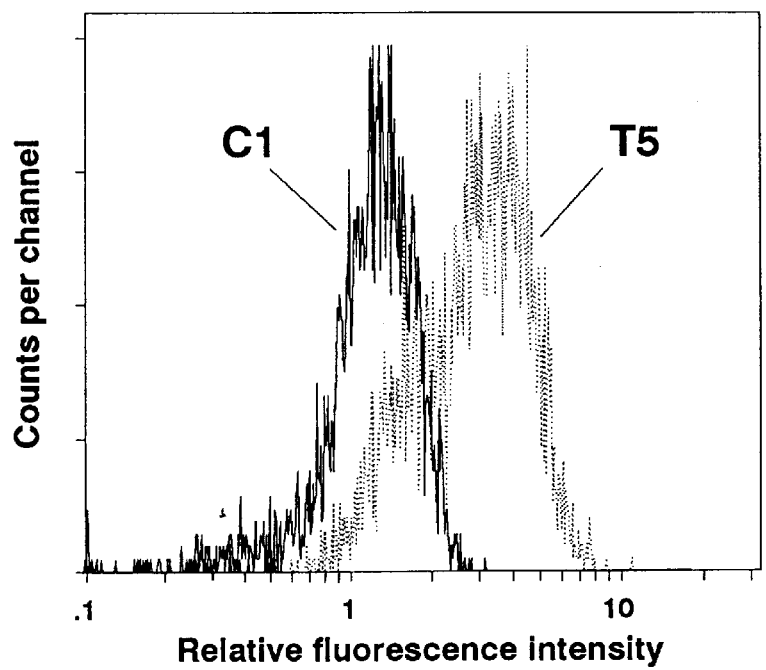

To demonstrate that MRP-specific MAbs are able to recognize MRP epitopes in fixed cells and tissues, labelling of H69, H69AR, H69PR, C1, and T5 cells with MAbs QCRL-1, QCRL-2 and QCRL-3 was examined by flow cytometry and indirect immunofluorescence microscopy. None of the MAbs reacted with unfixed cells, suggesting that the MRP epitopes detected by these MAbs are not exposed on the cell surface. However, the epitopes recognized by these three MAbs remained intact after fixation of cells with either 0.5% paraformaldehyde or 70% methanol. MRP reactivity with MAbs QCRL-1 and QCRL-3 also remains intact after fixation with 10% formalin. Representative flow cytometry histograms obtained with MAb QCRL-3 and cells fixed with 0.5% paraformaldehyde are shown in FIGS. 13, panels A and B. MAb QCRL-3 clearly discriminated between H69AR cells, in which high levels of MRP are detected in essentially all cells, and parental H69 cells, in which the 190 kDa protein is not detected. A small difference in immunofluorescent labelling was also observed between the parental H69 cells and revertant H69PR cells, which express slightly higher levels of MRP than H69 cells. When MRP-transfected T5 cells were labelled with MAb QCRL-3, an asymmetric distribution of relative fluorescence intensity was observed. Since T5 cells are an uncloned population, individual cells within this population are likely to express different levels of MRP. Similar histograms were obtained with MAbs QCRL-1 and QCRL-2.

Using indirect immunofluorescence microscopy, all three MAbs were observed to react intensely with resistant T5 and H69AR cells but not with C1 and H69 cells. Labelling of H69AR cells was uniform while staining of T5 cells was somewhat heterogeneous, consistent with the flow cytometric analyses. Both MRP positive T5 cells and H69AR cells showed predominantly plasma membrane labelling. These data are consistent with subcellular fractionation studies which also indicate a predominantly plasma membrane localization of MRP in these cells. However, some granular cytoplasmic staining was also evident in the T5 and H69AR cells, suggesting that some MRP may be associated with intracellular membranes.

In an attempt to generate mAbs reactive against conformational epitopes of MRP, denaturing detergents were not used in the preparation of the membranes used for immunization and or in the immunodot blotting screening procedure. Only one of the five MAbs obtained, MAb QCRL-1, recognizes a linear epitope, as demonstrated by its reactivity with denatured protein in immunoblots. In contrast, the other four MAbs only detect MRP in non-denaturing immunodot blots or under relatively non-denaturing conditions in immunoprecipitations, and in fixed cells. These observations strongly suggest that these latter MAbs recognize conformation dependent epitopes. Because of its unique ability to detect MRP in immunoblots, it may be inferred that MAb QCRL-1 reacts with an MRP epitope distinct from those recognized by the other four MAbs. The ability of MAbs QCRL-2 and QCRL-3 to immunoprecipitate MRP, while MAbs QCRL-4 and QCRL-6 are unable to do so under the same conditions, suggests that these two pairs of MAbs also recognize at least two different epitopes.

EXAMPLE 9
Isolation of a Mouse MRP-Encoding cDNA

In this Example, an MRP-encoding cDNA was isolated from a mouse cDNA library. The following methodologies were used:

Cloning and Sequence Analysis of Murine MRP

A mouse skeletal muscle 5'-stretch plus cDNA Library (Clontech Laboratories, Inc., Palo Alto, Calif.) was screened as described in Sambrook et al. (1989) *Molecular Cloning: A Laboratory Manual,* 2nd edition, Cold Spring Harbor Press, Cold Spring Harbor, N.Y., using a mouse genomic DNA fragment which was isolated previously from a 129SV-CP mouse genomic library using a human MRP cDNA as a probe. The murine genomic fragment contained an exon corresponding to exon 2 of the human MRP gene. The muscle cDNA library was also screened with a 3' proximal cDNA fragment corresponding to nucleotides 4080 to 5011 of the human MRP mRNA. Approximately $5 \times 10^5$ plaques were screened and 4 positive cDNA clones were selected and plaque purified (clones 14B, 16, 37 and 41). The cDNA inserts of clones 14B (nucleotides 124 to 2111), 16 (nucleotides 1607 to 5888) and 41 (nucleotides 2796 to 5883) were subcloned into a pBluescript vector (Stratagene) and both strands were sequenced using the dideoxy chain termination method and Sequenase version 2.0 (U.S. Biochemicals)

Polymerase Chain Reaction (PCR) Methods

Standard PCR conditions were used to amplify regions of the isolated cDNAs for sequencing (clone 37 nucleotides 1 to 146) or for use as probes in Southern blot analysis. Reverse transcriptase (RT)-PCR using Poly A+ RNA isolated from the L138C3-109 murine mastocytoma cell line was used to confirm the sequence of some regions of the MRP mRNA.

Genomic DNA Preparation and Southern Blot Analysis

Genomic DNA was isolated from CD1 mice, digested with EcoR1 and subjected to agarose gel electrophoresis. DNA was transferred to Zetaprobe membrane (Biorad, Mississuaga, Ontario, Canada), and cross-linked using a W Stratalinker (Stratagene). The blot was prehybridized at 37° C. for 4–6 h in 50% formamide, 5× SSPE, 4× Denhardt's, 0.5% SDS and 100 μg/ml sheared and denatured herring testes DNA. It was then hybridized under the same conditions for 12–16 h with a [γ-$^{32}$P]dATp-labelled MRP cDNA fragment, and subsequently washed four times for 15 min in 2× SSC and 0.1% SDS at 42 ° C. In some experiments, higher stringency washes were also carried out in 2× SSC or 0.1× SSC and 0.1% SDS at 52° C.

RNA Isolation and Northern Blot Analysis

Total RNA was obtained using TRIzoL reagent (Gibco BRL, Toronto, Ontario, Canada), from various tissues dissected from sexually mature CD1 mice as well as the murine mastocytoma L138C3-109 cells and HeLA cells (T5) transfected with a human MRP expression vector. PolyA enriched RNA was subsequently isolated from the total RNA using either a PoLyATtract mRNA isolation system (Promega, Madison, Wis.) or a Micro-FastTrack RNA isolation kit (Invitrogen, San Diego, Calif.). RNA was separated by electrophoresis on formaldehyde-agarose denaturing gels (Fourney, R. M. et al. (1988) *Focus* 10:5–7), blotted, prehybridized at 42° C. for 4–6 h and hybridized at 42° C. for 12–16 hours with [γ-$^{32}$P]-cDNA fragments under standard conditions (NEN Products, Boston, Mass.). The blot was washed four times with 0.1× SSC and 0.1% SDS for 15 min at 52° C. and then exposed to film. Blots were subsequently hybridized without stripping with cDNAs corresponding to glyceraldehyde-3-phosphate dehydrogenase (GAPDH) and/or β-actin. Relative levels of MRP and β-actin were determined by densitometric analysis of the autoradiographs (Molecular Dynamics, Sunnyvale, Calif.).

In Situ Hybridization

Single stranded antisense RNA probes were produced by run-off in vitro transcription in the presence of digoxygenin-UTP (Boehringer-Mannheim). The template for the MRP probe was a 1593 bp EcoRI-SacI fragment of clone 14B which corresponds to nucleotides 119 to 1610 of the murine mRNA, subcloned in pBluescript II SK+ (Stratagene). As a control, tissue sections were hybridized with an antisense probe complementary to the coding region of rabbit β-globin. Cryosections (6–8 μm) were mounted onto poly-L-lysine coated glass microscope slides, fixed for 1 h in 4% paraformaldehyde, treated with proteinase K (1 μg/l for 10–20 min), and post-fixed in 4% paraformaldehyde for 20 min, before being hybridized overnight in 50% formamide, 5× SSC, 0.5 mg/ml tRNA, 0.005% heparin, 0.1% Tween-20 and 250 μg/ml denatured herring testes DNA. The next day the slides were washed twice in 2× SSC for 30 min each, at room temperature and once for 30 min at 65° C., followed by a 30 min high stringency wash at 65° C. in 0.1× SSC/0.1% SDS.

Unhybridized probe still remaining was removed by 30 min digestion with 20 μg/ml RNase A (Pharmacia) at 37° C., followed by 15 min in 2× SSC/0.1% SDS at 65° C., and 30 min in 1× SSC/0.1% SDS at 65 ° C. Hybridized probe was detected with an alkaline phosphatase conjugated sheep anti-digoxigenin antibody (Boehringer-Mannheim) and the chromogenic substrates nitro blue tetrazolium and 5-bromo-4-chloro-3-indolyl-phosphate.

Molecular Cloning of a Mouse MRP cDNA

Preliminary Northern blotting analyses of RNA from a number of murine tissues was carried out to identify an appropriate source from which to clone the murine MRP homologue. Analyses using a human MRP cDNA probe revealed a single cross-hybridizing mRNA species of 6.0–6.4 kb that was present at relatively high levels in skeletal muscle. A mouse skeletal muscle cDNA library was then screened to isolate clones containing cDNA fragments corresponding to the cross-hybridizing murine mRNA. The first probe used for screening was a DNA fragment isolated from a 129SV-CP mouse genomic library that contained a putative exon which was 90% identical to nucleotides 48 to 226 of the coding region of human MRP mRNA. The second was a 3' proximal human cDNA fragment encompassing nucleotides 3881 to 4815 of the MRP mRNA. Sequencing of the 4 cDNA clones isolated revealed a potential open reading frame of 1528 amino acids which was 88% identical with the coding sequence of the human MRP mRNA. This open reading frame was interrupted in one clone by a stretch of 65 nucleotides bracketed by potential intron acceptor and donor sites. The region spanning the possible intron was amplified by RT-PCR using RNA from a mouse mastocytoma cell line which has been shown previously to express relatively high levels of MRP. Sequencing of the RT-PCR product confirmed that the additional sequence present in clone 14B was not present in the majority of the mRNA and most probably represents an unspliced intron. The most 5' proximal of the clones isolated, clone 37, contained a methionine codon at a position corresponding to the initiator methionine of human MRP plus 5 nucleotides of 5' untranslated sequence. In addition to an open reading frame of 1528 amino acids, the compiled sequence contained a 3' untranslated region of 1295 nucleotides. The nucleotide and encoded amino acid sequences of the isolated mouse MRP cDNA clone are shown in SEQ ID NOs: 5 and 6, respectively.

Comparison of Mouse and Human MRP Amino Acid Sequences

The deduced amino acid sequences of the murine protein and human MRP are 88% identical. The sequences of predicted Walker A and B motifs in both the $NH_2$-and COOH-proximal nucleotide-binding folds (NBF) of the two proteins was completely conserved, as is the atypical spacing of these motifs in the $NH_2$-proximal domain. The highest variability in amino acid sequence between human MRP and the cloned murine mRNA was found to occur in the linker region which joins the two functional halves of the molecule. The most striking similarity found between murine and human MRP was the complete conservation of 114 amino acids between positions 1123 and 1236 of the murine MRP coding sequence and positions 1126 and 1139 of the human MRP coding sequence.

Analysis of the Tissue Distribution of Murine MRP mRNA

Using clone 16 as a probe, an mRNA of approximately 6–6.4 kb was detected at variable levels in all tissues examined. The highest levels of expression were in testes, lung, kidney, heart and skeletal muscle. The murine mRNA was detectable in liver only when the quantity of liver Poly A+mRNA was increased 4-fold. This tissue profile of expression is similar to that of human MRP. The spatial pattern of expression of the cloned murine mRNA in testis and lung was also analyzed by in situ hybridization. In the testis, detection of the mRNA was restricted to germ cells. Examination of cross sections of the testis revealed that positive staining was confined to seminiferous tubules. It was also observed at low magnification that only a subset of the seminiferous tubules was stained and that staining intensity within this subset was highly variable. On the basis of their location within the seminiferous epithelium, the positively staining cells were identified as haploid spermatids. The pattern of mRNA localization observed herein indicates that expression is developmentally regulated in the testis, and that spermatogenic cells accumulate the mRNA in a stage specific fashion. The expression of the cloned murine MRP mRNA in spermatids suggests a role in the dramatic morphogenetic transformation that takes place during spermiogenesis.

In the lung high levels of the cloned murine MRP mRNA were detected in the epithelia lining both bronchi and bronchioles.

Identical results were obtained when hybridization was carried out with another of the isolated cDNAs as a probe, corresponding to a region of the transcript distinct from 14B. The specificity of the staining pattern was also assessed by hybridization with the rabbit β-globin probe. This resulted in only a low level of background staining, without any discernible pattern, in both testis and lung.

Genomic Southern Blot Analysis

To look for the existence of other genes closely related to the gene from which the murine mRNA was transcribed Southern blot analysis was performed with mouse genomic DNA. This was performed under low stringency conditions using a PCR product encompassing nucleotides 53 to 231 of the coding sequence of the murine mRNA as a probe. Since the probe did not contain any EcoR1 restriction sites and there are no EcoR1 restriction sites in the murine mRNA coding sequence, the genomic fragment(s) recognized by the probe would have been generated by cleavage within intron sequence. Conservation of restriction sites in intron sequence among closely related family members is unlikely, indicating that should a family of genes exist, the probe would have been expected to hybridize to more than one fragment under the conditions used. However, the probe hybridized to a single discrete fragment in an EcoR1 genomic digest suggesting that in contrast to the murine Pgps, the isolated murine mRNA does not belong to a multigene family.

Forming part of the present disclosure is the appended Sequence Listing for the multidrug resistance proteins of the present invention.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method for identifying a substance which is a chemosensitizer of a therapeutic agent, comprising:
    contacting a cell with the therapeutic agent in vitro, wherein the cell is transfected with a nucleic acid molecule that hybridizes under high stringency conditions to a nucleic acid encoding a protein having the amino acid sequence shown in SEQ ID NO: 2, wherein the nucleic acid molecule is expressed in the cell and confers multidrug resistance upon the cell;
    determining resistance of the cell to the therapeutic agent when incubated with and without a test substance; and
    identifying a substance which is a chemosensitizer of a therapeutic agent by the ability of the substance to decrease the resistance of the cell to the therapeutic agent when incubated with the substance as compared to the resistance of the cell to the therapeutic agent when incubated without the substance.

2. The method of claim 1, wherein the nucleic acid molecule comprises the coding region of a nucleotide sequence selected from the group consisting of SEQ ID NO: 1, SEQ ID NO: 3 and SEQ ID NO: 5.

3. The method of claim 1, wherein the nucleic acid molecule encodes a protein having an amino acid sequence selected from the group consisting of SEQ ID NO: 2, SEQ ID NO: 4 and SEQ ID NO: 6.

4. The method of claim 1, wherein the nucleic acid molecule comprises a recombinant expression vector.

5. The method of claim 1, wherein the cell is sensitive to the therapeutic agent prior to transfection with the nucleic acid molecule.

6. The method of claim 1, wherein the therapeutic agent is selected from the group consisting of anthracyclines, epipodophyllotoxins and Vinca alkaloids.

7. A method for identifying a substance which is cytotoxic to a multidrug resistant cell, comprising:
    contacting a multidrug resistant cell with the substance in vitro wherein the cell is transfected with a nucleic acid molecule that hybridizes under high stringency conditions to a nucleic acid encoding a protein having the amino add sequence shown in SEQ ID NO: 2, wherein the nucleic acid molecule is expressed in the cell and confers multidrug resistance upon the cell; and
    determining cytotoxicity of the substance for the multidrug resistant cell to identify a substance which is cytotoxic to the multidrug resistant cell.

8. The method of claim 7, wherein the nucleic acid molecule comprises the coding region of a nucleotide sequence selected from the group consisting of SEQ ID NO: 1, SEQ ID NO: 3 and SEQ ID NO: 5.

9. The method of claim 7, wherein the nucleic acid molecule encodes a protein having an amino acid sequence selected from the group consisting of SEQ ID NO: 2, SEQ ID NO: 4 and SEQ ID NO: 6.

10. The method of claim 7, wherein the nucleic acid molecule comprises a recombinant expression vector.

11. A method for identifying a substance which is a chemosensitizer of a therapeutic agent, comprising:
    contacting with a cell with the therapeutic agent in vitro, wherein the cell is transfected with a nucleic add molecule that hybridizes under high stringency conditions to a nucleic acid encoding a protein having the amino acid sequence shown in SEQ ID NO: 2, wherein the nucleic acid molecule is expressed in the cell and confers multidrug resistance upon the cell;
    determining resistance of the cell to the therapeutic agent when incubated with and without a test substance; and
    identifying a substance which is a chemosensitizer of a therapeutic agent by the ability of the substance to decrease the resistance of the cell to the therapeutic agent when incubated with the substance as compared to the resistance of the cell to the therapeutic agent when incubated without the substance, wherein the identified substance which is a chemosensitizer does not substantially reverse P-glycoprotein-mediated multidrug resistance.

12. A method for identifying a substance which is cytotoxic to a multidrug resistant cell, comprising:
    contacting a multidrug resistant cell with the substance in vitro, wherein the cell is transfected with a nucleic acid molecule that hybridizes under high stringency conditions to a nucleic acid encoding a protein having the amino add sequence shown in SEQ ID NO: 2, wherein the nucleic acid molecule is expressed in the cell and confers multidrug resistance upon the cell; and
    determining cytotoxicity of the substance for the multidrug resistant cell to identify a substance which is cytotoxic to the multidrug resistant cell, wherein the identified substance does not substantially reverse P-glycoprotein-mediated multidrug resistance.

13. A method for identifying a substance which is a chemosensitizer of a therapeutic agent, comprising:
    contacting a cell with the therapeutic agent in vitro, wherein the cell transfected with a nucleic acid molecule encoding a protein having the amino acid sequence shown in SEQ ID NO: 2 or SEQ ID NO: 4, wherein the nucleic acid molecule is expressed in the cell;
    determining resistance of the cell to the therapeutic agent when incubated with and without a test substance; and
    identifying a substance which is a chemosensitizer of a therapeutic agent by the ability of the substance to decrease the resistance of the cell to the therapeutic agent when incubated with the substance as compared to the resistance of the cell to the therapeutic agent when incubated without the substance.

14. The method of claim 13, wherein the identified substance which is a chemosensitizer does not substantially reverse P-glycoprotein-mediated multidrug resistance.

15. A method for identifying a substance which is cytotoxic to a multidrug resistant cell, comprising:

contacting a multidrug resistant cell with the substance in vitro, wherein the cell is transfected with a nucleic acid molecule encoding a protein having the amino add sequence shown in SEQ ID NO: 2 or SEQ ID NO: 4, wherein the nucleic acid molecule is expressed in the cell; and determining cytotoxicity of the substance for the multidrug resistant cell to identify a substance which is cytotoxic to the multidrug resistant cell.

16. The method of claim 15, wherein the identified substance does not substantially reverse P-glycoprotein-mediated multidrug resistance.

* * * * *

UNITED STATES PATENT AND TRADEMARK OFFICE
CERTIFICATE OF CORRECTION

PATENT NO. : 6,001,563
DATED : December 14, 1999
INVENTOR(S) : Roger G. Deeley and Susan P.C. Cole It is certified that error appears in the above-identified patent and that said Letters Patent is hereby corrected as shown below:

At column 4, line 56; "Figure 3A is" should be --Figures 3A-1 to 3A-5 show--.

At column 4, line 59; "Figure 3B is" should be --Figures 3B and 3B-1 show--.

Figure 9A:
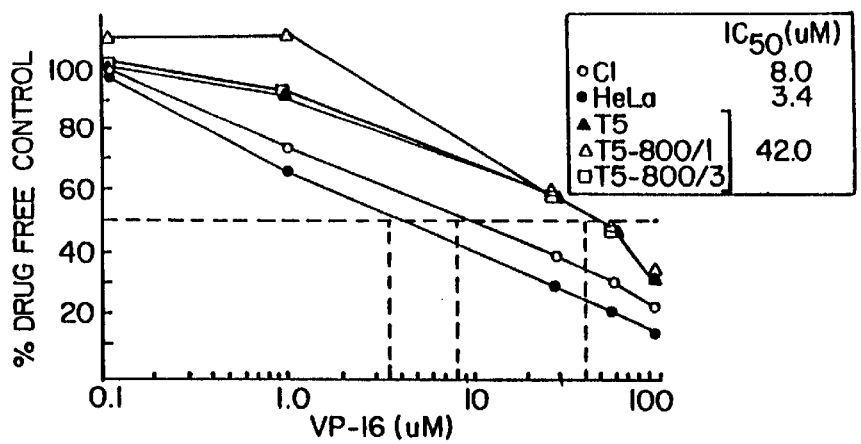
FIG. 9 is a graph depicting the relative cytotoxicity of VP-16, vincristine and cisplatin on MRP-transfected HeLa cell populations (T2, T5), a clone of the T5 population (T5-5), untransfected HeLa cells and HeLa cells transfected with the parental expression vector (C1).
Figure 9B:
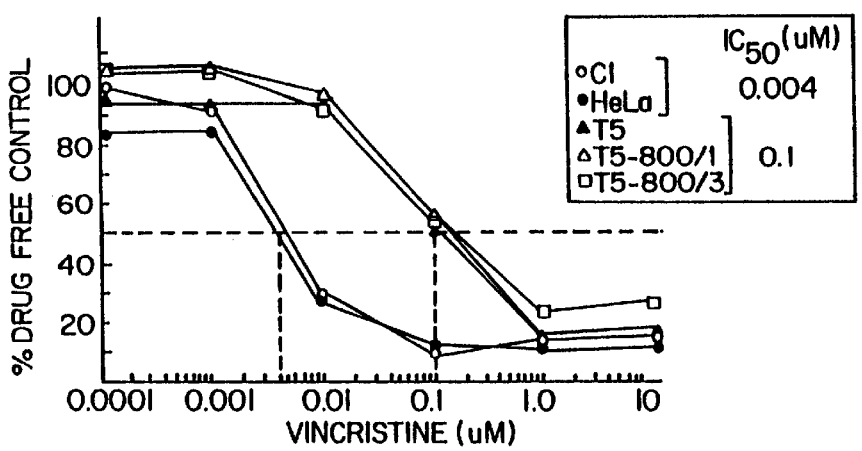
Figure 9C:
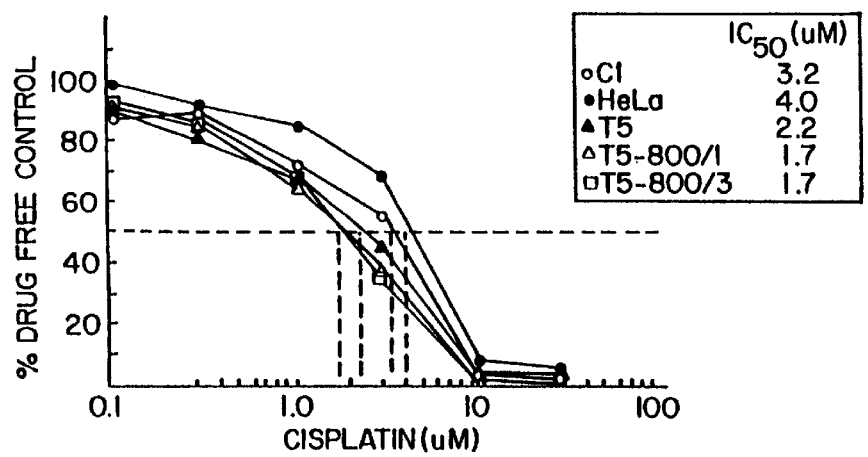

At column 5, line 37; "Figure 9 is a graph depicting" should be --Figures 9A to 9C show--.

At column 5, line 38; "cisplatin" should be --cisplatin, respectively,--.

At column 5, line 39; "(T2, T5)" should be --(T5-800/1, T5-800/3)--.

At column 5, line 40; "(T5-5)" should be --(T5)--.

At column 34, line 13; "(Figure 3A)" should be --(Figures 3A-1 to 3A-5)--.

At column 34, line 20; "Figure 3A" should be --Figures 3A-1 to 3A-5--.

At column 34, line 40; "Figure 3B" should be --Figures 3B and 3B-1-- (both occurrences).

At column 34, line 49; "Figure 3A" should be --Figures 3A-1 to 3A-5--.

At column 39, line 64; "cross-resistance to" should be --cross-resistance to VP-16 (an epipodophyllotoxin),--.

At column 39, line 65; "alkaloid), VP-16 (an epipodophyllotoxin) and" should be --alkaloid), and--.

At column 39, line 66; "(Figure 9)" should be --(Figures 9A to 9C)--.

At column 40, line 3; "Δ" should be --▲--.

In claim 7, at column 105, line 50; "vitro wherein" should be --vitro, wherein--.

In claim 7, at column 105, line 53; "add" should be --acid--.

In claim 11, at column 106, line 18; "add" should be --acid--.

In claim 12, at column 106, line 40; "add" should be --acid--.

In claim 13, at column 106, line 52; "cell transfected" should be --cell is transfected--.

UNITED STATES PATENT AND TRADEMARK OFFICE
CERTIFICATE OF CORRECTION

PATENT NO. : 6,001,563
DATED : December 14, 1999
INVENTOR(S) : Roger G. Deeley and Susan P.C. Cole It is certified that error appears in the above-identified patent and that said Letters Patent is hereby corrected as shown below:

In claim 15, at column 107, line 5; "add" should be --acid--.

Signed and Sealed this

Nineteenth Day of September, 2000

Attest:

Q. TODD DICKINSON

Attesting Officer   Director of Patents and Trademarks

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 5011 base pairs (B) TYPE: nucleic acid
            (C) STRANDEDNESS: double
            (D) TOPOLOGY: linear (ii) MOLECULE TYPE: cDNA (ix) FEATURE:
            (A) NAME/KEY: CDS
            (B) LOCATION: 196..4788

(xi) SEQUENCE DESCRIPTION: SEQ ID NO:1:

```
CAGGCGGCGT TGCGGCCCCG GCCCCGGCTC CCTGCGCCGC CGCCGCCGCC GCCGCCGCCG    60

CCGCCGCCGC CGCCGCCAGC GCTAGCGCCA GCAGCCGGGC CCGATCACCC GCCGCCCGGT   120

GCCCGCCGCC GCCCGCGCCA GCAACCGGGC CCGATCACCC GCCGCCCGGT GCCCGCCGCC   180

GCCCGCGCCA CCGGC ATG GCG CTC CGG GGC TTC TGC AGC GCC GAT GGC TCC    231
                 Met Ala Leu Arg Gly Phe Cys Ser Ala Asp Gly Ser
                  1               5                  10

GAC CCG CTC TGG GAC TGG AAT GTC ACG TGG AAT ACC AGC AAC CCC GAC     279
Asp Pro Leu Trp Asp Trp Asn Val Thr Trp Asn Thr Ser Asn Pro Asp
         15                  20                  25

TTC ACC AAG TGC TTT CAG AAC ACG GTC CTC GTG TGG GTG CCT TGT TTT     327
Phe Thr Lys Cys Phe Gln Asn Thr Val Leu Val Trp Val Pro Cys Phe
 30                  35                  40

TAC CTC TGG GCC TGT TTC CCC TTC TAC TTC CTC TAT CTC TCC CGA CAT     375
Tyr Leu Trp Ala Cys Phe Pro Phe Tyr Phe Leu Tyr Leu Ser Arg His
 45                  50                  55                  60

GAC CGA GGC TAC ATT CAG ATG ACA CCT CTC AAC AAA ACC AAA ACT GCC     423
Asp Arg Gly Tyr Ile Gln Met Thr Pro Leu Asn Lys Thr Lys Thr Ala
             65                  70                  75

TTG GGA TTT TTG CTG TGG ATC GTC TGC TGG GCA GAC CTC TTC TAC TCT     471
Leu Gly Phe Leu Leu Trp Ile Val Cys Trp Ala Asp Leu Phe Tyr Ser
             80                  85                  90

TTC TGG GAA AGA AGT CGG GGC ATA TTC CTG GCC CCA GTG TTT CTG GTC     519
Phe Trp Glu Arg Ser Arg Gly Ile Phe Leu Ala Pro Val Phe Leu Val
         95                 100                 105

AGC CCA ACT CTC TTG GGC ATC ACC ACG CTG CTT GCT ACC TTT TTA ATT     567
Ser Pro Thr Leu Leu Gly Ile Thr Thr Leu Leu Ala Thr Phe Leu Ile
    110                 115                 120

CAG CTG GAG AGG AGG AAG GGA GTT CAG TCT TCA GGG ATC ATG CTC ACT     615
Gln Leu Glu Arg Arg Lys Gly Val Gln Ser Ser Gly Ile Met Leu Thr
125                 130                 135                 140

TTC TGG CTG GTA GCC CTA GTG TGT GCC CTA GCC ATC CTG AGA TCC AAA     663
Phe Trp Leu Val Ala Leu Val Cys Ala Leu Ala Ile Leu Arg Ser Lys
                145                 150                 155

ATT ATG ACA GCC TTA AAA GAG GAT GCC CAG GTG GAC CTG TTT CGT GAC     711
Ile Met Thr Ala Leu Lys Glu Asp Ala Gln Val Asp Leu Phe Arg Asp
            160                 165                 170

ATC ACT TTC TAC GTC TAC TTT TCC CTC TTA CTC ATT CAG CTC GTC TTG     759
Ile Thr Phe Tyr Val Tyr Phe Ser Leu Leu Leu Ile Gln Leu Val Leu
        175                 180                 185

TCC TGT TTC TCA GAT CGC TCA CCC CTG TTC TCG GAA ACC ATC CAC GAC     807
Ser Cys Phe Ser Asp Arg Ser Pro Leu Phe Ser Glu Thr Ile His Asp
    190                 195                 200

CCT AAT CCC TGC CCA GAG TCC AGC GCT TCC TTC CTG TCG AGG ATC ACC     855
Pro Asn Pro Cys Pro Glu Ser Ser Ala Ser Phe Leu Ser Arg Ile Thr
205                 210                 215                 220

TTC TGG TGG ATC ACA GGG TTG ATT GTC CGG GGC TAC CGC CAG CCC CTG     903
Phe Trp Trp Ile Thr Gly Leu Ile Val Arg Gly Tyr Arg Gln Pro Leu
                225                 230                 235

GAG GGC AGT GAC CTC TGG TCC TTA AAC AAG GAG GAC ACG TCG GAA CAA     951
Glu Gly Ser Asp Leu Trp Ser Leu Asn Lys Glu Asp Thr Ser Glu Gln
```

-continued

```
                240                      245                      250
GTC GTG CCT GTT TTG GTA AAG AAC TGG AAG AAG GAA TGC GCC AAG ACT       999
Val Val Pro Val Leu Val Lys Asn Trp Lys Lys Glu Cys Ala Lys Thr
        255                     260                     265

AGG AAG CAG CCG GTG AAG GTT GTG TAC TCC TCC AAG GAT CCT GCC CAG      1047
Arg Lys Gln Pro Val Lys Val Val Tyr Ser Ser Lys Asp Pro Ala Gln
        270                     275                 280

CCG AAA GAG AGT TCC AAG GTG GAT GCG AAT GAG GAG GTG GAG GCT TTG      1095
Pro Lys Glu Ser Ser Lys Val Asp Ala Asn Glu Glu Val Glu Ala Leu
285                     290                     295                 300

ATC GTC AAG TCC CCA CAG AAG GAG TGG AAC CCC TCT CTG TTT AAG GTG      1143
Ile Val Lys Ser Pro Gln Lys Glu Trp Asn Pro Ser Leu Phe Lys Val
                305                     310                     315

TTA TAC AAG ACC TTT GGG CCC TAC TTC CTC ATG AGC TTC TTC TTC AAG      1191
Leu Tyr Lys Thr Phe Gly Pro Tyr Phe Leu Met Ser Phe Phe Phe Lys
                320                     325                     330

GCC ATC CAC GAC CTG ATG ATG TTT TCC GGG CCG CAG ATC TTA AAG TTG      1239
Ala Ile His Asp Leu Met Met Phe Ser Gly Pro Gln Ile Leu Lys Leu
                335                     340                     345

CTC ATC AAG TTC GTG AAT GAC ACG AAG GCC CCA GAC TGG CAG GGC TAC      1287
Leu Ile Lys Phe Val Asn Asp Thr Lys Ala Pro Asp Trp Gln Gly Tyr
350                     355                     360

TTC TAC ACC GTG CTG CTG TTT GTC ACT GCC TGC CTG CAG ACC CTC GTG      1335
Phe Tyr Thr Val Leu Leu Phe Val Thr Ala Cys Leu Gln Thr Leu Val
365                     370                     375                 380

CTG CAC CAG TAC TTC CAC ATC TGC TTC GTC AGT GGC ATG AGG ATC AAG      1383
Leu His Gln Tyr Phe His Ile Cys Phe Val Ser Gly Met Arg Ile Lys
                        385                     390                 395

ACC GCT GTC ATT GGG GCT GTC TAT CGG AAG GCC CTG GTG ATC ACC AAT      1431
Thr Ala Val Ile Gly Ala Val Tyr Arg Lys Ala Leu Val Ile Thr Asn
                        400                     405                 410

TCA GCC AGA AAA TCC TCC ACG GTC GGG GAG ATT GTC AAC CTC ATG TCT      1479
Ser Ala Arg Lys Ser Ser Thr Val Gly Glu Ile Val Asn Leu Met Ser
                415                     420                     425

GTG GAC GCT CAG AGG TTC ATG GAC TTG GCC ACG TAC ATT AAC ATG ATC      1527
Val Asp Ala Gln Arg Phe Met Asp Leu Ala Thr Tyr Ile Asn Met Ile
430                     435                     440

TGG TCA GCC CCC TTG CAA GTC ATC CTT GCT CTC TAC CTC CTG TGG CTG      1575
Trp Ser Ala Pro Leu Gln Val Ile Leu Ala Leu Tyr Leu Leu Trp Leu
445                     450                     455                 460

AAT CTG GGC CCT TCC GTC CTG GCT GGA GTG GCG GTG ATG GTC CTC ATG      1623
Asn Leu Gly Pro Ser Val Leu Ala Gly Val Ala Val Met Val Leu Met
                        465                     470                 475

GTG CCC GTC AAT GCT GTG ATG GCG ATG AAG ACC AAG ACG TAT CAG GTG      1671
Val Pro Val Asn Ala Val Met Ala Met Lys Thr Lys Thr Tyr Gln Val
                480                     485                     490

GCC CAC ATG AAG AGC AAA GAC AAT CGG ATC AAG CTG ATG AAC GAA ATT      1719
Ala His Met Lys Ser Lys Asp Asn Arg Ile Lys Leu Met Asn Glu Ile
                        495                     500                 505

CTC AAT GGG ATC AAA GTG CTA AAG CTT TAT GCC TGG GAG CTG GCA TTC      1767
Leu Asn Gly Ile Lys Val Leu Lys Leu Tyr Ala Trp Glu Leu Ala Phe
                510                     515                     520

AAG GAC AAG GTG CTG GCC ATC AGG CAG GAG GAG CTG AAG GTG CTG AAG      1815
Lys Asp Lys Val Leu Ala Ile Arg Gln Glu Glu Leu Lys Val Leu Lys
525                     530                     535                 540

AAG TCT GCC TAC CTG TCA GCC GTG GGC ACC TTC ACC TGG GTC TGC ACG      1863
Lys Ser Ala Tyr Leu Ser Ala Val Gly Thr Phe Thr Trp Val Cys Thr
                        545                     550                 555

CCC TTT CTG GTG GCC TTG TGC ACA TTT GCC GTC TAC GTG ACC ATT GAC      1911
Pro Phe Leu Val Ala Leu Cys Thr Phe Ala Val Tyr Val Thr Ile Asp
```

-continued

```
                560                    565                    570
GAG AAC AAC ATC CTG GAT GCC CAG ACA GCC TTC GTG TCT TTG GCC TTG       1959
Glu Asn Asn Ile Leu Asp Ala Gln Thr Ala Phe Val Ser Leu Ala Leu
            575                    580                    585

TTC AAC ATC CTC CGG TTT CCC CTG AAC ATT CTC CCC ATG GTC ATC AGC       2007
Phe Asn Ile Leu Arg Phe Pro Leu Asn Ile Leu Pro Met Val Ile Ser
        590                    595                    600

AGC ATC GTG CAG GCG AGT GTC TCC CTC AAA CGC CTG AGG ATC TTT CTC       2055
Ser Ile Val Gln Ala Ser Val Ser Leu Lys Arg Leu Arg Ile Phe Leu
605                    610                    615                    620

TCC CAT GAG GAG CTG GAA CCT GAC AGC ATC GAG CGA CGG CCT GTC AAA       2103
Ser His Glu Glu Leu Glu Pro Asp Ser Ile Glu Arg Arg Pro Val Lys
                625                    630                    635

GAC GGC GGG GGC ACG AAC AGC ATC ACC GTG AGG AAT GCC ACA TTC ACC       2151
Asp Gly Gly Gly Thr Asn Ser Ile Thr Val Arg Asn Ala Thr Phe Thr
            640                    645                    650

TGG GCC AGG AGC GAC CCT CCC ACA CTG AAT GGC ATC ACC TTC TCC ATC       2199
Trp Ala Arg Ser Asp Pro Pro Thr Leu Asn Gly Ile Thr Phe Ser Ile
            655                    660                    665

CCC GAA GGT GCT TTG GTG GCC GTG GTG GGC CAG GTG GGC TGC GGA AAG       2247
Pro Glu Gly Ala Leu Val Ala Val Val Gly Gln Val Gly Cys Gly Lys
        670                    675                    680

TTG TCC CTG CTC TCA GCC CTC TTG GCT GAG ATG GAC AAA GTG GAG GGG       2295
Leu Ser Leu Leu Ser Ala Leu Leu Ala Glu Met Asp Lys Val Glu Gly
685                    690                    695                    700

CAC GTG GCT ATC AAG GGC TCC GTG GCC TAT GTG CCA CAG CAG GCC TGG       2343
His Val Ala Ile Lys Gly Ser Val Ala Tyr Val Pro Gln Gln Ala Trp
                705                    710                    715

ATT CAG AAT GAT TCT CTC CGA GAA AAC ATC CTT TTT GGA TGT CAG CTG       2391
Ile Gln Asn Asp Ser Leu Arg Glu Asn Ile Leu Phe Gly Cys Gln Leu
            720                    725                    730

GAG GAA CCA TAT TAC AGG TCC GTG ATA CAG GCC TGT GCC CTC CTC CCA       2439
Glu Glu Pro Tyr Tyr Arg Ser Val Ile Gln Ala Cys Ala Leu Leu Pro
            735                    740                    745

GAC CTG GAA ATC CTG CCC AGT GGG GAT CGG ACA GAG ATT GGC GAG AAG       2487
Asp Leu Glu Ile Leu Pro Ser Gly Asp Arg Thr Glu Ile Gly Glu Lys
        750                    755                    760

GGC GTG AAC CTG TCT GGG GGA CAG AAG CAG CGC GTG AGC CTG GCC CGG       2535
Gly Val Asn Leu Ser Gly Gly Gln Lys Gln Arg Val Ser Leu Ala Arg
765                    770                    775                    780

GCC GTG TAC TCC AAC GCT GAC ATT TAC CTC TTC GAT GAT CCC CTC TCA       2583
Ala Val Tyr Ser Asn Ala Asp Ile Tyr Leu Phe Asp Asp Pro Leu Ser
                785                    790                    795

GCA GTG GAT GCC CAT GTG GGA AAA CAC ATC TTT GAA AAT GTG ATT GGC       2631
Ala Val Asp Ala His Val Gly Lys His Ile Phe Glu Asn Val Ile Gly
            800                    805                    810

CCC AAG GGG ATG CTG AAG AAC AAG ACG CGG ATC TTG GTC ACG CAC AGC       2679
Pro Lys Gly Met Leu Lys Asn Lys Thr Arg Ile Leu Val Thr His Ser
        815                    820                    825

ATG AGC TAC TTG CCG CAG GTG GAC GTC ATC ATC GTC ATG AGT GGC GGC       2727
Met Ser Tyr Leu Pro Gln Val Asp Val Ile Ile Val Met Ser Gly Gly
    830                    835                    840

AAG ATC TCT GAG ATG GGC TCC TAC CAG GAG CTG CTG GCT CGA GAC GGC       2775
Lys Ile Ser Glu Met Gly Ser Tyr Gln Glu Leu Leu Ala Arg Asp Gly
845                    850                    855                    860

GCC TTC GCT GAG TTC CTG CGT ACC TAT GCC AGC ACA GAG CAG GAG CAG       2823
Ala Phe Ala Glu Phe Leu Arg Thr Tyr Ala Ser Thr Glu Gln Glu Gln
                865                    870                    875

GAT GCA GAG GAG AAC GGG GTC ACG GGC GTC AGC GGT CCA GGG AAG GAA       2871
Asp Ala Glu Glu Asn Gly Val Thr Gly Val Ser Gly Pro Gly Lys Glu
```

-continued

|  | 880 |  |  |  |  | 885 |  |  |  |  | 890 |  |  |  |  |  |
|---|---|---|---|---|---|---|---|---|---|---|---|---|---|---|---|---|
| GCA | AAG | CAA | ATG | GAG | AAT | GGC | ATG | CTG | GTG | ACG | GAC | AGT | GCA | GGG | AAG | 2919 |
| Ala | Lys | Gln | Met | Glu | Asn | Gly | Met | Leu | Val | Thr | Asp | Ser | Ala | Gly | Lys |  |
|  | 895 |  |  |  |  | 900 |  |  |  |  | 905 |  |  |  |  |  |
| CAA | CTG | CAG | AGA | CAG | CTC | AGC | AGC | TCC | TCC | TCC | TAT | AGT | GGG | GAC | ATC | 2967 |
| Gln | Leu | Gln | Arg | Gln | Leu | Ser | Ser | Ser | Ser | Ser | Tyr | Ser | Gly | Asp | Ile |  |
|  | 910 |  |  |  |  | 915 |  |  |  |  | 920 |  |  |  |  |  |
| AGC | AGG | CAC | CAC | AAC | AGC | ACC | GCA | GAA | CTG | CAG | AAA | GCT | GAG | GCC | AAG | 3015 |
| Ser | Arg | His | His | Asn | Ser | Thr | Ala | Glu | Leu | Gln | Lys | Ala | Glu | Ala | Lys |  |
| 925 |  |  |  |  | 930 |  |  |  |  | 935 |  |  |  |  | 940 |  |
| AAG | GAG | GAG | ACC | TGG | AAG | CTG | ATG | GAG | GCT | GAC | AAG | GCG | CAG | ACA | GGG | 3063 |
| Lys | Glu | Glu | Thr | Trp | Lys | Leu | Met | Glu | Ala | Asp | Lys | Ala | Gln | Thr | Gly |  |
|  |  |  |  | 945 |  |  |  |  | 950 |  |  |  |  | 955 |  |  |
| CAG | GTC | AAG | CTT | TCC | GTG | TAC | TGG | GAC | TAC | ATG | AAG | GCC | ATC | GGA | CTC | 3111 |
| Gln | Val | Lys | Leu | Ser | Val | Tyr | Trp | Asp | Tyr | Met | Lys | Ala | Ile | Gly | Leu |  |
|  |  | 960 |  |  |  |  | 965 |  |  |  |  | 970 |  |  |  |  |
| TTC | ATC | TCC | TTC | CTC | AGC | ATC | TTC | CTT | TTC | ATG | TGT | AAC | CAT | GTG | TCC | 3159 |
| Phe | Ile | Ser | Phe | Leu | Ser | Ile | Phe | Leu | Phe | Met | Cys | Asn | His | Val | Ser |  |
|  | 975 |  |  |  |  | 980 |  |  |  |  | 985 |  |  |  |  |  |
| GCG | CTG | GCT | TCC | AAC | TAT | TGG | CTC | AGC | CTC | TGG | ACT | GAT | GAC | CCC | ATC | 3207 |
| Ala | Leu | Ala | Ser | Asn | Tyr | Trp | Leu | Ser | Leu | Trp | Thr | Asp | Asp | Pro | Ile |  |
| 990 |  |  |  |  | 995 |  |  |  |  | 1000 |  |  |  |  |  |  |
| GTC | AAC | GGG | ACT | CAG | GAG | CAC | ACG | AAA | GTC | CGG | CTG | AGC | GTC | TAT | GGA | 3255 |
| Val | Asn | Gly | Thr | Gln | Glu | His | Thr | Lys | Val | Arg | Leu | Ser | Val | Tyr | Gly |  |
| 1005 |  |  |  |  | 1010 |  |  |  |  | 1015 |  |  |  |  | 1020 |  |
| GCC | CTG | GGC | ATT | TCA | CAA | GGG | ATC | GCC | GTG | TTT | GGC | TAC | TCC | ATG | GCC | 3303 |
| Ala | Leu | Gly | Ile | Ser | Gln | Gly | Ile | Ala | Val | Phe | Gly | Tyr | Ser | Met | Ala |  |
|  |  |  |  | 1025 |  |  |  |  | 1030 |  |  |  |  | 1035 |  |  |
| GTG | TCC | ATC | GGG | GGG | ATC | TTG | GCT | TCC | CGC | TGT | CTG | CAC | GTG | GAC | CTG | 3351 |
| Val | Ser | Ile | Gly | Gly | Ile | Leu | Ala | Ser | Arg | Cys | Leu | His | Val | Asp | Leu |  |
|  |  |  | 1040 |  |  |  |  | 1045 |  |  |  |  | 1050 |  |  |  |
| CTG | CAC | AGC | ATC | CTG | CGG | TCA | CCC | ATG | AGC | TTC | TTT | GAG | CGG | ACC | CCC | 3399 |
| Leu | His | Ser | Ile | Leu | Arg | Ser | Pro | Met | Ser | Phe | Phe | Glu | Arg | Thr | Pro |  |
|  |  | 1055 |  |  |  |  | 1060 |  |  |  |  | 1065 |  |  |  |  |
| AGT | GGG | AAC | CTG | GTG | AAC | CGC | TTC | TCC | AAG | GAG | CTG | GAC | ACA | GTG | GAC | 3447 |
| Ser | Gly | Asn | Leu | Val | Asn | Arg | Phe | Ser | Lys | Glu | Leu | Asp | Thr | Val | Asp |  |
|  | 1070 |  |  |  |  | 1075 |  |  |  |  | 1080 |  |  |  |  |  |
| TCC | ATG | ATC | CCG | GAG | GTC | ATC | AAG | ATG | TTC | ATG | GGC | TCC | CTG | TTC | AAC | 3495 |
| Ser | Met | Ile | Pro | Glu | Val | Ile | Lys | Met | Phe | Met | Gly | Ser | Leu | Phe | Asn |  |
| 1085 |  |  |  |  | 1090 |  |  |  |  | 1095 |  |  |  |  | 1100 |  |
| GTC | ATT | GGT | GCC | TGC | ATC | GTT | ATC | CTG | CTG | GCC | ACG | CCC | ATC | GCC | GCC | 3543 |
| Val | Ile | Gly | Ala | Cys | Ile | Val | Ile | Leu | Leu | Ala | Thr | Pro | Ile | Ala | Ala |  |
|  |  |  |  | 1105 |  |  |  |  | 1110 |  |  |  |  | 1115 |  |  |
| ATC | ATC | ATC | CCG | CCC | CTT | GGC | CTC | ATC | TAC | TTC | TTC | GTC | CAG | AGG | TTC | 3591 |
| Ile | Ile | Ile | Pro | Pro | Leu | Gly | Leu | Ile | Tyr | Phe | Phe | Val | Gln | Arg | Phe |  |
|  |  |  | 1120 |  |  |  |  | 1125 |  |  |  |  | 1130 |  |  |  |
| TAC | GTG | GCT | TCC | TCC | CGG | CAG | CTG | AAG | CGC | CTC | GAG | TCG | GTC | AGC | CGC | 3639 |
| Tyr | Val | Ala | Ser | Ser | Arg | Gln | Leu | Lys | Arg | Leu | Glu | Ser | Val | Ser | Arg |  |
|  |  | 1135 |  |  |  |  | 1140 |  |  |  |  | 1145 |  |  |  |  |
| TCC | CCG | GTC | TAT | TCC | CAT | TTC | AAC | GAG | ACC | TTG | CTG | GGG | GTC | AGC | GTC | 3687 |
| Ser | Pro | Val | Tyr | Ser | His | Phe | Asn | Glu | Thr | Leu | Leu | Gly | Val | Ser | Val |  |
|  | 1150 |  |  |  |  | 1155 |  |  |  |  | 1160 |  |  |  |  |  |
| ATT | CGA | GCC | TTC | GAG | GAG | CAG | GAG | CGC | TTC | ATC | CAC | CAG | AGT | GAC | CTG | 3735 |
| Ile | Arg | Ala | Phe | Glu | Glu | Gln | Glu | Arg | Phe | Ile | His | Gln | Ser | Asp | Leu |  |
| 1165 |  |  |  |  | 1170 |  |  |  |  | 1175 |  |  |  |  | 1180 |  |
| AAG | GTG | GAC | GAG | AAC | CAG | AAG | GCC | TAT | TAC | CCC | AGC | ATC | GTG | GCC | AAC | 3783 |
| Lys | Val | Asp | Glu | Asn | Gln | Lys | Ala | Tyr | Tyr | Pro | Ser | Ile | Val | Ala | Asn |  |
|  |  |  |  | 1185 |  |  |  |  | 1190 |  |  |  |  | 1195 |  |  |
| AGG | TGG | CTG | GCC | GTG | CGG | CTG | GAG | TGT | GTG | GGC | AAC | TGC | ATC | GTT | CTG | 3831 |
| Arg | Trp | Leu | Ala | Val | Arg | Leu | Glu | Cys | Val | Gly | Asn | Cys | Ile | Val | Leu |  |

```
                1200                    1205                    1210
TTT GCT GCC CTG TTT GCG GTG ATC TCC AGG CAC AGC CTC AGT GCT GGC    3879
Phe Ala Ala Leu Phe Ala Val Ile Ser Arg His Ser Leu Ser Ala Gly
        1215                    1220                    1225

TTG GTG GGC CTC TCA GTG TCT TAC TCA TTG CAG GTC ACC ACG TAC TTG    3927
Leu Val Gly Leu Ser Val Ser Tyr Ser Leu Gln Val Thr Thr Tyr Leu
    1230                    1235                    1240

AAC TGG CTG GTT CGG ATG TCA TCT GAA ATG GAA ACC AAC ATC GTG GCC    3975
Asn Trp Leu Val Arg Met Ser Ser Glu Met Glu Thr Asn Ile Val Ala
1245                    1250                    1255                    1260

GTG GAG AGG CTC AAG GAG TAT TCA GAG ACT GAG AAG GAG GCG CCC TGG    4023
Val Glu Arg Leu Lys Glu Tyr Ser Glu Thr Glu Lys Glu Ala Pro Trp
            1265                    1270                    1275

CAA ATC CAG GAG ACA CGT CCG CCC AGC AGC TGG CCC CAG GTG GGC CGA    4071
Gln Ile Gln Glu Thr Arg Pro Pro Ser Ser Trp Pro Gln Val Gly Arg
        1280                    1285                    1290

GTG GAA TTC CGG AAC TAC TGC CTG CGC TAC CGA GAG GAC CTG GAC TTC    4119
Val Glu Phe Arg Asn Tyr Cys Leu Arg Tyr Arg Glu Asp Leu Asp Phe
    1295                    1300                    1305

GTT CTC AGG CAC ATC AAT GTC ACG ATC AAT GGG GGA GAA AAG GTC GGC    4167
Val Leu Arg His Ile Asn Val Thr Ile Asn Gly Gly Glu Lys Val Gly
    1310                    1315                    1320

ATC GTG GGG CGG ACG GGA GCT GGG AAG TCG TCC CTG ACC CTG GGC TTA    4215
Ile Val Gly Arg Thr Gly Ala Gly Lys Ser Ser Leu Thr Leu Gly Leu
1325                    1330                    1335                    1340

TTT CGG ATC AAC GAG TCT GCC GAA GGA GAG ATC ATC ATC GAT GGC ATC    4263
Phe Arg Ile Asn Glu Ser Ala Glu Gly Glu Ile Ile Ile Asp Gly Ile
            1345                    1350                    1355

AAC ATC GCC AAG ATC GGC CTG CAC GAC CTC CGC TTC AAG ATC ACC ATC    4311
Asn Ile Ala Lys Ile Gly Leu His Asp Leu Arg Phe Lys Ile Thr Ile
        1360                    1365                    1370

ATC CCC CAG GAC CCT GTT TTG TTT TCG GGT TCC CTC CGA ATG AAC CTG    4359
Ile Pro Gln Asp Pro Val Leu Phe Ser Gly Ser Leu Arg Met Asn Leu
    1375                    1380                    1385

GAC CCA TTC AGC CAG TAC TCG GAT GAA GAA GTC TGG ACG TCC CTG GAG    4407
Asp Pro Phe Ser Gln Tyr Ser Asp Glu Glu Val Trp Thr Ser Leu Glu
    1390                    1395                    1400

CTG GCC CAC CTG AAG GAC TTC GTG TCA GCC CTT CCT GAC AAG CTA GAC    4455
Leu Ala His Leu Lys Asp Phe Val Ser Ala Leu Pro Asp Lys Leu Asp
1405                    1410                    1415                    1420

CAT GAA TGT GCA GAA GGC GGG GAG AAC CTC AGT GTC GGG CAG CGC CAG    4503
His Glu Cys Ala Glu Gly Gly Glu Asn Leu Ser Val Gly Gln Arg Gln
            1425                    1430                    1435

CTT GTG TGC CTA GCC CGG GCC CTG CTG AGG AAG ACG AAG ATC CTT GTG    4551
Leu Val Cys Leu Ala Arg Ala Leu Leu Arg Lys Thr Lys Ile Leu Val
        1440                    1445                    1450

TTG GAT GAG GCC ACG GCA GCC GTG GAC CTG GAA ACG GAC GAC CTC ATC    4599
Leu Asp Glu Ala Thr Ala Ala Val Asp Leu Glu Thr Asp Asp Leu Ile
    1455                    1460                    1465

CAG TCC ACC ATC CGG ACA CAG TTC GAG GAC TGC ACC GTC CTC ACC ATC    4647
Gln Ser Thr Ile Arg Thr Gln Phe Glu Asp Cys Thr Val Leu Thr Ile
    1470                    1475                    1480

GCC CAC CGG CTC AAC ACC ATC ATG GAC TAC ACA AGG GTG ATC GTC TTG    4695
Ala His Arg Leu Asn Thr Ile Met Asp Tyr Thr Arg Val Ile Val Leu
1485                    1490                    1495                    1500

GAC AAA GGA GAA ATC CAG GAG TAC GGC GCC CCA TCG GAC CTC CTG CAG    4743
Asp Lys Gly Glu Ile Gln Glu Tyr Gly Ala Pro Ser Asp Leu Leu Gln
            1505                    1510                    1515

CAG AGA GGT CTT TTC TAC AGC ATG GCC AAA GAC GCC GGC TTG GTG        4788
Gln Arg Gly Leu Phe Tyr Ser Met Ala Lys Asp Ala Gly Leu Val
```

-continued

```
             1520           1525            1530
TGAGCCCCAG AGCTGGCATA TCTGGTCAGA ACTGCAGGGC CTATATGCCA GCGCCCCAGG      4848

GAGGAGTCAG TACCCCTGGT AAACCAAGCC TCCCACACTG AAACCAAAAC ATAAAAACCA      4908

AACCCAGACA ACCAAAACAT ATTCAAAGCA GCAGCCACCG CCATCCGGTC CCCTGCCTGG      4968

AACTGGCTGT GAAGACCCAG GAGAGACAGA GATGCGAACC ACC                       5011
```

(2) INFORMATION FOR SEQ ID NO:2:

(i) SEQUENCE CHARACTERISTICS:
        (A) LENGTH: 1531 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Leu Arg Gly Phe Cys Ser Ala Asp Gly Ser Asp Pro Leu Trp
 1               5                  10                  15

Asp Trp Asn Val Thr Trp Asn Thr Ser Asn Pro Asp Phe Thr Lys Cys
            20                  25                  30

Phe Gln Asn Thr Val Leu Val Trp Val Pro Cys Phe Tyr Leu Trp Ala
        35                  40                  45

Cys Phe Pro Phe Tyr Phe Leu Tyr Leu Ser Arg His Asp Arg Gly Tyr
50                  55                  60

Ile Gln Met Thr Pro Leu Asn Lys Thr Lys Thr Ala Leu Gly Phe Leu
65                  70                  75                  80

Leu Trp Ile Val Cys Trp Ala Asp Leu Phe Tyr Ser Phe Trp Glu Arg
                85                  90                  95

Ser Arg Gly Ile Phe Leu Ala Pro Val Phe Leu Val Ser Pro Thr Leu
            100                 105                 110

Leu Gly Ile Thr Thr Leu Leu Ala Thr Phe Leu Ile Gln Leu Glu Arg
        115                 120                 125

Arg Lys Gly Val Gln Ser Ser Gly Ile Met Leu Thr Phe Trp Leu Val
    130                 135                 140

Ala Leu Val Cys Ala Leu Ala Ile Leu Arg Ser Lys Ile Met Thr Ala
145                 150                 155                 160

Leu Lys Glu Asp Ala Gln Val Asp Leu Phe Arg Asp Ile Thr Phe Tyr
                165                 170                 175

Val Tyr Phe Ser Leu Leu Leu Ile Gln Leu Val Leu Ser Cys Phe Ser
            180                 185                 190

Asp Arg Ser Pro Leu Phe Ser Glu Thr Ile His Asp Pro Asn Pro Cys
        195                 200                 205

Pro Glu Ser Ser Ala Ser Phe Leu Ser Arg Ile Thr Phe Trp Trp Ile
    210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
            260                 265                 270

Val Lys Val Val Tyr Ser Ser Lys Asp Pro Ala Gln Pro Lys Glu Ser
        275                 280                 285

Ser Lys Val Asp Ala Asn Glu Glu Val Glu Ala Leu Ile Val Lys Ser
    290                 295                 300

Pro Gln Lys Glu Trp Asn Pro Ser Leu Phe Lys Val Leu Tyr Lys Thr
```

-continued

```
             305                 310                 315                 320
Phe Gly Pro Tyr Phe Leu Met Ser Phe Phe Lys Ala Ile His Asp
                 325                 330                 335
Leu Met Met Phe Ser Gly Pro Gln Ile Leu Lys Leu Leu Ile Lys Phe
                 340                 345                 350
Val Asn Asp Thr Lys Ala Pro Asp Trp Gln Gly Tyr Phe Tyr Thr Val
                 355                 360                 365
Leu Leu Phe Val Thr Ala Cys Leu Gln Thr Leu Val Leu His Gln Tyr
                 370                 375                 380
Phe His Ile Cys Phe Val Ser Gly Met Arg Ile Lys Thr Ala Val Ile
385                 390                 395                 400
Gly Ala Val Tyr Arg Lys Ala Leu Val Ile Thr Asn Ser Ala Arg Lys
                 405                 410                 415
Ser Ser Thr Val Gly Glu Ile Val Asn Leu Met Ser Val Asp Ala Gln
                 420                 425                 430
Arg Phe Met Asp Leu Ala Thr Tyr Ile Asn Met Ile Trp Ser Ala Pro
                 435                 440                 445
Leu Gln Val Ile Leu Ala Leu Tyr Leu Leu Trp Leu Asn Leu Gly Pro
                 450                 455                 460
Ser Val Leu Ala Gly Val Ala Val Met Val Leu Met Val Pro Val Asn
465                 470                 475                 480
Ala Val Met Ala Met Lys Thr Lys Thr Tyr Gln Val Ala His Met Lys
                 485                 490                 495
Ser Lys Asp Asn Arg Ile Lys Leu Met Asn Glu Ile Leu Asn Gly Ile
                 500                 505                 510
Lys Val Leu Lys Leu Tyr Ala Trp Glu Leu Ala Phe Lys Asp Lys Val
                 515                 520                 525
Leu Ala Ile Arg Gln Glu Glu Leu Lys Val Leu Lys Lys Ser Ala Tyr
                 530                 535                 540
Leu Ser Ala Val Gly Thr Phe Thr Trp Val Cys Thr Pro Phe Leu Val
545                 550                 555                 560
Ala Leu Cys Thr Phe Ala Val Tyr Val Thr Ile Asp Glu Asn Asn Ile
                 565                 570                 575
Leu Asp Ala Gln Thr Ala Phe Val Ser Leu Ala Leu Phe Asn Ile Leu
                 580                 585                 590
Arg Phe Pro Leu Asn Ile Leu Pro Met Val Ile Ser Ser Ile Val Gln
                 595                 600                 605
Ala Ser Val Ser Leu Lys Arg Leu Arg Ile Phe Leu Ser His Glu Glu
                 610                 615                 620
Leu Glu Pro Asp Ser Ile Glu Arg Arg Pro Val Lys Asp Gly Gly Gly
625                 630                 635                 640
Thr Asn Ser Ile Thr Val Arg Asn Ala Thr Phe Thr Trp Ala Arg Ser
                 645                 650                 655
Asp Pro Pro Thr Leu Asn Gly Ile Thr Phe Ser Ile Pro Glu Gly Ala
                 660                 665                 670
Leu Val Ala Val Val Gly Gln Val Gly Cys Gly Lys Leu Ser Leu Leu
                 675                 680                 685
Ser Ala Leu Leu Ala Glu Met Asp Lys Val Glu Gly His Val Ala Ile
                 690                 695                 700
Lys Gly Ser Val Ala Tyr Val Pro Gln Gln Ala Trp Ile Gln Asn Asp
705                 710                 715                 720
Ser Leu Arg Glu Asn Ile Leu Phe Gly Cys Gln Leu Glu Glu Pro Tyr
                 725                 730                 735
```

-continued

```
Tyr Arg Ser Val Ile Gln Ala Cys Ala Leu Leu Pro Asp Leu Glu Ile
            740                 745                 750

Leu Pro Ser Gly Asp Arg Thr Glu Ile Gly Glu Lys Gly Val Asn Leu
            755                 760                 765

Ser Gly Gly Gln Lys Gln Arg Val Ser Leu Ala Arg Ala Val Tyr Ser
            770                 775                 780

Asn Ala Asp Ile Tyr Leu Phe Asp Asp Pro Leu Ser Ala Val Asp Ala
785                 790                 795                 800

His Val Gly Lys His Ile Phe Glu Asn Val Ile Gly Pro Lys Gly Met
                    805                 810                 815

Leu Lys Asn Lys Thr Arg Ile Leu Val Thr His Ser Met Ser Tyr Leu
                    820                 825                 830

Pro Gln Val Asp Val Ile Val Met Ser Gly Lys Ile Ser Glu
                    835                 840                 845

Met Gly Ser Tyr Gln Glu Leu Leu Ala Arg Asp Gly Ala Phe Ala Glu
850                 855                 860

Phe Leu Arg Thr Tyr Ala Ser Thr Glu Gln Glu Gln Asp Ala Glu Glu
865                 870                 875                 880

Asn Gly Val Thr Gly Val Ser Gly Pro Gly Lys Glu Ala Lys Gln Met
                    885                 890                 895

Glu Asn Gly Met Leu Val Thr Asp Ser Ala Gly Lys Gln Leu Gln Arg
                    900                 905                 910

Gln Leu Ser Ser Ser Ser Tyr Ser Gly Asp Ile Ser Arg His His
                    915                 920                 925

Asn Ser Thr Ala Glu Leu Gln Lys Ala Glu Ala Lys Lys Glu Glu Thr
930                 935                 940

Trp Lys Leu Met Glu Ala Asp Lys Ala Gln Thr Gly Gln Val Lys Leu
945                 950                 955                 960

Ser Val Tyr Trp Asp Tyr Met Lys Ala Ile Gly Leu Phe Ile Ser Phe
                    965                 970                 975

Leu Ser Ile Phe Leu Phe Met Cys Asn His Val Ser Ala Leu Ala Ser
                    980                 985                 990

Asn Tyr Trp Leu Ser Leu Trp Thr Asp Asp Pro Ile Val Asn Gly Thr
                    995                1000                1005

Gln Glu His Thr Lys Val Arg Leu Ser Val Tyr Gly Ala Leu Gly Ile
           1010                1015                1020

Ser Gln Gly Ile Ala Val Phe Gly Tyr Ser Met Ala Val Ser Ile Gly
1025                1030                1035                1040

Gly Ile Leu Ala Ser Arg Cys Leu His Val Asp Leu Leu His Ser Ile
                    1045                1050                1055

Leu Arg Ser Pro Met Ser Phe Phe Glu Arg Thr Pro Ser Gly Asn Leu
                    1060                1065                1070

Val Asn Arg Phe Ser Lys Glu Leu Asp Thr Val Asp Ser Met Ile Pro
                    1075                1080                1085

Glu Val Ile Lys Met Phe Met Gly Ser Leu Phe Asn Val Ile Gly Ala
           1090                1095                1100

Cys Ile Val Ile Leu Leu Ala Thr Pro Ile Ala Ala Ile Ile Ile Pro
1105                1110                1115                1120

Pro Leu Gly Leu Ile Tyr Phe Phe Val Gln Arg Phe Tyr Val Ala Ser
                    1125                1130                1135

Ser Arg Gln Leu Lys Arg Leu Glu Ser Val Ser Arg Ser Pro Val Tyr
                    1140                1145                1150

Ser His Phe Asn Glu Thr Leu Leu Gly Val Ser Val Ile Arg Ala Phe
                    1155                1160                1165
```

Glu Glu Gln Glu Arg Phe Ile His Gln Ser Asp Leu Lys Val Asp Glu
    1170                1175                1180

Asn Gln Lys Ala Tyr Tyr Pro Ser Ile Val Ala Asn Arg Trp Leu Ala
1185                1190                1195                1200

Val Arg Leu Glu Cys Val Gly Asn Cys Ile Val Leu Phe Ala Ala Leu
            1205                1210                1215

Phe Ala Val Ile Ser Arg His Ser Leu Ser Ala Gly Leu Val Gly Leu
        1220                1225                1230

Ser Val Ser Tyr Ser Leu Gln Val Thr Thr Tyr Leu Asn Trp Leu Val
    1235                1240                1245

Arg Met Ser Ser Glu Met Glu Thr Asn Ile Val Ala Val Glu Arg Leu
1250                1255                1260

Lys Glu Tyr Ser Glu Thr Glu Lys Glu Ala Pro Trp Gln Ile Gln Glu
1265                1270                1275                1280

Thr Arg Pro Pro Ser Ser Trp Pro Gln Val Gly Arg Val Glu Phe Arg
            1285                1290                1295

Asn Tyr Cys Leu Arg Tyr Arg Glu Asp Leu Asp Phe Val Leu Arg His
        1300                1305                1310

Ile Asn Val Thr Ile Asn Gly Gly Glu Lys Val Gly Ile Val Gly Arg
        1315                1320                1325

Thr Gly Ala Gly Lys Ser Ser Leu Thr Leu Gly Leu Phe Arg Ile Asn
    1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
            1365                1370                1375

Pro Val Leu Phe Ser Gly Ser Leu Arg Met Asn Leu Asp Pro Phe Ser
        1380                1385                1390

Gln Tyr Ser Asp Glu Glu Val Trp Thr Ser Leu Glu Leu Ala His Leu
    1395                1400                1405

Lys Asp Phe Val Ser Ala Leu Pro Asp Lys Leu Asp His Glu Cys Ala
1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
            1445                1450                1455

Thr Ala Ala Val Asp Leu Glu Thr Asp Asp Leu Ile Gln Ser Thr Ile
        1460                1465                1470

Arg Thr Gln Phe Glu Asp Cys Thr Val Leu Thr Ile Ala His Arg Leu
    1475                1480                1485

Asn Thr Ile Met Asp Tyr Thr Arg Val Ile Val Leu Asp Lys Gly Glu
1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
            1525                1530

(2) INFORMATION FOR SEQ ID NO:3:

(i) SEQUENCE CHARACTERISTICS:
        (A) LENGTH: 5011 base pairs
        (B) TYPE: nucleic acid
        (C) STRANDEDNESS: double
        (D) TOPOLOGY: linear (ii) MOLECULE TYPE: cDNA (ix) FEATURE:
   (A) NAME/KEY: CDS
   (B) LOCATION: 196..4788

(xi) SEQUENCE DESCRIPTION: SEQ ID NO:3:

```
CAGGCGGCGT TGCGGCCCCG GCCCCGGCTC CCTGCGCCGC CGCCGCCGCC GCCGCCGCCG     60

CCGCCGCCGC CGCCGCCAGC GCTAGCGCCA GCAGCCGGGC CCGATCACCC GCCGCCCGGT    120

GCCCGCCGCC GCCCGCGCCA GCAACCGGGC CCGATCACCC GCCGCCCGGT GCCCGCCGCC    180

GCCCGCGCCA CCGGC ATG GCG CTC CGG GGC TTC TGC AGC GCC GAT GGC TCC     231
                Met Ala Leu Arg Gly Phe Cys Ser Ala Asp Gly Ser
                 1               5                  10

GAC CCG CTC TGG GAC TGG AAT GTC ACG TGG AAT ACC AGC AAC CCC GAC      279
Asp Pro Leu Trp Asp Trp Asn Val Thr Trp Asn Thr Ser Asn Pro Asp
            15                  20                  25

TTC ACC AAG TGC TTT CAG AAC ACG GTC CTC GTG TGG GTG CCT TGT TTT      327
Phe Thr Lys Cys Phe Gln Asn Thr Val Leu Val Trp Val Pro Cys Phe
        30                  35                  40

TAC CTC TGG GCC TGT TTC CCC TTC TAC TTC CTC TAT CTC TCC CGA CAT      375
Tyr Leu Trp Ala Cys Phe Pro Phe Tyr Phe Leu Tyr Leu Ser Arg His
    45                  50                  55                  60

GAC CGA GGC TAC ATT CAG ATG ACA CCT CTC AAC AAA ACC AAA ACT GCC      423
Asp Arg Gly Tyr Ile Gln Met Thr Pro Leu Asn Lys Thr Lys Thr Ala
                65                  70                  75

TTG GGA TTT TTG CTG TGG ATC GTC TGC TGG GCA GAC CTC TTC TAC TCT      471
Leu Gly Phe Leu Leu Trp Ile Val Cys Trp Ala Asp Leu Phe Tyr Ser
            80                  85                  90

TTC TGG GAA AGA AGT CGG GGC ATA TTC CTG GCC CCA GTG TTT CTG GTC      519
Phe Trp Glu Arg Ser Arg Gly Ile Phe Leu Ala Pro Val Phe Leu Val
        95                  100                 105

AGC CCA ACT CTC TTG GGC ATC ACC ACG CTG CTT GCT ACC TTT TTA ATT      567
Ser Pro Thr Leu Leu Gly Ile Thr Thr Leu Leu Ala Thr Phe Leu Ile
    110                 115                 120

CAG CTG GAG AGG AGG AAG GGA GTT CAG TCT TCA GGG ATC ATG CTC ACT      615
Gln Leu Glu Arg Arg Lys Gly Val Gln Ser Ser Gly Ile Met Leu Thr
125                 130                 135                 140

TTC TGG CTG GTA GCC CTA GTG TGT GCC CTA GCC ATC CTG AGA TCC AAA      663
Phe Trp Leu Val Ala Leu Val Cys Ala Leu Ala Ile Leu Arg Ser Lys
                145                 150                 155

ATT ATG ACA GCC TTA AAA GAG GAT GCC CAG GTG GAC CTG TTT CGT GAC      711
Ile Met Thr Ala Leu Lys Glu Asp Ala Gln Val Asp Leu Phe Arg Asp
            160                 165                 170

ATC ACT TTC TAC GTC TAC TTT TCC CTC TTA CTC ATT CAG CTC GTC TTG      759
Ile Thr Phe Tyr Val Tyr Phe Ser Leu Leu Leu Ile Gln Leu Val Leu
        175                 180                 185

TCC TGT TTC TCA GAT CGC TCA CCC CTG TTC TCG GAA ACC ATC CAC GAC      807
Ser Cys Phe Ser Asp Arg Ser Pro Leu Phe Ser Glu Thr Ile His Asp
    190                 195                 200

CCT AAT CCC TGC CCA GAG TCC AGC GCT TCC TTC CTG TCG AGG ATC ACC      855
Pro Asn Pro Cys Pro Glu Ser Ser Ala Ser Phe Leu Ser Arg Ile Thr
205                 210                 215                 220

TTC TGG TGG ATC ACA GGG TTG ATT GTC CGG GGC TAC CGC CAG CCC CTG      903
Phe Trp Trp Ile Thr Gly Leu Ile Val Arg Gly Tyr Arg Gln Pro Leu
                225                 230                 235

GAG GGC AGT GAC CTC TGG TCC TTA AAC AAG GAG GAC ACG TCG GAA CAA      951
Glu Gly Ser Asp Leu Trp Ser Leu Asn Lys Glu Asp Thr Ser Glu Gln
            240                 245                 250

GTC GTG CCT GTT TTG GTA AAG AAC TGG AAG AAG GAA TGC GCC AAG ACT      999
Val Val Pro Val Leu Val Lys Asn Trp Lys Lys Glu Cys Ala Lys Thr
        255                 260                 265
```

```
AGG AAG CAG CCG GTG AAG GTT GTG TAC TCC TCC AAG GAT CCT GCC CAG    1047
Arg Lys Gln Pro Val Lys Val Val Tyr Ser Ser Lys Asp Pro Ala Gln
270                 275                 280

CCG AAA GAG AGT TCC AAG GTG GAT GCG AAT GAG GAG GTG GAG GCT TTG    1095
Pro Lys Glu Ser Ser Lys Val Asp Ala Asn Glu Glu Val Glu Ala Leu
285                 290                 295                 300

ATC GTC AAG TCC CCA CAG AAG GAG TGG AAC CCC TCT CTG TTT AAG GTG    1143
Ile Val Lys Ser Pro Gln Lys Glu Trp Asn Pro Ser Leu Phe Lys Val
                305                 310                 315

TTA TAC AAG ACC TTT GGG CCC TAC TTC CTC ATG AGC TTC TTC TTC AAG    1191
Leu Tyr Lys Thr Phe Gly Pro Tyr Phe Leu Met Ser Phe Phe Phe Lys
                320                 325                 330

GCC ATC CAC GAC CTG ATG ATG TTT TCC GGG CCG CAG ATC TTA AAG TTG    1239
Ala Ile His Asp Leu Met Met Phe Ser Gly Pro Gln Ile Leu Lys Leu
                335                 340                 345

CTC ATC AAG TTC GTG AAT GAC ACG AAG GCC CCA GAC TGG CAG GGC TAC    1287
Leu Ile Lys Phe Val Asn Asp Thr Lys Ala Pro Asp Trp Gln Gly Tyr
350                 355                 360

TTC TAC ACC GTG CTG CTG TTT GTC ACT GCC TGC CTG CAG ACC CTC GTG    1335
Phe Tyr Thr Val Leu Leu Phe Val Thr Ala Cys Leu Gln Thr Leu Val
365                 370                 375                 380

CTG CAC CAG TAC TTC CAC ATC TGC TTC GTC AGT GGC ATG AGG ATC AAG    1383
Leu His Gln Tyr Phe His Ile Cys Phe Val Ser Gly Met Arg Ile Lys
                385                 390                 395

ACC GCT GTC ATT GGG GCT GTC TAT CGG AAG GCC CTG GTG ATC ACC AAT    1431
Thr Ala Val Ile Gly Ala Val Tyr Arg Lys Ala Leu Val Ile Thr Asn
                400                 405                 410

TCA GCC AGA AAA TCC TCC ACG GTC GGG GAG ATT GTC AAC CTC ATG TCT    1479
Ser Ala Arg Lys Ser Ser Thr Val Gly Glu Ile Val Asn Leu Met Ser
            415                 420                 425

GTG GAC GCT CAG AGG TTC ATG GAC TTG GCC ACG TAC ATT AAC ATG ATC    1527
Val Asp Ala Gln Arg Phe Met Asp Leu Ala Thr Tyr Ile Asn Met Ile
430                 435                 440

TGG TCA GCC CCC CTG CAA GTC ATC CTT GCT CTC TAC CTC CTG TGG CTG    1575
Trp Ser Ala Pro Leu Gln Val Ile Leu Ala Leu Tyr Leu Leu Trp Leu
445                 450                 455                 460

AAT CTG GGC CCT TCC GTC CTG GCT GGA GTG GCG GTG ATG GTC CTC ATG    1623
Asn Leu Gly Pro Ser Val Leu Ala Gly Val Ala Val Met Val Leu Met
                465                 470                 475

GTG CCC GTC AAT GCT GTG ATG GCG ATG AAG ACC AAG ACG TAT CAG GTG    1671
Val Pro Val Asn Ala Val Met Ala Met Lys Thr Lys Thr Tyr Gln Val
            480                 485                 490

GCC CAC ATG AAG AGC AAA GAC AAT CGG ATC AAG CTG ATG AAC GAA ATT    1719
Ala His Met Lys Ser Lys Asp Asn Arg Ile Lys Leu Met Asn Glu Ile
                495                 500                 505

CTC AAT GGG ATC AAA GTG CTA AAG CTT TAT GCC TGG GAG CTG GCA TTC    1767
Leu Asn Gly Ile Lys Val Leu Lys Leu Tyr Ala Trp Glu Leu Ala Phe
510                 515                 520

AAG GAC AAG GTG CTG GCC ATC AGG CAG GAG GAG CTG AAG GTG CTG AAG    1815
Lys Asp Lys Val Leu Ala Ile Arg Gln Glu Glu Leu Lys Val Leu Lys
525                 530                 535                 540

AAG TCT GCC TAC CTG TCA GCC GTG GGC ACC TTC ACC TGG GTC TGC ACG    1863
Lys Ser Ala Tyr Leu Ser Ala Val Gly Thr Phe Thr Trp Val Cys Thr
                545                 550                 555

CCC TTT CTG GTG GCC TTG TGC ACA TTT GCC GTC TAC GTG ACC ATT GAC    1911
Pro Phe Leu Val Ala Leu Cys Thr Phe Ala Val Tyr Val Thr Ile Asp
                560                 565                 570

GAG AAC AAC ATC CTG GAT GCC CAG ACA GCC TTC GTG TCT TTG GCC TTG    1959
Glu Asn Asn Ile Leu Asp Ala Gln Thr Ala Phe Val Ser Leu Ala Leu
            575                 580                 585
```

```
TTC AAC ATC CTC CGG TTT CCC CTG AAC ATT CTC CCC ATG GTC ATC AGC        2007
Phe Asn Ile Leu Arg Phe Pro Leu Asn Ile Leu Pro Met Val Ile Ser
    590                 595                 600

AGC ATC GTG CAG GCG AGT GTC TCC CTC AAA CGC CTG AGG ATC TTT CTC        2055
Ser Ile Val Gln Ala Ser Val Ser Leu Lys Arg Leu Arg Ile Phe Leu
605                 610                 615                 620

TCC CAT GAG GAG CTG GAA CCT GAC AGC ATC GAG CGA CGG CCT GTC AAA        2103
Ser His Glu Glu Leu Glu Pro Asp Ser Ile Glu Arg Arg Pro Val Lys
                    625                 630                 635

GAC GGC GGG GGC ACG AAC AGC ATC ACC GTG AGG AAT GCC ACA TTC ACC        2151
Asp Gly Gly Gly Thr Asn Ser Ile Thr Val Arg Asn Ala Thr Phe Thr
                640                 645                 650

TGG GCC AGG AGC GAC CCT CCC ACA CTG AAT GGC ATC ACC TTC TCC ATC        2199
Trp Ala Arg Ser Asp Pro Pro Thr Leu Asn Gly Ile Thr Phe Ser Ile
            655                 660                 665

CCC GAA GGT GCT TTG GTG GCC GTG GTG GGC CAG GTG GGC TGC GGA AAG        2247
Pro Glu Gly Ala Leu Val Ala Val Val Gly Gln Val Gly Cys Gly Lys
        670                 675                 680

TCG TCC CTG CTC TCA GCC CTC TTG GCT GAG ATG GAC AAA GTG GAG GGG        2295
Ser Ser Leu Leu Ser Ala Leu Leu Ala Glu Met Asp Lys Val Glu Gly
685                 690                 695                 700

CAC GTG GCT ATC AAG GGC TCC GTG GCC TAT GTG CCA CAG CAG GCC TGG        2343
His Val Ala Ile Lys Gly Ser Val Ala Tyr Val Pro Gln Gln Ala Trp
                    705                 710                 715

ATT CAG AAT GAT TCT CTC CGA GAA AAC ATC CTT TTT GGA TGT CAG CTG        2391
Ile Gln Asn Asp Ser Leu Arg Glu Asn Ile Leu Phe Gly Cys Gln Leu
                720                 725                 730

GAG GAA CCA TAT TAC AGG TCC GTG ATA CAG GCC TGT GCC CTC CTC CCA        2439
Glu Glu Pro Tyr Tyr Arg Ser Val Ile Gln Ala Cys Ala Leu Leu Pro
            735                 740                 745

GAC CTG GAA ATC CTG CCC AGT GGG GAT CGG ACA GAG ATT GGC GAG AAG        2487
Asp Leu Glu Ile Leu Pro Ser Gly Asp Arg Thr Glu Ile Gly Glu Lys
        750                 755                 760

GGC GTG AAC CTG TCT GGG GGA CAG AAG CAG CGC GTG AGC CTG GCC CGG        2535
Gly Val Asn Leu Ser Gly Gly Gln Lys Gln Arg Val Ser Leu Ala Arg
765                 770                 775                 780

GCC GTG TAC TCC AAC GCT GAC ATT TAC CTC TTC GAT GAT CCC CTC TCA        2583
Ala Val Tyr Ser Asn Ala Asp Ile Tyr Leu Phe Asp Asp Pro Leu Ser
                    785                 790                 795

GCA GTG GAT GCC CAT GTG GGA AAA CAC ATC TTT GAA AAT GTG ATT GGC        2631
Ala Val Asp Ala His Val Gly Lys His Ile Phe Glu Asn Val Ile Gly
                800                 805                 810

CCC AAG GGG ATG CTG AAG AAC AAG ACG CGG ATC TTG GTC ACG CAC AGC        2679
Pro Lys Gly Met Leu Lys Asn Lys Thr Arg Ile Leu Val Thr His Ser
            815                 820                 825

ATG AGC TAC TTG CCG CAG GTG GAC GTC ATC ATC GTC ATG AGT GGC GGC        2727
Met Ser Tyr Leu Pro Gln Val Asp Val Ile Ile Val Met Ser Gly Gly
        830                 835                 840

AAG ATC TCT GAG ATG GGC TCC TAC CAG GAG CTG CTG GCT CGA GAC GGC        2775
Lys Ile Ser Glu Met Gly Ser Tyr Gln Glu Leu Leu Ala Arg Asp Gly
845                 850                 855                 860

GCC TTC GCT GAG TTC CTG CGT ACC TAT GCC AGC ACA GAG CAG GAG CAG        2823
Ala Phe Ala Glu Phe Leu Arg Thr Tyr Ala Ser Thr Glu Gln Glu Gln
                    865                 870                 875

GAT GCA GAG GAG AAC GGG GTC ACG GGC GTC AGC GGT CCA GGG AAG GAA        2871
Asp Ala Glu Glu Asn Gly Val Thr Gly Val Ser Gly Pro Gly Lys Glu
                880                 885                 890

GCA AAG CAA ATG GAG AAT GGC ATG CTG GTG ACG GAC AGT GCA GGG AAG        2919
Ala Lys Gln Met Glu Asn Gly Met Leu Val Thr Asp Ser Ala Gly Lys
            895                 900                 905
```

```
CAA CTG CAG AGA CAG CTC AGC AGC TCC TCC TCC TAT AGT GGG GAC ATC    2967
Gln Leu Gln Arg Gln Leu Ser Ser Ser Ser Ser Tyr Ser Gly Asp Ile
    910                 915                 920

AGC AGG CAC CAC AAC AGC ACC GCA GAA CTG CAG AAA GCT GAG GCC AAG    3015
Ser Arg His His Asn Ser Thr Ala Glu Leu Gln Lys Ala Glu Ala Lys
925                 930                 935                 940

AAG GAG GAG ACC TGG AAG CTG ATG GAG GCT GAC AAG GCG CAG ACA GGG    3063
Lys Glu Glu Thr Trp Lys Leu Met Glu Ala Asp Lys Ala Gln Thr Gly
                945                 950                 955

CAG GTC AAG CTT TCC GTG TAC TGG GAC TAC ATG AAG GCC ATC GGA CTC    3111
Gln Val Lys Leu Ser Val Tyr Trp Asp Tyr Met Lys Ala Ile Gly Leu
            960                 965                 970

TTC ATC TCC TTC CTC AGC ATC TTC CTT TTC ATG TGT AAC CAT GTG TCC    3159
Phe Ile Ser Phe Leu Ser Ile Phe Leu Phe Met Cys Asn His Val Ser
        975                 980                 985

GCG CTG GCT TCC AAC TAT TGG CTC AGC CTC TGG ACT GAT GAC CCC ATC    3207
Ala Leu Ala Ser Asn Tyr Trp Leu Ser Leu Trp Thr Asp Asp Pro Ile
    990                 995                 1000

GTC AAC GGG ACT CAG GAG CAC ACG AAA GTC CGG CTG AGC GTC TAT GGA    3255
Val Asn Gly Thr Gln Glu His Thr Lys Val Arg Leu Ser Val Tyr Gly
1005                1010                1015                1020

GCC CTG GGC ATT TCA CAA GGG ATC GCC GTG TTT GGC TAC TCC ATG GCC    3303
Ala Leu Gly Ile Ser Gln Gly Ile Ala Val Phe Gly Tyr Ser Met Ala
                1025                1030                1035

GTG TCC ATC GGG GGG ATC TTG GCT TCC CGC TGT CTG CAC GTG GAC CTG    3351
Val Ser Ile Gly Gly Ile Leu Ala Ser Arg Cys Leu His Val Asp Leu
            1040                1045                1050

CTG CAC AGC ATC CTG CGG TCA CCC ATG AGC TTC TTT GAG CGG ACC CCC    3399
Leu His Ser Ile Leu Arg Ser Pro Met Ser Phe Phe Glu Arg Thr Pro
        1055                1060                1065

AGT GGG AAC CTG GTG AAC CGC TTC TCC AAG GAG CTG GAC ACA GTG GAC    3447
Ser Gly Asn Leu Val Asn Arg Phe Ser Lys Glu Leu Asp Thr Val Asp
    1070                1075                1080

TCC ATG ATC CCG GAG GTC ATC AAG ATG TTC ATG GGC TCC CTG TTC AAC    3495
Ser Met Ile Pro Glu Val Ile Lys Met Phe Met Gly Ser Leu Phe Asn
1085                1090                1095                1100

GTC ATT GGT GCC TGC ATC GTT ATC CTG CTG GCC ACG CCC ATC GCC GCC    3543
Val Ile Gly Ala Cys Ile Val Ile Leu Leu Ala Thr Pro Ile Ala Ala
                1105                1110                1115

ATC ATC ATC CCG CCC CTT GGC CTC ATC TAC TTC TTC GTC CAG AGG TTC    3591
Ile Ile Ile Pro Pro Leu Gly Leu Ile Tyr Phe Phe Val Gln Arg Phe
            1120                1125                1130

TAC GTG GCT TCC TCC CGG CAG CTG AAG CGC CTC GAG TCG GTC AGC CGC    3639
Tyr Val Ala Ser Ser Arg Gln Leu Lys Arg Leu Glu Ser Val Ser Arg
        1135                1140                1145

TCC CCG GTC TAT TCC CAT TTC AAC GAG ACC TTG CTG GGG GTC AGC GTC    3687
Ser Pro Val Tyr Ser His Phe Asn Glu Thr Leu Leu Gly Val Ser Val
    1150                1155                1160

ATT CGA GCC TTC GAG GAG CAG GAG CGC TTC ATC CAC CAG AGT GAC CTG    3735
Ile Arg Ala Phe Glu Glu Gln Glu Arg Phe Ile His Gln Ser Asp Leu
1165                1170                1175                1180

AAG GTG GAC GAG AAC CAG AAG GCC TAT TAC CCC AGC ATC GTG GCC AAC    3783
Lys Val Asp Glu Asn Gln Lys Ala Tyr Tyr Pro Ser Ile Val Ala Asn
                1185                1190                1195

AGG TGG CTG GCC GTG CGG CTG GAG TGT GTG GGC AAC TGC ATC GTT CTG    3831
Arg Trp Leu Ala Val Arg Leu Glu Cys Val Gly Asn Cys Ile Val Leu
            1200                1205                1210

TTT GCT GCC CTG TTT GCG GTG ATC TCC AGG CAC AGC CTC AGT GCT GGC    3879
Phe Ala Ala Leu Phe Ala Val Ile Ser Arg His Ser Leu Ser Ala Gly
        1215                1220                1225
```

```
TTG GTG GGC CTC TCA GTG TCT TAC TCA TTG CAG GTC ACC ACG TAC TTG      3927
Leu Val Gly Leu Ser Val Ser Tyr Ser Leu Gln Val Thr Thr Tyr Leu
    1230                1235                1240

AAC TGG CTG GTT CGG ATG TCA TCT GAA ATG GAA ACC AAC ATC GTG GCC      3975
Asn Trp Leu Val Arg Met Ser Ser Glu Met Glu Thr Asn Ile Val Ala
1245                1250                1255                1260

GTG GAG AGG CTC AAG GAG TAT TCA GAG ACT GAG AAG GAG GCG CCC TGG      4023
Val Glu Arg Leu Lys Glu Tyr Ser Glu Thr Glu Lys Glu Ala Pro Trp
                1265                1270                1275

CAA ATC CAG GAG ACA GCT CCG CCC AGC AGC TGG CCC CAG GTG GGC CGA      4071
Gln Ile Gln Glu Thr Ala Pro Pro Ser Ser Trp Pro Gln Val Gly Arg
            1280                1285                1290

GTG GAA TTC CGG AAC TAC TGC CTG CGC TAC CGA GAG GAC CTG GAC TTC      4119
Val Glu Phe Arg Asn Tyr Cys Leu Arg Tyr Arg Glu Asp Leu Asp Phe
        1295                1300                1305

GTT CTC AGG CAC ATC AAT GTC ACG ATC AAT GGG GGA GAA AAG GTC GGC      4167
Val Leu Arg His Ile Asn Val Thr Ile Asn Gly Gly Glu Lys Val Gly
    1310                1315                1320

ATC GTG GGG CGG ACG GGA GCT GGG AAG TCG TCC CTG ACC CTG GGC TTA      4215
Ile Val Gly Arg Thr Gly Ala Gly Lys Ser Ser Leu Thr Leu Gly Leu
1325                1330                1335                1340

TTT CGG ATC AAC GAG TCT GCC GAA GGA GAG ATC ATC ATC GAT GGC ATC      4263
Phe Arg Ile Asn Glu Ser Ala Glu Gly Glu Ile Ile Ile Asp Gly Ile
                1345                1350                1355

AAC ATC GCC AAG ATC GGC CTG CAC GAC CTC CGC TTC AAG ATC ACC ATC      4311
Asn Ile Ala Lys Ile Gly Leu His Asp Leu Arg Phe Lys Ile Thr Ile
            1360                1365                1370

ATC CCC CAG GAC CCT GTT TTG TTT TCG GGT TCC CTC CGA ATG AAC CTG      4359
Ile Pro Gln Asp Pro Val Leu Phe Ser Gly Ser Leu Arg Met Asn Leu
        1375                1380                1385

GAC CCA TTC AGC CAG TAC TCG GAT GAA GAA GTC TGG ACG TCC CTG GAG      4407
Asp Pro Phe Ser Gln Tyr Ser Asp Glu Glu Val Trp Thr Ser Leu Glu
    1390                1395                1400

CTG GCC CAC CTG AAG GAC TTC GTG TCA GCC CTT CCT GAC AAG CTA GAC      4455
Leu Ala His Leu Lys Asp Phe Val Ser Ala Leu Pro Asp Lys Leu Asp
1405                1410                1415                1420

CAT GAA TGT GCA GAA GGC GGG GAG AAC CTC AGT GTC GGG CAG CGC CAG      4503
His Glu Cys Ala Glu Gly Gly Glu Asn Leu Ser Val Gly Gln Arg Gln
                1425                1430                1435

CTT GTG TGC CTA GCC CGG GCC CTG CTG AGG AAG ACG AAG ATC CTT GTG      4551
Leu Val Cys Leu Ala Arg Ala Leu Leu Arg Lys Thr Lys Ile Leu Val
            1440                1445                1450

TTG GAT GAG GCC ACG GCA GCC GTG GAC CTG GAA ACG GAC GAC CTC ATC      4599
Leu Asp Glu Ala Thr Ala Ala Val Asp Leu Glu Thr Asp Asp Leu Ile
        1455                1460                1465

CAG TCC ACC ATC CGG ACA CAG TTC GAG GAC TGC ACC GTC CTC ACC ATC      4647
Gln Ser Thr Ile Arg Thr Gln Phe Glu Asp Cys Thr Val Leu Thr Ile
    1470                1475                1480

GCC CAC CGG CTC AAC ACC ATC ATG GAC TAC ACA AGG GTG ATC GTC TTG      4695
Ala His Arg Leu Asn Thr Ile Met Asp Tyr Thr Arg Val Ile Val Leu
1485                1490                1495                1500

GAC AAA GGA GAA ATC CAG GAG TAC GGC GCC CCA TCG GAC CTC CTG CAG      4743
Asp Lys Gly Glu Ile Gln Glu Tyr Gly Ala Pro Ser Asp Leu Leu Gln
                1505                1510                1515

CAG AGA GGT CTT TTC TAC AGC ATG GCC AAA GAC GCC GGC TTG GTG            4788
Gln Arg Gly Leu Phe Tyr Ser Met Ala Lys Asp Ala Gly Leu Val
            1520                1525                1530

TGAGCCCCAG AGCTGGCATA TCTGGTCAGA ACTGCAGGGC CTATATGCCA GCGCCCCAGG    4848

GAGGAGTCAG TACCCCTGGT AAACCAAGCC TCCCACACTG AAACCAAAAC ATAAAAACCA    4908
```

```
AACCCAGACA ACCAAAACAT ATTCAAAGCA GCAGCCACCG CCATCCGGTC CCCTGCCTGG      4968

AACTGGCTGT GAAGACCCAG GAGAGACAGA GATGCGAACC ACC                       5011
```

(2) INFORMATION FOR SEQ ID NO:4:

(i) SEQUENCE CHARACTERISTICS:
        (A) LENGTH: 1531 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Leu Arg Gly Phe Cys Ser Ala Asp Gly Ser Asp Pro Leu Trp
 1               5                  10                  15

Asp Trp Asn Val Thr Trp Asn Thr Ser Asn Pro Asp Phe Thr Lys Cys
                20                  25                  30

Phe Gln Asn Thr Val Leu Val Trp Val Pro Cys Phe Tyr Leu Trp Ala
            35                  40                  45

Cys Phe Pro Phe Tyr Phe Leu Tyr Leu Ser Arg His Asp Arg Gly Tyr
        50                  55                  60

Ile Gln Met Thr Pro Leu Asn Lys Thr Lys Thr Ala Leu Gly Phe Leu
65                  70                  75                  80

Leu Trp Ile Val Cys Trp Ala Asp Leu Phe Tyr Ser Phe Trp Glu Arg
                85                  90                  95

Ser Arg Gly Ile Phe Leu Ala Pro Val Phe Leu Val Ser Pro Thr Leu
               100                 105                 110

Leu Gly Ile Thr Thr Leu Leu Ala Thr Phe Leu Ile Gln Leu Glu Arg
            115                 120                 125

Arg Lys Gly Val Gln Ser Ser Gly Ile Met Leu Thr Phe Trp Leu Val
        130                 135                 140

Ala Leu Val Cys Ala Leu Ala Ile Leu Arg Ser Lys Ile Met Thr Ala
145                 150                 155                 160

Leu Lys Glu Asp Ala Gln Val Asp Leu Phe Arg Asp Ile Thr Phe Tyr
                165                 170                 175

Val Tyr Phe Ser Leu Leu Leu Ile Gln Leu Val Leu Ser Cys Phe Ser
               180                 185                 190

Asp Arg Ser Pro Leu Phe Ser Glu Thr Ile His Asp Pro Asn Pro Cys
            195                 200                 205

Pro Glu Ser Ser Ala Ser Phe Leu Ser Arg Ile Thr Phe Trp Trp Ile
        210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
               260                 265                 270

Val Lys Val Val Tyr Ser Ser Lys Asp Pro Ala Gln Pro Lys Glu Ser
            275                 280                 285

Ser Lys Val Asp Ala Asn Glu Glu Val Glu Ala Leu Ile Val Lys Ser
        290                 295                 300

Pro Gln Lys Glu Trp Asn Pro Ser Leu Phe Lys Val Leu Tyr Lys Thr
305                 310                 315                 320

Phe Gly Pro Tyr Phe Leu Met Ser Phe Phe Phe Lys Ala Ile His Asp
                325                 330                 335
```

-continued

```
Leu Met Met Phe Ser Gly Pro Gln Ile Leu Lys Leu Leu Ile Lys Phe
        340                 345                 350

Val Asn Asp Thr Lys Ala Pro Asp Trp Gln Gly Tyr Phe Tyr Thr Val
        355                 360                 365

Leu Leu Phe Val Thr Ala Cys Leu Gln Thr Leu Val Leu His Gln Tyr
        370                 375                 380

Phe His Ile Cys Phe Val Ser Gly Met Arg Ile Lys Thr Ala Val Ile
385                 390                 395                 400

Gly Ala Val Tyr Arg Lys Ala Leu Val Ile Thr Asn Ser Ala Arg Lys
                405                 410                 415

Ser Ser Thr Val Gly Glu Ile Val Asn Leu Met Ser Val Asp Ala Gln
                420                 425                 430

Arg Phe Met Asp Leu Ala Thr Tyr Ile Asn Met Ile Trp Ser Ala Pro
        435                 440                 445

Leu Gln Val Ile Leu Ala Leu Tyr Leu Leu Trp Leu Asn Leu Gly Pro
        450                 455                 460

Ser Val Leu Ala Gly Val Ala Val Met Val Leu Met Val Pro Val Asn
465                 470                 475                 480

Ala Val Met Ala Met Lys Thr Lys Thr Tyr Gln Val Ala His Met Lys
                485                 490                 495

Ser Lys Asp Asn Arg Ile Lys Leu Met Asn Glu Ile Leu Asn Gly Ile
                500                 505                 510

Lys Val Leu Lys Leu Tyr Ala Trp Glu Leu Ala Phe Lys Asp Lys Val
        515                 520                 525

Leu Ala Ile Arg Gln Glu Glu Leu Lys Val Leu Lys Lys Ser Ala Tyr
        530                 535                 540

Leu Ser Ala Val Gly Thr Phe Thr Trp Val Cys Thr Pro Phe Leu Val
545                 550                 555                 560

Ala Leu Cys Thr Phe Ala Val Tyr Val Thr Ile Asp Glu Asn Asn Ile
                565                 570                 575

Leu Asp Ala Gln Thr Ala Phe Val Ser Leu Ala Leu Phe Asn Ile Leu
                580                 585                 590

Arg Phe Pro Leu Asn Ile Leu Pro Met Val Ile Ser Ser Ile Val Gln
        595                 600                 605

Ala Ser Val Ser Leu Lys Arg Leu Arg Ile Phe Leu Ser His Glu Glu
        610                 615                 620

Leu Glu Pro Asp Ser Ile Glu Arg Arg Pro Val Lys Asp Gly Gly Gly
625                 630                 635                 640

Thr Asn Ser Ile Thr Val Arg Asn Ala Thr Phe Thr Trp Ala Arg Ser
                645                 650                 655

Asp Pro Pro Thr Leu Asn Gly Ile Thr Phe Ser Ile Pro Glu Gly Ala
                660                 665                 670

Leu Val Ala Val Val Gly Gln Val Gly Cys Gly Lys Ser Ser Leu Leu
        675                 680                 685

Ser Ala Leu Leu Ala Glu Met Asp Lys Val Glu Gly His Val Ala Ile
        690                 695                 700

Lys Gly Ser Val Ala Tyr Val Pro Gln Gln Ala Trp Ile Gln Asn Asp
705                 710                 715                 720

Ser Leu Arg Glu Asn Ile Leu Phe Gly Cys Gln Leu Glu Glu Pro Tyr
                725                 730                 735

Tyr Arg Ser Val Ile Gln Ala Cys Ala Leu Leu Pro Asp Leu Glu Ile
                740                 745                 750

Leu Pro Ser Gly Asp Arg Thr Glu Ile Gly Glu Lys Gly Val Asn Leu
        755                 760                 765
```

-continued

```
Ser Gly Gly Gln Lys Gln Arg Val Ser Leu Ala Arg Ala Val Tyr Ser
    770                 775                 780
Asn Ala Asp Ile Tyr Leu Phe Asp Asp Pro Leu Ser Ala Val Asp Ala
785                 790                 795                 800
His Val Gly Lys His Ile Phe Glu Asn Val Ile Gly Pro Lys Gly Met
                    805                 810                 815
Leu Lys Asn Lys Thr Arg Ile Leu Val Thr His Ser Met Ser Tyr Leu
                820                 825                 830
Pro Gln Val Asp Val Ile Ile Val Met Ser Gly Gly Lys Ile Ser Glu
                835                 840                 845
Met Gly Ser Tyr Gln Glu Leu Leu Ala Arg Asp Gly Ala Phe Ala Glu
850                 855                 860
Phe Leu Arg Thr Tyr Ala Ser Thr Glu Gln Glu Gln Asp Ala Glu Glu
865                 870                 875                 880
Asn Gly Val Thr Gly Val Ser Gly Pro Gly Lys Glu Ala Lys Gln Met
                    885                 890                 895
Glu Asn Gly Met Leu Val Thr Asp Ser Ala Gly Lys Gln Leu Gln Arg
                900                 905                 910
Gln Leu Ser Ser Ser Ser Ser Tyr Ser Gly Asp Ile Ser Arg His His
                915                 920                 925
Asn Ser Thr Ala Glu Leu Gln Lys Ala Glu Ala Lys Lys Glu Glu Thr
            930                 935                 940
Trp Lys Leu Met Glu Ala Asp Lys Ala Gln Thr Gly Gln Val Lys Leu
945                 950                 955                 960
Ser Val Tyr Trp Asp Tyr Met Lys Ala Ile Gly Leu Phe Ile Ser Phe
                    965                 970                 975
Leu Ser Ile Phe Leu Phe Met Cys Asn His Val Ser Ala Leu Ala Ser
                980                 985                 990
Asn Tyr Trp Leu Ser Leu Trp Thr Asp Asp Pro Ile Val Asn Gly Thr
                995                 1000                1005
Gln Glu His Thr Lys Val Arg Leu Ser Val Tyr Gly Ala Leu Gly Ile
    1010                1015                1020
Ser Gln Gly Ile Ala Val Phe Gly Tyr Ser Met Ala Val Ser Ile Gly
1025                1030                1035                1040
Gly Ile Leu Ala Ser Arg Cys Leu His Val Asp Leu Leu His Ser Ile
                    1045                1050                1055
Leu Arg Ser Pro Met Ser Phe Phe Glu Arg Thr Pro Ser Gly Asn Leu
                1060                1065                1070
Val Asn Arg Phe Ser Lys Glu Leu Asp Thr Val Asp Ser Met Ile Pro
                1075                1080                1085
Glu Val Ile Lys Met Phe Met Gly Ser Leu Phe Asn Val Ile Gly Ala
                1090                1095                1100
Cys Ile Val Ile Leu Leu Ala Thr Pro Ile Ala Ala Ile Ile Ile Pro
1105                1110                1115                1120
Pro Leu Gly Leu Ile Tyr Phe Phe Val Gln Arg Phe Tyr Val Ala Ser
                    1125                1130                1135
Ser Arg Gln Leu Lys Arg Leu Glu Ser Val Ser Arg Ser Pro Val Tyr
                1140                1145                1150
Ser His Phe Asn Glu Thr Leu Leu Gly Val Ser Val Ile Arg Ala Phe
                1155                1160                1165
Glu Glu Gln Glu Arg Phe Ile His Gln Ser Asp Leu Lys Val Asp Glu
                1170                1175                1180
Asn Gln Lys Ala Tyr Tyr Pro Ser Ile Val Ala Asn Arg Trp Leu Ala
```

```
                1185                 1190                 1195                  1200
Val Arg Leu Glu Cys Val Gly Asn Cys Ile Val Phe Ala Ala Leu
                    1205                  1210                 1215

Phe Ala Val Ile Ser Arg His Ser Leu Ser Ala Gly Leu Val Gly Leu
                1220                  1225                 1230

Ser Val Ser Tyr Ser Leu Gln Val Thr Thr Tyr Leu Asn Trp Leu Val
                1235                  1240                 1245

Arg Met Ser Ser Glu Met Glu Thr Asn Ile Val Ala Val Glu Arg Leu
                1250                  1255                 1260

Lys Glu Tyr Ser Glu Thr Glu Lys Glu Ala Pro Trp Gln Ile Gln Glu
1265                 1270                 1275                 1280

Thr Ala Pro Pro Ser Ser Trp Pro Gln Val Gly Arg Val Glu Phe Arg
                1285                 1290                  1295

Asn Tyr Cys Leu Arg Tyr Arg Glu Asp Leu Asp Phe Val Leu Arg His
                1300                 1305                  1310

Ile Asn Val Thr Ile Asn Gly Gly Glu Lys Val Gly Ile Val Gly Arg
                1315                 1320                  1325

Thr Gly Ala Gly Lys Ser Ser Leu Thr Leu Gly Leu Phe Arg Ile Asn
                1330                 1335                  1340

Glu Ser Ala Glu Gly Glu Ile Ile Ile Asp Gly Ile Asn Ile Ala Lys
1345                 1350                 1355                 1360

Ile Gly Leu His Asp Leu Arg Phe Lys Ile Thr Ile Ile Pro Gln Asp
                1365                 1370                  1375

Pro Val Leu Phe Ser Gly Ser Leu Arg Met Asn Leu Asp Pro Phe Ser
                1380                 1385                  1390

Gln Tyr Ser Asp Glu Glu Val Trp Thr Ser Leu Glu Leu Ala His Leu
                1395                 1400                  1405

Lys Asp Phe Val Ser Ala Leu Pro Asp Lys Leu Asp His Glu Cys Ala
                1410                 1415                  1420

Glu Gly Gly Glu Asn Leu Ser Val Gly Gln Arg Gln Leu Val Cys Leu
1425                 1430                 1435                 1440

Ala Arg Ala Leu Leu Arg Lys Thr Lys Ile Leu Val Leu Asp Glu Ala
                1445                 1450                 1455

Thr Ala Ala Val Asp Leu Glu Thr Asp Asp Leu Ile Gln Ser Thr Ile
                1460                 1465                 1470

Arg Thr Gln Phe Glu Asp Cys Thr Val Leu Thr Ile Ala His Arg Leu
                1475                 1480                 1485

Asn Thr Ile Met Asp Tyr Thr Arg Val Ile Val Leu Asp Lys Gly Glu
                1490                 1495                 1500

Ile Gln Glu Tyr Gly Ala Pro Ser Asp Leu Leu Gln Gln Arg Gly Leu
1505                 1510                 1515                 1520

Phe Tyr Ser Met Ala Lys Asp Ala Gly Leu Val
                1525                  1530

(2) INFORMATION FOR SEQ ID NO:5:

(i) SEQUENCE CHARACTERISTICS:
        (A) LENGTH: 5889 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 6   4589
```

(xi) SEQUENCE DESCRIPTION: SEQ ID NO:5:

```
CCCGC ATG GCG CTG CGC AGC TTC TGC AGC GCT GAT GGC TCC GAT CCA              47
      Met Ala Leu Arg Ser Phe Cys Ser Ala Asp Gly Ser Asp Pro
        1               5                  10

CTC TGG GAC TGG AAT GTC ACA TGG CAC ACC AGC AAC CCC GAC TTT ACC            95
Leu Trp Asp Trp Asn Val Thr Trp His Thr Ser Asn Pro Asp Phe Thr
 15              20                  25                  30

AAG TGC TTT CAG AAC ACG GTC CTC ACA TGG GTG CCT TGT TTC TAC CTC           143
Lys Cys Phe Gln Asn Thr Val Leu Thr Trp Val Pro Cys Phe Tyr Leu
                 35                  40                  45

TGG TCC TGT TTC CCC CTC TAC TTC TTC TAT CTC TCT CGC CAT GAC CGG           191
Trp Ser Cys Phe Pro Leu Tyr Phe Phe Tyr Leu Ser Arg His Asp Arg
                     50                  55                  60

GGC TAC ATC CAG ATG ACA CAC CTC AAC AAA ACC AAA ACT GCC TTA GGA           239
Gly Tyr Ile Gln Met Thr His Leu Asn Lys Thr Lys Thr Ala Leu Gly
                         65                  70                  75

TTC TTT CTG TGG ATC ATC TGC TGG GCA GAC CTC TTC TAC TCT TTC TGG           287
Phe Phe Leu Trp Ile Ile Cys Trp Ala Asp Leu Phe Tyr Ser Phe Trp
 80                  85                  90

GAA AGA AGT CAG GGA GTG CTC CGA GCC CCG GTG TTA CTG GTC AGC CCA           335
Glu Arg Ser Gln Gly Val Leu Arg Ala Pro Val Leu Leu Val Ser Pro
 95                 100                 105                 110

ACA CTG CTG GGC ATC ACC ATG CTG CTC GCC ACC TTT TTG ATA CAG CTT           383
Thr Leu Leu Gly Ile Thr Met Leu Leu Ala Thr Phe Leu Ile Gln Leu
                115                 120                 125

GAA CGG AGG AAG GGA GTC CAA TCC TCG GGA ATT ATG CTT ACT TTC TGG           431
Glu Arg Arg Lys Gly Val Gln Ser Ser Gly Ile Met Leu Thr Phe Trp
                    130                 135                 140

CTC GTA GCC CTA CTC TGT GCC CTT GCC ATC TTG AGA TCT AAG ATC ATC           479
Leu Val Ala Leu Leu Cys Ala Leu Ala Ile Leu Arg Ser Lys Ile Ile
                        145                 150                 155

TCT GCC TTA AAA AAG GAT GCT CAT GTG GAC GTG TTT CGA GAT TCC ACG           527
Ser Ala Leu Lys Lys Asp Ala His Val Asp Val Phe Arg Asp Ser Thr
                            160                 165                 170

TTC TAT CTG TAC TTC ACC CTT GTG CTT GTT CAG CTC GTG CTG TCC TGC           575
Phe Tyr Leu Tyr Phe Thr Leu Val Leu Val Gln Leu Val Leu Ser Cys
175                 180                 185                 190

TTC TCA GAC TGC TCA CCC CTG TTC TCT GAA ACT GTC CAT GAC CGG AAT           623
Phe Ser Asp Cys Ser Pro Leu Phe Ser Glu Thr Val His Asp Arg Asn
                    195                 200                 205

CCA TGC CCA GAA TCC AGT GCC TCT TTC CTT TCC AGG ATT ACT TTC TGG           671
Pro Cys Pro Glu Ser Ser Ala Ser Phe Leu Ser Arg Ile Thr Phe Trp
                        210                 215                 220

TGG ATT ACA GGG ATG ATG GTG CAC GGC TAC CGC CAG CCC CTG GAG AGC           719
Trp Ile Thr Gly Met Met Val His Gly Tyr Arg Gln Pro Leu Glu Ser
                            225                 230                 235

AGT GAC CTC TGG TCA TTG AAT AAG GAG GAC ACA TCA GAA GAA GTG GTA           767
Ser Asp Leu Trp Ser Leu Asn Lys Glu Asp Thr Ser Glu Glu Val Val
    240                 245                 250

CCT GTG CTG GTG AAT AAC TGG AAG AAG GAA TGT GAT AAG TCA AGG AAG           815
Pro Val Leu Val Asn Asn Trp Lys Lys Glu Cys Asp Lys Ser Arg Lys
255                 260                 265                 270

CAG CCT GTA CGG ATT GTG TAT GCC CCT CCC AAA GAT CCC AGC AAG CCT           863
Gln Pro Val Arg Ile Val Tyr Ala Pro Pro Lys Asp Pro Ser Lys Pro
                275                 280                 285

AAG GGA AGT TCC CAG TTG GAT GTG AAT GAG GAG GTG GAG GCA CTG ATT           911
Lys Gly Ser Ser Gln Leu Asp Val Asn Glu Glu Val Glu Ala Leu Ile
                    290                 295                 300

GTC AAG TCA CCC CAC AAG GAT CGG GAG CCC TCT CTG TTC AAG GTG TTA           959
Val Lys Ser Pro His Lys Asp Arg Glu Pro Ser Leu Phe Lys Val Leu
```

```
                305                    310                    315
TAC AAG ACT TTT GGT CCC TAC TTC CTC ATG AGC TTC CTG TAC AAG GCC       1007
Tyr Lys Thr Phe Gly Pro Tyr Phe Leu Met Ser Phe Leu Tyr Lys Ala
    320                 325                 330

CTT CAT GAC CTG ATG ATG TTT GCC GGC CCC AAG ATC TTG GAA TTG ATT       1055
Leu His Asp Leu Met Met Phe Ala Gly Pro Lys Ile Leu Glu Leu Ile
335                 340                 345                 350

ATC AAC TTC GTG AAT GAC AGG GAG GCT CCC GAC TGG CAG GGC TAC TTT       1103
Ile Asn Phe Val Asn Asp Arg Glu Ala Pro Asp Trp Gln Gly Tyr Phe
                355                 360                 365

TAC ACA GCA CTG CTG TTT GTC AGC GCC TGT CTG CAG ACA CTG GCA CTC       1151
Tyr Thr Ala Leu Leu Phe Val Ser Ala Cys Leu Gln Thr Leu Ala Leu
            370                 375                 380

CAC CAG TAC TTT CAT ATC TGC TTC GTC AGT GGC ATG CGC ATC AAG ACT       1199
His Gln Tyr Phe His Ile Cys Phe Val Ser Gly Met Arg Ile Lys Thr
        385                 390                 395

GCT GTG GTG GGC GCT GTC TAT CGT AAG GCT CTT TTG ATC ACC AAT GCA       1247
Ala Val Val Gly Ala Val Tyr Arg Lys Ala Leu Leu Ile Thr Asn Ala
    400                 405                 410

GCT AGA AAA TCT TCC ACG GTC GGA GAG ATT GTC AAC CTC ATG TCC GTG       1295
Ala Arg Lys Ser Ser Thr Val Gly Glu Ile Val Asn Leu Met Ser Val
415                 420                 425                 430

GAT GCT CAG CGC TTC ATG GAC TTG GCC ACG TAC ATT AAC ATG ATC TGG       1343
Asp Ala Gln Arg Phe Met Asp Leu Ala Thr Tyr Ile Asn Met Ile Trp
                435                 440                 445

TCA GCC CCT CTG CAA GTC ATC CTA GCC CTC TAC TTC CTG TGG CTG AGC       1391
Ser Ala Pro Leu Gln Val Ile Leu Ala Leu Tyr Phe Leu Trp Leu Ser
            450                 455                 460

CTG GGC CCT TCT GTG CTG GCT GGA GTG GCT GTG ATG ATT CTC ATG GTA       1439
Leu Gly Pro Ser Val Leu Ala Gly Val Ala Val Met Ile Leu Met Val
        465                 470                 475

CCC TTA AAT GCT GTG ATG GCC ATG AAG ACC AAG ACC TAC CAG GTG GCA       1487
Pro Leu Asn Ala Val Met Ala Met Lys Thr Lys Thr Tyr Gln Val Ala
    480                 485                 490

CAC ATG AAG AGC AAA GAC AAC CGA ATC AAG CTG ATG AAC GAG ATC CTC       1535
His Met Lys Ser Lys Asp Asn Arg Ile Lys Leu Met Asn Glu Ile Leu
495                 500                 505                 510

AAT GGG ATC AAA GTC CTC AAG CTG TAC GCC TGG GAG CTG GCC TTC CAG       1583
Asn Gly Ile Lys Val Leu Lys Leu Tyr Ala Trp Glu Leu Ala Phe Gln
                515                 520                 525

GAC AAA GTC ATG AGC ATC AGG CAG GAG GAG CTC AAG GTG CTG AAG AAA       1631
Asp Lys Val Met Ser Ile Arg Gln Glu Glu Leu Lys Val Leu Lys Lys
            530                 535                 540

TCT GCC TAC CTG GCA GCT GTA GGC ACA TTC ACG TGG GTG TGC ACA CCT       1679
Ser Ala Tyr Leu Ala Ala Val Gly Thr Phe Thr Trp Val Cys Thr Pro
        545                 550                 555

TTC CTG GTG GCC CTG TCA ACC TTT GCT GTC TTT GTG ACT GTG GAT GAG       1727
Phe Leu Val Ala Leu Ser Thr Phe Ala Val Phe Val Thr Val Asp Glu
    560                 565                 570

AGA AAT ATC CTA GAT GCA AAG AAA GCC TTT GTG TCC CTA GCC CTG TTC       1775
Arg Asn Ile Leu Asp Ala Lys Lys Ala Phe Val Ser Leu Ala Leu Phe
575                 580                 585                 590

AAT ATC TTG CGC TTC CCA CTC AAC ATC CTG CCC ATG GTT ATC AGC AGC       1823
Asn Ile Leu Arg Phe Pro Leu Asn Ile Leu Pro Met Val Ile Ser Ser
                595                 600                 605

ATT GTG CAG GCC AGC GTG TCC CTC AAG CGT CTC AGG ATT TTT CTG TCT       1871
Ile Val Gln Ala Ser Val Ser Leu Lys Arg Leu Arg Ile Phe Leu Ser
            610                 615                 620

CAT GAG GAG CTG GAG CCA GAC AGC ATT GAG CGG AGG TCG ATC AAG AGT       1919
His Glu Glu Leu Glu Pro Asp Ser Ile Glu Arg Arg Ser Ile Lys Ser
```

-continued

```
              625                 630                 635
GGA GAA GGG AAT AGC ATC ACT GTG AAG AAT GCA ACC TTC ACT TGG GCC      1967
Gly Glu Gly Asn Ser Ile Thr Val Lys Asn Ala Thr Phe Thr Trp Ala
        640                 645                 650

AGG GGT GAA CCT CCC ACA CTG AAT GGC ATC ACC TTC TCC ATT CCT GAA      2015
Arg Gly Glu Pro Pro Thr Leu Asn Gly Ile Thr Phe Ser Ile Pro Glu
655                 660                 665                 670

GGA GCC CTT GTG GCC GTG GTG GGC CAG GTA GGC TGC GGG AAG TCA TCT      2063
Gly Ala Leu Val Ala Val Val Gly Gln Val Gly Cys Gly Lys Ser Ser
                675                 680                 685

CTG CTG TCA GCC CTG CTG GCT GAG ATG GAC AAG GTG GAG GGA CAT GTG      2111
Leu Leu Ser Ala Leu Leu Ala Glu Met Asp Lys Val Glu Gly His Val
            690                 695                 700

ACT CTC AAG GGC TCC GTG GCC TAC GTG CCC CAG CAG GCC TGG ATT CAG      2159
Thr Leu Lys Gly Ser Val Ala Tyr Val Pro Gln Gln Ala Trp Ile Gln
        705                 710                 715

AAT GAC TCT CTC CGA GAG AAC ATA CTG TTT GGG CAC CCC CTG CAG GAA      2207
Asn Asp Ser Leu Arg Glu Asn Ile Leu Phe Gly His Pro Leu Gln Glu
720                 725                 730

AAT TAC TAC AAG GCA GTT ATG GAA GCC TGT GCC CTT CTT CCA GAT TTG      2255
Asn Tyr Tyr Lys Ala Val Met Glu Ala Cys Ala Leu Leu Pro Asp Leu
735                 740                 745                 750

GAA ATC CTG CCC AGT GGG GAC CGC ACA GAG ATC GGT GAG AAG GGT GTG      2303
Glu Ile Leu Pro Ser Gly Asp Arg Thr Glu Ile Gly Glu Lys Gly Val
                755                 760                 765

AAC CTG TCA GGG GGC CAG AAG CAG CGT GTG AGC CTG GCC CGG GCT GTG      2351
Asn Leu Ser Gly Gly Gln Lys Gln Arg Val Ser Leu Ala Arg Ala Val
            770                 775                 780

TAC TCT AAC TCT GAC ATC TAC CTC TTT GAT GAC CCC CTC TCG GCT GTG      2399
Tyr Ser Asn Ser Asp Ile Tyr Leu Phe Asp Asp Pro Leu Ser Ala Val
        785                 790                 795

GAT GCA CAT GTT GGG AAG CAC ATC TTT GAG AAG GTG GTT GGT CCC ATG      2447
Asp Ala His Val Gly Lys His Ile Phe Glu Lys Val Val Gly Pro Met
    800                 805                 810

GGC CTA CTG AAG AAC AAG ACA CGG ATC CTG GTC ACC CAT GGT ATC AGC      2495
Gly Leu Leu Lys Asn Lys Thr Arg Ile Leu Val Thr His Gly Ile Ser
815                 820                 825                 830

TAC CTG CCC CAA GTG GAT GTC ATC ATT GTC ATG AGT GGC GGC AAG ATC      2543
Tyr Leu Pro Gln Val Asp Val Ile Ile Val Met Ser Gly Gly Lys Ile
                835                 840                 845

TCA GAG ATG GGT TCT TAT CAG GAG CTG CTA GAC CGG GAT GGG GCC TTC      2591
Ser Glu Met Gly Ser Tyr Gln Glu Leu Leu Asp Arg Asp Gly Ala Phe
            850                 855                 860

GCT GAG TTC CTG CGC ACC TAT GCC AAC GCT GAG CAG GAC CTG GCC TCG      2639
Ala Glu Phe Leu Arg Thr Tyr Ala Asn Ala Glu Gln Asp Leu Ala Ser
        865                 870                 875

GAG GAT GAC AGT GTC AGT GGT TCA GGG AAG GAG TCA AAG CCG GTG GAA      2687
Glu Asp Asp Ser Val Ser Gly Ser Gly Lys Glu Ser Lys Pro Val Glu
    880                 885                 890

AAT GGG ATG CTG GTG ACA GAC ACC GTA GGA AAG CAC CTG CAG AGG CAT      2735
Asn Gly Met Leu Val Thr Asp Thr Val Gly Lys His Leu Gln Arg His
895                 900                 905                 910

CTC AGC AAC TCG TCT TCC CAC AGT GGG GAT ACC AGC CAG CAA CAC AGC      2783
Leu Ser Asn Ser Ser Ser His Ser Gly Asp Thr Ser Gln Gln His Ser
                915                 920                 925

AGC ATA GCC GAA CTG CAG AAG GCT GGA GCT AAG GAG GAG ACG TGG AAG      2831
Ser Ile Ala Glu Leu Gln Lys Ala Gly Ala Lys Glu Glu Thr Trp Lys
            930                 935                 940

CTA ATG GAA GCA GAC AAG GCC CAG ACA GGG CAG GTG CAG CTG TCA GTG      2879
Leu Met Glu Ala Asp Lys Ala Gln Thr Gly Gln Val Gln Leu Ser Val
```

```
                 945                  950                 955
TAC TGG AAC TAC ATG AAG GCC ATT GGC CTC TTC ATC ACC TTC TTG AGT       2927
Tyr Trp Asn Tyr Met Lys Ala Ile Gly Leu Phe Ile Thr Phe Leu Ser
        960                  965                 970

ATC TTC CTT TTC CTG TGC AAC CAT GTA TCT GCA CTG GCC TCT AAC TAT       2975
Ile Phe Leu Phe Leu Cys Asn His Val Ser Ala Leu Ala Ser Asn Tyr
975                 980                 985                 990

TGG CTG AGC CTC TGG ACA GAT GAC CCC CCT GTT GTC AAT GGG ACT CAG       3023
Trp Leu Ser Leu Trp Thr Asp Asp Pro Pro Val Val Asn Gly Thr Gln
                    995                1000                1005

GCG AAC AGG AAT TTT CGG CTG AGT GTC TAT GGG GCC TTG GGC ATC TTG       3071
Ala Asn Arg Asn Phe Arg Leu Ser Val Tyr Gly Ala Leu Gly Ile Leu
            1010                1015                1020

CAA GGT GCA GCA ATA TTT GGC TAC TCC ATG GCT GTG TCC ATC GGG GGC       3119
Gln Gly Ala Ala Ile Phe Gly Tyr Ser Met Ala Val Ser Ile Gly Gly
        1025                1030                1035

ATC TTT GCC TCC CGT CGC TTG CAC CTG GAC CTG CTA TAC AAT GTT CTT       3167
Ile Phe Ala Ser Arg Arg Leu His Leu Asp Leu Leu Tyr Asn Val Leu
    1040                1045                1050

CGA TCA CCC ATG AGT TTC TTC GAG CGT ACA CCC AGT GGG AAC CTA GTG       3215
Arg Ser Pro Met Ser Phe Phe Glu Arg Thr Pro Ser Gly Asn Leu Val
1055                1060                1065                1070

AAC CGA TTC TCC AAG GAG CTG GAC ACA GTG GAC TCC ATG ATC CCG CAG       3263
Asn Arg Phe Ser Lys Glu Leu Asp Thr Val Asp Ser Met Ile Pro Gln
                1075                1080                1085

GTC ATC AAG ATG TTC ATG GGT TCA CTC TTC AGT GTC ATT GGA GCT GTC       3311
Val Ile Lys Met Phe Met Gly Ser Leu Phe Ser Val Ile Gly Ala Val
            1090                1095                1100

ATC ATC ATC CTA CTG GCC ACG CCC ATT GCC GCA GTC ATC ATC CCA CCC       3359
Ile Ile Ile Leu Leu Ala Thr Pro Ile Ala Ala Val Ile Ile Pro Pro
        1105                1110                1115

TTG GGT CTG GTT TAC TTC TTT GTG CAG AGG TTC TAT GTG GCT TCC TCA       3407
Leu Gly Leu Val Tyr Phe Phe Val Gln Arg Phe Tyr Val Ala Ser Ser
    1120                1125                1130

AGA CAA CTG AAG CGC CTG GAG TCT GTC AGC CGT TCC CCT GTG TAC TCA       3455
Arg Gln Leu Lys Arg Leu Glu Ser Val Ser Arg Ser Pro Val Tyr Ser
1135                1140                1145                1150

CAC TTC AAT GAG ACC TTG CTG GGA GTC AGT GTC ATC CGT GCT TTT GAG       3503
His Phe Asn Glu Thr Leu Leu Gly Val Ser Val Ile Arg Ala Phe Glu
                1155                1160                1165

GAG CAG GAG CGC TTC ATT CAC CAG AGT GAC CTG AAA GTA GAT GAG AAC       3551
Glu Gln Glu Arg Phe Ile His Gln Ser Asp Leu Lys Val Asp Glu Asn
            1170                1175                1180

CAG AAG GCC TAC TAC CCC AGC ATT GTG GCC AAC AGA TGG CTT GCT GTG       3599
Gln Lys Ala Tyr Tyr Pro Ser Ile Val Ala Asn Arg Trp Leu Ala Val
        1185                1190                1195

CGC CTT GAG TGT GTG GGC AAC TGC ATT GTG CTG TTT GCT GCC CTC TTT       3647
Arg Leu Glu Cys Val Gly Asn Cys Ile Val Leu Phe Ala Ala Leu Phe
    1200                1205                1210

GCA GTC ATC TCC CGG CAC AGC CTC AGT GCT GGC TTG GTG GGC CTC TCT       3695
Ala Val Ile Ser Arg His Ser Leu Ser Ala Gly Leu Val Gly Leu Ser
1215                1220                1225                1230

GTG TCT TAC TCA CTG CAG ATA ACT GCA TAC TTG AAC TGG CTG GTT CGA       3743
Val Ser Tyr Ser Leu Gln Ile Thr Ala Tyr Leu Asn Trp Leu Val Arg
                1235                1240                1245

ATG TCC TCG GAG ATG GAG ACC AAC ATT GTG GCA GTG GAG AGA CTG AAG       3791
Met Ser Ser Glu Met Glu Thr Asn Ile Val Ala Val Glu Arg Leu Lys
            1250                1255                1260

GAG TAT TCT GAA ACA GAG AAG GAG GCT CCT TGG CAA ATC CAG GAA ACA       3839
Glu Tyr Ser Glu Thr Glu Lys Glu Ala Pro Trp Gln Ile Gln Glu Thr
```

```
                1265                1270                1275
GCT CCA CCC AGC ACC TGG CCC CAT TCA GGC CGT GTA GAG TTC CGG GAT    3887
Ala Pro Pro Ser Thr Trp Pro His Ser Gly Arg Val Glu Phe Arg Asp
    1280                1285                1290

TAC TGC CTG AGG TAT CGA GAA GAC TTG GAC TTG GTT CTC AAG CAC ATA    3935
Tyr Cys Leu Arg Tyr Arg Glu Asp Leu Asp Leu Val Leu Lys His Ile
1295                1300                1305                1310

AAT GTC ACC ATT GAG GGT GGA GAA AAG GTG GGT ATT GTA GGT CGT ACG    3983
Asn Val Thr Ile Glu Gly Gly Glu Lys Val Gly Ile Val Gly Arg Thr
                1315                1320                1325

GGA GCT GGG AAA TCA TCT CTC ACC CTG GGT TTG TTC CGG ATC AAT GAG    4031
Gly Ala Gly Lys Ser Ser Leu Thr Leu Gly Leu Phe Arg Ile Asn Glu
        1330                1335                1340

TCT GCA GAA GGG GAG ATC ATC ATT GAT GGG GTC AAC ATC GCC AAG ATC    4079
Ser Ala Glu Gly Glu Ile Ile Ile Asp Gly Val Asn Ile Ala Lys Ile
    1345                1350                1355

GGC CTG CAC AAC CTG CGC TTC AAG ATC ACC ATC ATT CCA CAG GAT CCT    4127
Gly Leu His Asn Leu Arg Phe Lys Ile Thr Ile Ile Pro Gln Asp Pro
1360                1365                1370

GTT TTG TTC TCG GGT TCC CTC CGC ATG AAC TTG GAC CCT TTC AGT CAG    4175
Val Leu Phe Ser Gly Ser Leu Arg Met Asn Leu Asp Pro Phe Ser Gln
1375                1380                1385                1390

TAT TCT GAT GAA GAA GTC TGG ATG GCC CTG GAG CTT GCT CAC CTA AAG    4223
Tyr Ser Asp Glu Glu Val Trp Met Ala Leu Glu Leu Ala His Leu Lys
                1395                1400                1405

GGC TTT GTG TCA GCC TTG CCT GAC AAG CTG AAC CAT GAG TGT GCA GAA    4271
Gly Phe Val Ser Ala Leu Pro Asp Lys Leu Asn His Glu Cys Ala Glu
        1410                1415                1420

GGT GGA GAG AAC CTG AGT GTG GGG CAG CGA CAG CTT GTG TGC CTG GCC    4319
Gly Gly Glu Asn Leu Ser Val Gly Gln Arg Gln Leu Val Cys Leu Ala
    1425                1430                1435

CGG GCT CTG CTG AGG AAG ACA AAG ATT CTA GTG TTG GAC GAG GCT ACC    4367
Arg Ala Leu Leu Arg Lys Thr Lys Ile Leu Val Leu Asp Glu Ala Thr
1440                1445                1450

GCA GCT GTG GAC CTA GAG ACA GAT AAC CTT ATC CAG TCC ACC ATC CGG    4415
Ala Ala Val Asp Leu Glu Thr Asp Asn Leu Ile Gln Ser Thr Ile Arg
1455                1460                1465                1470

ACG CAG TTT GAA GAC TGT ACT GTG CTC ACG ATT GCT CAT CGG CTT AAC    4463
Thr Gln Phe Glu Asp Cys Thr Val Leu Thr Ile Ala His Arg Leu Asn
                1475                1480                1485

ACC ATA ATG GAC TAC ACA CGG GTT ATT GTC CTG GAC AAA GGA GAA GTT    4511
Thr Ile Met Asp Tyr Thr Arg Val Ile Val Leu Asp Lys Gly Glu Val
        1490                1495                1500

CGG GAG TGT GGT GCA CCC TCT GAG CTC CTG CAG CAA AGA GGC ATC TTC    4559
Arg Glu Cys Gly Ala Pro Ser Glu Leu Leu Gln Gln Arg Gly Ile Phe
    1505                1510                1515

TAC AGC ATG GCC AAG GAT GCT GGC TTG GTG TGAGCTGGTC TCTGGCTTAT      4609
Tyr Ser Met Ala Lys Asp Ala Gly Leu Val
1520                1525

CCAATGAGGA CTGCAGGGCC AGGATCCCAG TGTCCAGGCA TGAGCCAGCA ACCCTGGAAA   4669

CCTACGCTTC CCAGACAAAA CCCAAAAATT AAAAACAAAA CCAAACTAAA AGGAAGCAAA   4729

ATACTTAGGT GTCTGTCACC ATTTGGCTTC ATCCTGGATC TGACCTTGAA GAAGCTGGAA   4789

GACAGATGCA CCCCACTTCA GATACACGTC TGGCCTCTGG CACCCTGAAA GTTCACCCAT   4849

GCTCCTGCCG TATCCCACGG CAAGTCCATG GGCAGCTAAA CATACTAGTG ACCAAACACA   4909

AGCCACACTG CCTCATGTCT CTTCAGCCAC GTCTACGGAT GCCAAGCCTT GTAGCCTCTC   4969

CTGGCTTTGC CAGCTCTCTG TCACCTATAG TCGTGTTGGT TACAGAAGAG TGCATCTTGC   5029
```

-continued

```
CTTCAGGTCT TGCAGTTGAA ACATGGAAC CAAAATGAAC AAAAAGGAGA GAAAGAAAAC    5089

CCCTAAAACG TTCCTGTCCC TGTTATGTCA GTGATGTCCC CTTCCTGCCA TCTGGTCTTC    5149

ATGCACGCTG ACACTGTCCC TTCTTCAGCA CAGCTTTCAC AGGACCTGCT TAAGACACGG    5209

CCTTGTGAAG GGACCTAGGC AGACAGGCTT GGAACCAGGC CAGGCAACAC TCCCTTCACA    5269

AGGACTTATA CCTTGCCCCT GCTTTCTGTT TCTTCCTGTT CAAAGCTGGG GAGGGCTCAC    5329

TCCTCACATA AGGTCTATGA ATAGTTATAA GCAGCAAAAG TCAAGAGCAG AAGGGATGGT    5389

GCCTGCGGGC AAGAATCTGG TATCAAAGAC AGCCAGAGTT TCTTATAGGG CCAGAAGAGA    5449

ACCATTCACA AATATCAGTG ATTTCTCCCC ACTACTTTTG AGCATCGTTT CGTGGAGAAG    5509

GATAGTCCCA AGAATTTGAT GTCTGGGAGA AGGTACTAGA TTCAGGGAGC AGCCATGCCC    5569

AGCTCTGCAC TTGATCCTCA GTCTGAATAC TTCAAAGTGG TCCTCTAGGT TGTGTGAGTT    5629

ACAGACCAAA GAGAGACCCC CATGGTTAGC AAGAACTTGA TGCCAGCCAC AGTTCATACT    5689

TGCTTTGAAT TTTGGCTCTA ATGTCAGTCC CAGAGAAGCA TCCTTTTTCT TTAGGTGGCA    5749

ATATATGTAT TTATTTTTTG TAAGTTAATA CCATTCTTTC ACTTTAAAGG GCCCAGATTT    5809

CTCCTGAGAG TCTTTTTGTA ATGACACTGG AAACATGACT ATTTGAAAAT AATTTGCAGT    5869

AAAGAAAAAT ATTTCATCCG                                                5889
```

(2) INFORMATION FOR SEQ ID NO:6:

(i) SEQUENCE CHARACTERISTICS:
        (A) LENGTH: 1528 amino acids
        (B) TYPE: amino acid
        (D) TOPOLOGY: linear (ii) MOLECULE TYPE: protein (xi) SEQUENCE DESCRIPTION: SEQ ID NO:6:

```
        Met Ala Leu Arg Ser Phe Cys Ser Ala Asp Gly Ser Asp Pro
        1               5                  10

Leu Trp Asp Trp Asn Val Thr Trp His Thr Ser Asn Pro Asp Phe Thr
15                  20                  25                  30

Lys Cys Phe Gln Asn Thr Val Leu Thr Trp Val Pro Cys Phe Tyr Leu
                    35                  40                  45

Trp Ser Cys Phe Pro Leu Tyr Phe Phe Tyr Leu Ser Arg His Asp Arg
                50                  55                  60

Gly Tyr Ile Gln Met Thr His Leu Asn Lys Thr Lys Thr Ala Leu Gly
                65                  70                  75

Phe Phe Leu Trp Ile Ile Cys Trp Ala Asp Leu Phe Tyr Ser Phe Trp
    80                  85                  90

Glu Arg Ser Gln Gly Val Leu Arg Ala Pro Val Leu Val Ser Pro
95                  100                 105                 110

Thr Leu Leu Gly Ile Thr Met Leu Leu Ala Thr Phe Leu Ile Gln Leu
                    115                 120                 125

Glu Arg Arg Lys Gly Val Gln Ser Ser Gly Ile Met Leu Thr Phe Trp
                    130                 135                 140

Leu Val Ala Leu Leu Cys Ala Leu Ala Ile Leu Arg Ser Lys Ile Ile
                    145                 150                 155

Ser Ala Leu Lys Lys Asp Ala His Val Asp Val Phe Arg Asp Ser Thr
                    160                 165                 170

Phe Tyr Leu Tyr Phe Thr Leu Val Leu Val Gln Leu Val Leu Ser Cys
175                 180                 185                 190

Phe Ser Asp Cys Ser Pro Leu Phe Ser Glu Thr Val His Asp Arg Asn
                    195                 200                 205
```

```
Pro Cys Pro Glu Ser Ser Ala Ser Phe Leu Ser Arg Ile Thr Phe Trp
        210                 215                 220
Trp Ile Thr Gly Met Met Val His Gly Tyr Arg Gln Pro Leu Glu Ser
            225                 230                 235
Ser Asp Leu Trp Ser Leu Asn Lys Glu Asp Thr Ser Glu Glu Val Val
240                 245                 250
Pro Val Leu Val Asn Asn Trp Lys Lys Glu Cys Asp Lys Ser Arg Lys
255                 260                 265                 270
Gln Pro Val Arg Ile Val Tyr Ala Pro Pro Lys Asp Pro Ser Lys Pro
                275                 280                 285
Lys Gly Ser Ser Gln Leu Asp Val Asn Glu Glu Val Glu Ala Leu Ile
            290                 295                 300
Val Lys Ser Pro His Lys Asp Arg Glu Pro Ser Leu Phe Lys Val Leu
            305                 310                 315
Tyr Lys Thr Phe Gly Pro Tyr Phe Leu Met Ser Phe Leu Tyr Lys Ala
            320                 325                 330
Leu His Asp Leu Met Met Phe Ala Gly Pro Lys Ile Leu Glu Leu Ile
335                 340                 345                 350
Ile Asn Phe Val Asn Asp Arg Glu Ala Pro Asp Trp Gln Gly Tyr Phe
                355                 360                 365
Tyr Thr Ala Leu Leu Phe Val Ser Ala Cys Leu Gln Thr Leu Ala Leu
                370                 375                 380
His Gln Tyr Phe His Ile Cys Phe Val Ser Gly Met Arg Ile Lys Thr
            385                 390                 395
Ala Val Val Gly Ala Val Tyr Arg Lys Ala Leu Leu Ile Thr Asn Ala
            400                 405                 410
Ala Arg Lys Ser Ser Thr Val Gly Glu Ile Val Asn Leu Met Ser Val
415                 420                 425                 430
Asp Ala Gln Arg Phe Met Asp Leu Ala Thr Tyr Ile Asn Met Ile Trp
                435                 440                 445
Ser Ala Pro Leu Gln Val Ile Leu Ala Leu Tyr Phe Leu Trp Leu Ser
            450                 455                 460
Leu Gly Pro Ser Val Leu Ala Gly Val Ala Val Met Ile Leu Met Val
            465                 470                 475
Pro Leu Asn Ala Val Met Ala Met Lys Thr Lys Thr Tyr Gln Val Ala
480                 485                 490
His Met Lys Ser Lys Asp Asn Arg Ile Lys Leu Met Asn Glu Ile Leu
495                 500                 505                 510
Asn Gly Ile Lys Val Leu Lys Leu Tyr Ala Trp Glu Leu Ala Phe Gln
                515                 520                 525
Asp Lys Val Met Ser Ile Arg Gln Glu Glu Leu Lys Val Leu Lys Lys
                530                 535                 540
Ser Ala Tyr Leu Ala Ala Val Gly Thr Phe Thr Trp Val Cys Thr Pro
            545                 550                 555
Phe Leu Val Ala Leu Ser Thr Phe Ala Val Phe Val Thr Val Asp Glu
560                 565                 570
Arg Asn Ile Leu Asp Ala Lys Lys Ala Phe Val Ser Leu Ala Leu Phe
575                 580                 585                 590
Asn Ile Leu Arg Phe Pro Leu Asn Ile Leu Pro Met Val Ile Ser Ser
                595                 600                 605
Ile Val Gln Ala Ser Val Ser Leu Lys Arg Leu Arg Ile Phe Leu Ser
            610                 615                 620
His Glu Glu Leu Glu Pro Asp Ser Ile Glu Arg Arg Ser Ile Lys Ser
```

-continued

```
                625                 630                 635
Gly Glu Gly Asn Ser Ile Thr Val Lys Asn Ala Thr Phe Thr Trp Ala
            640                 645                 650
Arg Gly Glu Pro Pro Thr Leu Asn Gly Ile Thr Phe Ser Ile Pro Glu
655                 660                 665                 670
Gly Ala Leu Val Ala Val Gly Gln Val Gly Cys Gly Lys Ser Ser
            675                 680                 685
Leu Leu Ser Ala Leu Leu Ala Glu Met Asp Lys Val Glu Gly His Val
            690                 695                 700
Thr Leu Lys Gly Ser Val Ala Tyr Val Pro Gln Gln Ala Trp Ile Gln
            705                 710                 715
Asn Asp Ser Leu Arg Glu Asn Ile Leu Phe Gly His Pro Leu Gln Glu
720                 725                 730
Asn Tyr Tyr Lys Ala Val Met Glu Ala Cys Ala Leu Leu Pro Asp Leu
735                 740                 745                 750
Glu Ile Leu Pro Ser Gly Asp Arg Thr Glu Ile Gly Glu Lys Gly Val
                755                 760                 765
Asn Leu Ser Gly Gly Gln Lys Gln Arg Val Ser Leu Ala Arg Ala Val
            770                 775                 780
Tyr Ser Asn Ser Asp Ile Tyr Leu Phe Asp Asp Pro Leu Ser Ala Val
            785                 790                 795
Asp Ala His Val Gly Lys His Ile Phe Glu Lys Val Val Gly Pro Met
800                 805                 810
Gly Leu Leu Lys Asn Lys Thr Arg Ile Leu Val Thr His Gly Ile Ser
815                 820                 825                 830
Tyr Leu Pro Gln Val Asp Val Ile Ile Val Met Ser Gly Gly Lys Ile
                835                 840                 845
Ser Glu Met Gly Ser Tyr Gln Glu Leu Leu Asp Arg Asp Gly Ala Phe
                850                 855                 860
Ala Glu Phe Leu Arg Thr Tyr Ala Asn Ala Glu Gln Asp Leu Ala Ser
            865                 870                 875
Glu Asp Asp Ser Val Ser Gly Ser Gly Lys Glu Ser Lys Pro Val Glu
880                 885                 890
Asn Gly Met Leu Val Thr Asp Thr Val Gly Lys His Leu Gln Arg His
895                 900                 905                 910
Leu Ser Asn Ser Ser His Ser Gly Asp Thr Ser Gln Gln His Ser
                915                 920                 925
Ser Ile Ala Glu Leu Gln Lys Ala Gly Ala Lys Glu Thr Trp Lys
            930                 935                 940
Leu Met Glu Ala Asp Lys Ala Gln Thr Gly Gln Val Gln Leu Ser Val
            945                 950                 955
Tyr Trp Asn Tyr Met Lys Ala Ile Gly Leu Phe Ile Thr Phe Leu Ser
            960                 965                 970
Ile Phe Leu Phe Leu Cys Asn His Val Ser Ala Leu Ala Ser Asn Tyr
975                 980                 985                 990
Trp Leu Ser Leu Trp Thr Asp Asp Pro Pro Val Val Asn Gly Thr Gln
                995                 1000                1005
Ala Asn Arg Asn Phe Arg Leu Ser Val Tyr Gly Ala Leu Gly Ile Leu
            1010                1015                1020
Gln Gly Ala Ala Ile Phe Gly Tyr Ser Met Ala Val Ser Ile Gly Gly
            1025                1030                1035
Ile Phe Ala Ser Arg Arg Leu His Leu Asp Leu Leu Tyr Asn Val Leu
            1040                1045                1050
```

-continued

```
Arg Ser Pro Met Ser Phe Phe Glu Arg Thr Pro Ser Gly Asn Leu Val
1055                1060                1065                1070

Asn Arg Phe Ser Lys Glu Leu Asp Thr Val Asp Ser Met Ile Pro Gln
            1075                1080                1085

Val Ile Lys Met Phe Met Gly Ser Leu Phe Ser Val Ile Gly Ala Val
        1090                1095                1100

Ile Ile Ile Leu Leu Ala Thr Pro Ile Ala Ala Val Ile Ile Pro Pro
    1105                1110                1115

Leu Gly Leu Val Tyr Phe Phe Val Gln Arg Phe Tyr Val Ala Ser Ser
1120                1125                1130

Arg Gln Leu Lys Arg Leu Glu Ser Val Ser Arg Ser Pro Val Tyr Ser
1135                1140                1145                1150

His Phe Asn Glu Thr Leu Leu Gly Val Ser Val Ile Arg Ala Phe Glu
            1155                1160                1165

Glu Gln Glu Arg Phe Ile His Gln Ser Asp Leu Lys Val Asp Glu Asn
        1170                1175                1180

Gln Lys Ala Tyr Tyr Pro Ser Ile Val Ala Asn Arg Trp Leu Ala Val
    1185                1190                1195

Arg Leu Glu Cys Val Gly Asn Cys Ile Val Leu Phe Ala Ala Leu Phe
1200                1205                1210

Ala Val Ile Ser Arg His Ser Leu Ser Ala Gly Leu Val Gly Leu Ser
1215                1220                1225                1230

Val Ser Tyr Ser Leu Gln Ile Thr Ala Tyr Leu Asn Trp Leu Val Arg
            1235                1240                1245

Met Ser Ser Glu Met Glu Thr Asn Ile Val Ala Val Glu Arg Leu Lys
        1250                1255                1260

Glu Tyr Ser Glu Thr Glu Lys Glu Ala Pro Trp Gln Ile Gln Glu Thr
    1265                1270                1275

Ala Pro Pro Ser Thr Trp Pro His Ser Gly Arg Val Glu Phe Arg Asp
1280                1285                1290

Tyr Cys Leu Arg Tyr Arg Glu Asp Leu Asp Leu Val Leu Lys His Ile
1295                1300                1305                1310

Asn Val Thr Ile Glu Gly Gly Glu Lys Val Gly Ile Val Gly Arg Thr
            1315                1320                1325

Gly Ala Gly Lys Ser Ser Leu Thr Leu Gly Leu Phe Arg Ile Asn Glu
        1330                1335                1340

Ser Ala Glu Gly Glu Ile Ile Ile Asp Gly Val Asn Ile Ala Lys Ile
    1345                1350                1355

Gly Leu His Asn Leu Arg Phe Lys Ile Thr Ile Ile Pro Gln Asp Pro
1360                1365                1370

Val Leu Phe Ser Gly Ser Leu Arg Met Asn Leu Asp Pro Phe Ser Gln
1375                1380                1385                1390

Tyr Ser Asp Glu Glu Val Trp Met Ala Leu Glu Leu Ala His Leu Lys
            1395                1400                1405

Gly Phe Val Ser Ala Leu Pro Asp Lys Leu Asn His Glu Cys Ala Glu
        1410                1415                1420

Gly Gly Glu Asn Leu Ser Val Gly Gln Arg Gln Leu Val Cys Leu Ala
    1425                1430                1435

Arg Ala Leu Leu Arg Lys Thr Lys Ile Leu Val Leu Asp Glu Ala Thr
1440                1445                1450

Ala Ala Val Asp Leu Glu Thr Asp Asn Leu Ile Gln Ser Thr Ile Arg
1455                1460                1465                1470

Thr Gln Phe Glu Asp Cys Thr Val Leu Thr Ile Ala His Arg Leu Asn
            1475                1480                1485
```

```
Thr Ile Met Asp Tyr Thr Arg Val Ile Val Leu Asp Lys Gly Glu Val
        1490                1495                1500

Arg Glu Cys Gly Ala Pro Ser Glu Leu Leu Gln Gln Arg Gly Ile Phe
        1505                1510                1515

Tyr Ser Met Ala Lys Asp Ala Gly Leu Val
1520                1525
```